(12) United States Patent
Grotz

(10) Patent No.: US 10,617,527 B2
(45) Date of Patent: *Apr. 14, 2020

(54) RESILIENT KNEE IMPLANT AND METHODS

(71) Applicant: iOrthopedics, Inc., Las Vegas, NV (US)

(72) Inventor: Robert Thomas Grotz, Las Vegas, NV (US)

(73) Assignee: IORTHOPEDICS, INC., Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/386,526

(22) Filed: Apr. 17, 2019

(65) Prior Publication Data
US 2019/0336298 A1    Nov. 7, 2019

Related U.S. Application Data

(60) Continuation of application No. 15/807,901, filed on Nov. 9, 2017, now Pat. No. 10,307,257, which is a
(Continued)

(51) Int. Cl.
*A61F 2/38* (2006.01)
*C08L 75/04* (2006.01)
(Continued)

(52) U.S. Cl.
CPC ........ *A61F 2/3859* (2013.01); *A61B 17/0642* (2013.01); *A61B 17/562* (2013.01);
(Continued)

(58) Field of Classification Search
CPC .......... A61F 2/3859; A61F 2/38; A61F 2/461; A61F 2002/2825
See application file for complete search history.

(56) References Cited

U.S. PATENT DOCUMENTS

| | | |
|---|---|---|
| 3,864,758 A | 2/1975 | Yakich |
| 3,867,728 A | 2/1975 | Stubstad et al. |

(Continued)

FOREIGN PATENT DOCUMENTS

| | | |
|---|---|---|
| DE | 2501080 A1 | 7/1976 |
| DE | 10339605 A1 | 4/2005 |

(Continued)

OTHER PUBLICATIONS

Co-pending U.S. Appl. No. 14/846,651, filed Sep. 4, 2015.
(Continued)

*Primary Examiner* — Jason-Dennis N Stewart
(74) *Attorney, Agent, or Firm* — Michel Graffeo

(57) ABSTRACT

This disclosure is directed to a resilient interpositional arthroplasty implant. Such implants function to pad cartilage defects, cushion, and replace or restore the articular surface, which may preserve joint integrity, reduce pain and improve function. The implant may endure variable joint compressive and shear forces and cyclic loads. The implant may repair, reconstruct, and regenerate joint anatomy, and thereby improve upon joint replacement alternatives. The walls of this invention may capture, distribute and hold living cells until aggregation and hyaline cartilage regrowth occurs. The implant may be deployed into debrided joint spaces, molding and conforming to surrounding structures with sufficient stability so as to enable immediate limb use after outpatient surgery. Appendages of the implant may repair or reconstruct tendons or ligaments, and menisci by interpositional inflatable or compliant polymer arthroplasties that promote anatomic joint motion.

11 Claims, 21 Drawing Sheets

Related U.S. Application Data continuation-in-part of application No. 15/608,885, filed on May 30, 2017, now Pat. No. 10,004,605, which is a division of application No. 14/289,431, filed on May 28, 2014, now Pat. No. 9,662,218, which is a continuation of application No. 13/574,499, filed as application No. PCT/US2011/021674 on Jan. 19, 2011, now Pat. No. 8,771,363, application No. 16/386,526, which is a continuation of application No. 16/033,050, filed on Jul. 11, 2018, now Pat. No. 10,307,258, which is a continuation of application No. 15/807,901, filed on Nov. 9, 2017, now Pat. No. 10,307,257, which is a continuation-in-part of application No. 15/651,958, filed on Jul. 17, 2017, now Pat. No. 10,045,851, which is a continuation of application No. 14/239,992, filed as application No. PCT/US2012/053207 on Aug. 30, 2012, now Pat. No. 9,757,241.

(60) Provisional application No. 61/297,698, filed on Jan. 22, 2010, provisional application No. 61/530,324, filed on Sep. 1, 2011.

(51) Int. Cl.
  *A61L 27/54* (2006.01)
  *A61L 27/38* (2006.01)
  *A61L 27/18* (2006.01)
  *A61B 17/064* (2006.01)
  *A61B 17/56* (2006.01)
  *A61F 2/30* (2006.01)

(52) U.S. Cl.
  CPC .......... *A61L 27/18* (2013.01); *A61L 27/3817* (2013.01); *A61L 27/54* (2013.01); *C08L 75/04* (2013.01); *A61B 2017/561* (2013.01); *A61F 2/38* (2013.01); *A61F 2/3872* (2013.01); *A61F 2002/30563* (2013.01); *A61F 2002/30578* (2013.01); *A61F 2002/30583* (2013.01); *A61F 2002/30586* (2013.01); *A61F 2002/30677* (2013.01); *A61F 2002/30754* (2013.01); *A61F 2002/30772* (2013.01); *A61F 2002/3863* (2013.01); *A61L 2300/402* (2013.01); *A61L 2300/404* (2013.01); *A61L 2300/406* (2013.01); *A61L 2300/414* (2013.01); *A61L 2300/416* (2013.01); *A61L 2300/452* (2013.01); *A61L 2300/64* (2013.01); *A61L 2430/24* (2013.01)

(56) References Cited

U.S. PATENT DOCUMENTS

| | | | |
|---|---|---|---|
| 4,219,892 A | 9/1980 | Rigdon | |
| 4,344,193 A | 8/1982 | Kenny | |
| 4,467,479 A | 8/1984 | Brody | |
| 4,502,161 A | 3/1985 | Wall | |
| 4,919,667 A | 4/1990 | Richmond | |
| 4,919,668 A | 4/1990 | Rosenbaum et al. | |
| 4,932,969 A | 6/1990 | Frey et al. | |
| 5,171,282 A | 12/1992 | Pequignot | |
| 5,195,542 A | 3/1993 | Gazielly et al. | |
| 5,344,459 A | 9/1994 | Swartz | |
| 5,383,456 A | 1/1995 | Arnold et al. | |
| 5,441,508 A | 8/1995 | Gazielly et al. | |
| 6,056,777 A | 5/2000 | McDowell | |
| 6,110,211 A | 8/2000 | Weiss | |
| 6,132,468 A | 10/2000 | Mansmann | |
| 6,193,761 B1 | 2/2001 | Treacy | |
| 6,248,110 B1 | 6/2001 | Reiley et al. | |
| 6,423,083 B2 | 7/2002 | Reiley et al. | |
| 6,482,209 B1 | 11/2002 | Engh et al. | |
| 6,783,546 B2 | 9/2004 | Zucherman et al. | |
| 7,001,385 B2 | 2/2006 | Bonutti | |
| 7,291,169 B2 | 11/2007 | Hodorek | |
| 7,338,524 B2 | 3/2008 | Fell et al. | |
| 7,491,235 B2 | 2/2009 | Fell | |
| 7,531,000 B2 | 5/2009 | Hodorek | |
| 7,611,653 B1 | 11/2009 | Elsner et al. | |
| 7,670,381 B2 | 3/2010 | Schwartz | |
| 7,803,193 B2 | 9/2010 | Steinberg | |
| 7,850,983 B2 | 12/2010 | Sevrain et al. | |
| 7,972,380 B2 | 7/2011 | Linares | |
| 7,976,578 B2 | 7/2011 | Marvel | |
| 8,192,491 B2 | 6/2012 | Fox | |
| 8,287,594 B2 | 10/2012 | Cragg et al. | |
| 8,292,954 B2 | 10/2012 | Robinson et al. | |
| 8,292,955 B2 | 10/2012 | Robinson et al. | |
| 8,333,805 B2 | 12/2012 | Williams, III | |
| 8,357,203 B2 | 1/2013 | White et al. | |
| 8,361,147 B2 | 1/2013 | Shterling et al. | |
| 8,403,985 B2 | 3/2013 | Hodorek | |
| 8,636,806 B2 | 1/2014 | Osman | |
| 8,679,190 B2 | 3/2014 | Myung et al. | |
| 8,764,830 B2 | 7/2014 | Robinson et al. | |
| 8,771,363 B2 | 7/2014 | Grotz | |
| 8,834,568 B2 | 9/2014 | Shapiro | |
| 8,945,222 B2 | 2/2015 | Linares | |
| 8,999,000 B2 | 4/2015 | Hodorek et al. | |
| 9,662,218 B2 | 5/2017 | Grotz | |
| 2002/0143402 A1 | 10/2002 | Steinberg | |
| 2003/0093152 A1 | 5/2003 | Pedersen et al. | |
| 2003/0163202 A1 | 8/2003 | Lakin | |
| 2003/0220649 A1 | 11/2003 | Bao et al. | |
| 2004/0006393 A1 | 1/2004 | Burkinshaw | |
| 2004/0039450 A1 | 2/2004 | Griner et al. | |
| 2004/0260396 A1 | 12/2004 | Ferree et al. | |
| 2004/0267375 A1 | 12/2004 | Friedrichs | |
| 2005/0171604 A1 | 8/2005 | Michalow | |
| 2005/0182463 A1 | 8/2005 | Hunter et al. | |
| 2006/0024076 A1 | 2/2006 | Kato et al. | |
| 2006/0047341 A1 | 3/2006 | Trieu | |
| 2006/0058892 A1 | 3/2006 | Lesh | |
| 2006/0122622 A1 | 6/2006 | Truckai et al. | |
| 2006/0122623 A1 | 6/2006 | Truckai et al. | |
| 2006/0190078 A1 | 8/2006 | Fell | |
| 2006/0235517 A1 | 10/2006 | Hodorek | |
| 2007/0016300 A1 | 1/2007 | Kuslich | |
| 2007/0078517 A1 | 4/2007 | Engh et al. | |
| 2007/0100461 A1 | 5/2007 | Incavo et al. | |
| 2007/0112428 A1 | 5/2007 | Lancial et al. | |
| 2007/0112458 A1 | 5/2007 | Kondo et al. | |
| 2007/0135920 A1 | 6/2007 | Ferree | |
| 2007/0150067 A1 | 6/2007 | Roger et al. | |
| 2007/0179607 A1 | 8/2007 | Hoderek et al. | |
| 2007/0276491 A1 | 11/2007 | Ahrens et al. | |
| 2007/0288095 A1 | 12/2007 | Wirtel et al. | |
| 2008/0071373 A1 | 3/2008 | Moltz | |
| 2008/0200989 A1 | 8/2008 | Cachia | |
| 2008/0208346 A1 | 8/2008 | Schwartz | |
| 2008/0234820 A1 | 9/2008 | Felt et al. | |
| 2008/0249638 A1 | 10/2008 | Asgari | |
| 2009/0043344 A1 | 2/2009 | Schlotterback | |
| 2009/0076605 A1 | 3/2009 | Linares | |
| 2009/0187252 A1 | 7/2009 | Howald | |
| 2009/0234453 A1 | 9/2009 | Steinberg | |
| 2009/0259313 A1 | 10/2009 | Elsner et al. | |
| 2009/0259314 A1 | 10/2009 | Linder-Ganz et al. | |
| 2009/0306778 A1 | 12/2009 | Marvel | |
| 2009/0312807 A1 | 12/2009 | Boudreault et al. | |
| 2010/0010114 A1 | 1/2010 | Myung et al. | |
| 2010/0023126 A1 | 1/2010 | Grotz | |
| 2010/0042215 A1 | 2/2010 | Stalcup et al. | |
| 2010/0256758 A1 | 10/2010 | Gordon et al. | |
| 2011/0066243 A1 | 3/2011 | Rivin et al. | |
| 2011/0082424 A1 | 4/2011 | Barnhouse et al. | |
| 2011/0288642 A1 | 11/2011 | Forsell | |
| 2012/0316645 A1 | 12/2012 | Grotz | |
| 2013/0018479 A1 | 1/2013 | Grotz | |
| 2013/0030542 A1 | 1/2013 | Grotz | |

(56) References Cited

U.S. PATENT DOCUMENTS

| | | |
|---|---|---|
| 2013/0096691 A1 | 4/2013 | Myung et al. |
| 2013/0138211 A1 | 5/2013 | Myung et al. |
| 2013/0204377 A1 | 8/2013 | Samuelson et al. |
| 2014/0257500 A1 | 9/2014 | Grotz |

FOREIGN PATENT DOCUMENTS

| | | |
|---|---|---|
| EP | 2130517 A1 | 12/2009 |
| EP | 2750629 B1 | 7/2016 |
| FR | 2747914 A | 10/1997 |
| FR | 2803190 A1 | 7/2001 |
| KR | 20050100511 A | 10/2005 |
| WO | WO2004100839 A1 | 11/2004 |
| WO | WO2007125060 | 11/2007 |
| WO | WO2009052292 A1 | 4/2009 |
| WO | WO2008111073 A2 | 9/2009 |
| WO | WO2010011338 A2 | 1/2010 |
| WO | WO2010059098 A1 | 5/2010 |
| WO | WO2011091005 A2 | 7/2011 |

OTHER PUBLICATIONS

Co-pending U.S. Appl. No. 14/936,562, filed Nov. 9, 2015.
U.S. Appl. No. 13/514,539 Office Action dated Jul. 8, 2015.
Co-pending U.S. Appl. No. 15/608,885, filed May 30, 2017.
U.S. Appl. No. 13/514,539 Office action dated Dec. 9, 2014.
U.S. Appl. No. 13/574,517 Office action dated Mar. 5, 2015.
PCT/US11/021674 International Search Report and Written Opinion dated Sep. 23, 2011.
PCT/US2010/58977 International Preliminary Report on Patentability dated Feb. 7, 2011.
PCT/US2011/021673 International Preliminary Report on Patentability dated Sep. 16, 2011.
PCT/US2012/53207 International Preliminary Report on Patentability dated Feb. 14, 2013.
U.S. Appl. No. 13/574,517 Office action dated Aug. 15, 2014.
PCT/US09/04305 International Preliminary Report on Patentability dated Jan. 25, 2011.
PCT/US09/04305 International Search Report dated Jan. 19, 2010.
PCT/US11/021674 Search Report and Written Opinion dated Sep. 23, 2011.
PCT/US11/021673 Search Report and Written Opinion dated Sep. 16, 2011.
U.S. Appl. No. 12/460,703 Office Action dated Jun. 7, 2013.
U.S. Appl. No. 12/460,703 Office Action dated Aug. 10, 2011.
U.S. Appl. No. 12/460,703 Office Action dated Nov. 21, 2013.
U.S. Appl. No. 12/460,703 Office Action dated Oct. 2, 2012.
U.S. Appl. No. 12/460,703 Office Action dated Jan. 31, 2012.
U.S. Appl. No. 13/514,539 Office Action dated Feb. 7, 2014.
U.S. Appl. No. 13/514,539 Office Action dated May 16, 2014.
U.S. Appl. No. 13/574,499 Office Action dated Dec. 2, 2013.
U.S. Appl. No. 13/574,517 Office Action dated Feb. 6, 2014.

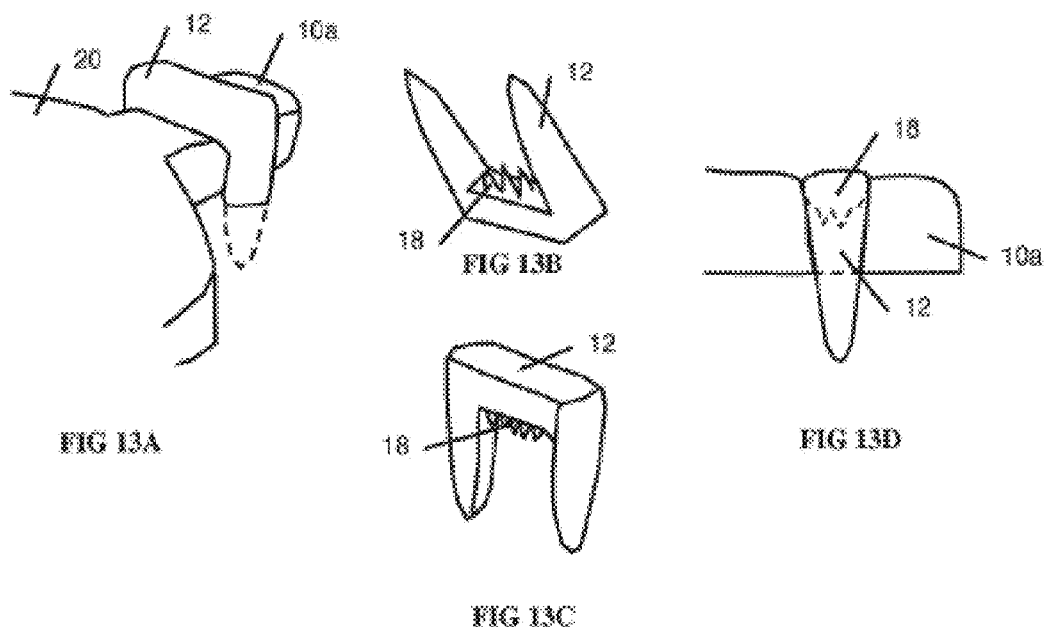
FIG 13A
FIG 13B
FIG 13C
FIG 13D
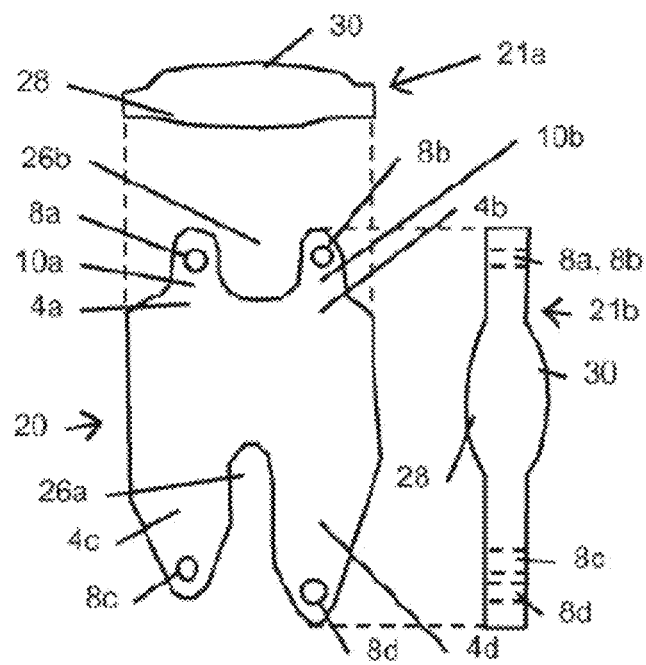
FIG 14

RESILIENT KNEE IMPLANT AND METHODS

RELATED APPLICATIONS

This application is a continuation in part of and claims priority to currently pending U.S. application Ser. No. 15/807,901 filed on Nov. 9, 2017 which claims priority to application Ser. No. 15/608,885 filed on May 30, 2017 and is now U.S. Pat. No. 10,004,605 issued Jun. 26, 2018 which is a divisional of U.S. application Ser. No. 14/289,431 filed on May 28, 2014 now U.S. Pat. No. 9,662,218 issued May 30, 2017 which is a continuation of U.S. application Ser. No. 13/574,499 filed Oct. 8, 2012 now U.S. Pat. No. 8,771,363 issued Jul. 8, 2014 which is the is National Stage Entry of PCT/US2011/021674 filed Jan. 19, 2011, which claims priority to Provisional U.S. Application Ser. No. 61/297,698 filed Jan. 22, 2010, the entire contents of which are incorporated herein by reference in their entirety for any purpose.

This application is a continuation in part of and claims priority to currently pending U.S. application Ser. No. 16/033,050 filed Jul. 11, 2018, which is a continuation of currently pending U.S. application Ser. No. 15/807,901 filed on Nov. 9, 2017, which claims priority to U.S. application Ser. No. 15/651,958 filed on Jul. 17, 2017 and now U.S. Pat. No. 10,045,851 issued Aug. 14, 2018, which is a continuation of U.S. application Ser. No. 14/239,992 filed on Jun. 5, 2014 now U.S. Pat. No. 9,757,241 issued Sep. 12, 2017 which is the National Stage Entry of PCT/US2012/053207 filed on Aug. 30, 2012, which claims priority to Provisional U.S. Application Ser. No. 61/530,324 filed on Sep. 1, 2011, the entire contents of which are incorporated herein by reference in their entirety for any purpose.

BACKGROUND OF THE INVENTION

This invention relates to arthroplasty, and more particularly, to an implant for use in arthroplasty when hyaline articular cartilage is damaged, it breaks down and joint space is lost. Inflammatory enzymes such as from the Cox-1, Cox-2 and/or 5-Lox systems, are released and loose bodies form adding to the degradation of joint function. Such joint damage is conventionally treated by physical therapy, analgesics, pain medication and injections. When these treatments fail, the traditionally accepted treatment option is arthroplasty implantation or replacing the joint with an artificial joint construct. Current arthroplasty techniques typically use "plastic and metal" implants that are rigid and which ultimately fail due to loosening or infection. Conventional materials for the artificial joint components include chrome-cobalt-molybdenum alloy (metal) and high molecular weight polyethylene (plastic). Each is often fixed by a cement-like mixture of methyl methacrylate to the ends of the bones that define the joint that is the subject of the arthroplasty, or coated with a surface that enables bone ingrowth. Replacement surgeries are known to fail in a number of years.

Conditions requiring arthroplasty include traumatic arthritis, osteoarthritis, rheumatoid arthritis, osteonecrosis, and failed surgical procedures.

SUMMARY OF THE INVENTION

The present invention is directed to an orthopedic implant configured for deployment between opposing members of a joint structure that addresses many of the shortcomings of prior artificial joints. The arthroplasty implants embodying features of the invention are configured to preserve joint motions while removing the pain and dysfunction following the development of arthritis or joint injury. The arthroplasty implant in accordance with the present invention achieves improved physiologic motion and shock absorption during gait and acts as a resilient spacer between moving bones during limb movement. The combined characteristics of the implant include anatomic design symmetry, balanced rigidity with variable attachment connections to at least one of adjacent normal structures, and durability which addresses and meets the needs for repair or reconstruction thus far missed in the prior art. The implant should be secured to at least one of the bones of the joint structure.

Provided herein is an implant configured for deployment between a femur and a tibia of a knee joint, the implant comprising a balloon comprising a first portion that is configured to engage a medial condyle and a lateral condyle of the femur of the knee joint, a second portion that is configured to engage the tibia of the knee joint, a side portion connecting the first portion and the second portion, in which the side portion facilitates relative motion between the first portion and the second portion, and an interior that is optionally inflatable with a first inflation medium; and a first appendage configured to couple the balloon to the femur of the knee joint.

In some embodiments, the implant comprises at least one attachment element in the intercondylar notch. In some embodiments, the implant comprises at least one attachment element superiorly at the distal end of the femur anteriorly. In some embodiments, the implant comprises at least one posterior reign configured to cinch up the implant from inside a posterior intercondylar notch toward a connection site around the femur. In some embodiments, the implant comprises at least one suture-like lanyard configured to cinch up the implant from inside a posterior intercondylar notch toward a connection site around the femur.

In some embodiments, the first portion comprises a first wall, the second portion comprises a second wall, and the side portion comprises a side wall.

In some embodiments, the implant is a single layer or monolayer of polymer. In some embodiments, the implant does not have a balloon or inflatable portion thereof. In other embodiments the implant is a multilayered structure, a laminate or a coextruded multilayered device.

In one embodiment, the implant is configured for a knee joint and the implant comprises a first appendage that is configured to engage a medial condyle of a femur of a knee joint, the first appendage comprising a bone engaging surface and an articulating surface, a second appendage that is configured to engage a lateral condyle of a femur of a knee joint, the second appendage comprising a bone engaging surface and an articulating surface, a slot between the first appendage and the second appendage, and a rim defining the periphery of the implant, wherein the bone engaging surface of the first appendage has a similar radial curvature profile as the articulating surface of the first appendage. In another embodiment, the first and second appendage are part of the same implant. In still another embodiment, the first and second appendage are seamlessly part of the same implant and are coextensively juxtaposed. In yet another embodiment the first and second appendage coextensively share a common third appendage.

In another embodiment, the implant may have prefabricated holes for aiding in the attachment of the implant to a bone. The implant may, in some aspects, have a variable thickness or a consistent thickness depending on the needs of the subject receiving the implant. In a preferred embodiment, the implant has an average thickness. In some embodiments, the implant thickness is as thin as possible given the materials used to fabricate the implant so that the implant fits the subject and allows for an improved joint function. Preferably, the thickness of the implant of is from 0.05 to 5 mm. More preferably, the average thickness of the implant of is from 0.05 to 5 mm.

In other aspects, the implant has a rim which defines the periphery of the implant. The rim may be filleted. The filleted rim may have a variable fillet. In some embodiments, prefabricated holes may be made in the rim. In some aspects, the dimensions of the rim are relative to the thickness of the rest of the implant. In other aspects, the rim can have a peripheral boundary and an inner boundary wherein the inner boundary is conterminous or coextensive with the main body or appendages of the implant. In preferred aspects, the rim can have a dimension that is 1 to 3.5 times the thickness of the implant.

In some embodiments, the implant can be implanted without removing or damaging a patient's ligaments or other cooperating bones such as the patella. Therefore, in certain aspects, the implant will function relative to, in cooperation with or in apposition to other parts of the knee joint that were present in the patient prior to implanting of the implant. In a preferred aspect, the implant is implanted while keeping the remainder of the patient's joint intact. In a preferred aspect, the implant is implanted without cutting or damaging any ligaments. In a preferred aspect, the implant is implanted without removing any bone. In some embodiments, the implant comprises an inflation port in communication with the interior of the balloon for inflation of the interior of the balloon with the first inflation medium. In some embodiments, the interior comprises a plurality of inflatable chambers. In some embodiments, a first chamber of the plurality of individually inflatable chambers is adapted to be inflated with the first inflation medium, and a second chamber of the plurality of individually inflatable chambers is adapted to be inflated with a second inflation medium. In some embodiments, the first inflation medium imparts at least one of rigidity in the implant and cushion in the implant.

In some embodiments, the implant comprises a second appendage coupling the balloon to at least one of: the femur of the joint and the tibia of the joint.

Provided herein is an implant configured for deployment between a femur and a tibia of a knee joint, the implant comprising a balloon comprising a first portion that is configured to engage at least one condyle of the femur of the knee joint, a second portion that is configured to engage the tibia of the knee joint, a side portion connecting the first portion and the second portion, in which the side portion facilitates relative motion between the first portion and the second portion, and an interior that is optionally inflatable with a first inflation medium; and a first appendage configured to couple the balloon to the femur of the knee joint.

In some embodiments, the at least one condyle is the medial condyle. In some embodiments, the at least one condyle is the lateral condyle.

In some embodiments, the balloon is at least one of: at most about 1.5 cm in diameter, at most about 1.75 cm in diameter, at most about 2 cm in diameter, at most about 2.25 cm in diameter, at most about 2.5 cm in diameter, at most about 2.75 cm in diameter, at most about 3 cm in diameter, at most about 3.25 cm in diameter, at most about 3.5 cm in diameter, at most about 3.75 cm in diameter, at most about 4 cm in diameter, at most about 4.25 cm in diameter, at most about 4.5 cm in diameter, at most about 4.75 cm in diameter, at most about 5 cm in diameter, at most about 5.25 cm in diameter, at most about 5.5 cm in diameter, at most about 5.75 cm in diameter, at most about 6 cm in diameter, at most about 6.25 cm in diameter, at most about 6.5 cm in diameter, at most about 6.75 cm in diameter, at most about 7 cm in diameter, at most about 7.25 cm in diameter, at most about 7.5 cm in diameter, at most about 7.75 cm in diameter, at most about 8 cm in diameter, at most about 3 cm in length along the longest length of the balloon, at most about 3.25 cm in length along the longest length of the balloon, at most about 3.5 cm in length along the longest length of the balloon, at most about 3.75 cm in length along the longest length of the balloon, at most about 4 cm in length along the longest length of the balloon, at most about 4.25 cm in length along the longest length of the balloon, at most about 4.5 cm in length along the longest length of the balloon, at most about 4.75 cm in length along the longest length of the balloon, at most about 5 cm in length along the longest length of the balloon, at most about 5.25 cm in length along the longest length of the balloon, at most about 5.5 cm in length along the longest length of the balloon, at most about 5.75 cm in length along the longest length of the balloon, at most about 6 cm in length along the longest length of the balloon, 6.25 cm in length along the longest length of the balloon, at most about 6.5 cm in length along the longest length of the balloon, at most about 6.75 cm in length along the longest length of the balloon, at most about 7 cm in length along the longest length of the balloon, at most about 7.25 cm in length along the longest length of the balloon, at most about 7.5 cm in length along the longest length of the balloon, at most about 7.75 cm in length along the longest length of the balloon, and at most about 8 cm in length along the longest length of the balloon.

In some embodiments, the first portion comprises a first wall, the second portion comprises a second wall, and the side portion comprises a side wall.

In some embodiments, the implant comprises an inflation port in communication with the interior of the balloon for inflation of the interior of the balloon with the first inflation medium. In some embodiments, the interior comprises a plurality of inflatable chambers. In some embodiments, a first chamber of the plurality of individually inflatable chambers is adapted to be inflated with the first inflation medium, and a second chamber of the plurality of individually inflatable chambers is adapted to be inflated with a second inflation medium. In some embodiments, the first inflation medium imparts at least one of rigidity in the implant and cushion in the implant.

In some embodiments, the implant comprises a second appendage coupling the balloon to at least one of: the femur of the joint and the tibia of the joint. In some embodiments, the implant comprises at least one attachment element in the intercondylar notch. The In some embodiments, the implant comprises at least one attachment element superiorly at the distal end of the femur anteriorly. In some embodiments, the implant comprises at least one posterior reign configured to cinch up the implant from inside a posterior intercondylar notch toward a connection site around the femur. In some embodiments, the implant comprises at least one suture-like lanyard configured to cinch up the implant from inside a posterior intercondylar notch toward a connection site around the femur.

In some embodiments, the implant is manufactured as a multilayer structure or laminate, such as a coextruded laminate. In a preferred embodiment, the implant is a single layer or monolayer of polymer. In other embodiments, the implant does not have a balloon or inflatable portion thereof.

Whether the implant is a monolayer or multilayer structure, the layers can be made of for example, BIONATE® (e.g., BIONATE® I, BIONATE® II, BIONATE® 55D, BIONATE® 65D, BIONATE® 75D, BIONATE® 80, BIONATE® 80A, BIONATE® 90A) or one or more layers of Chronoflex (e.g., ChronoFlexAR®, ChronoFlex AL®, ChronoFlec C®).

Provided herein is an implant configured for patch a defect of a bone of a knee joint, the implant comprising a balloon configured to engage the defect of the bone of the knee joint and comprising an interior that is optionally inflatable with a first inflation medium; and a first appendage configured to couple the balloon to the bone of the knee joint.

In some embodiments, at least one of the appendage and the balloon are configured to replace cartilage.

In some embodiments, the balloon is at least one of: at most about 0.5 cm in diameter, at most about 0.75 cm in diameter, at most about 1 cm in diameter, at most about 1.25 cm in diameter, at most about 1.5 cm in diameter, at most about 1.75 cm in diameter, at most about 2 cm in diameter, at most about 2.25 cm in diameter, at most about 2.5 cm in diameter, at most about 2.75 cm in diameter, at most about 3 cm in diameter, at most about 3.25 cm in diameter, at most about 3.5 cm in diameter, at most about 3.75 cm in diameter, at most about 0.5 cm in length along the longest length of the balloon, at most about 0.75 cm in length along the longest length of the balloon, at most about 1 cm in length along the longest length of the balloon, at most about 1.25 cm in length along the longest length of the balloon, at most about 1.5 cm in length along the longest length of the balloon, at most about 1.75 cm in length along the longest length of the balloon, at most about 2 cm in length along the longest length of the balloon, at most about 2.25 cm in length along the longest length of the balloon, at most about 2.5 cm in length along the longest length of the balloon, at most about 2.75 cm in length along the longest length of the balloon, at most about 3 cm in length along the longest length of the balloon, at most about 3.25 cm in length along the longest length of the balloon, at most about 3.5 cm in length along the longest length of the balloon, at most about 3.75 cm in length along the longest length of the balloon, and at most about 4 cm in length along the longest length of the balloon.

In some embodiments, the size of the balloon size is pre-set. In some embodiments, the balloon comprises multiple chambers which may be selectively inflated. In some embodiments, the balloon comprises multiple chambers which may be selectively deflated. In some embodiments, the balloon comprises multiple chambers which may be selectively inflated in situ to fill the defect. In some embodiments, the balloon comprises multiple chambers which may be selectively inflated just prior to implantation.

In some embodiments, the balloon or a chamber thereof may be secondarily inflated, deflated, or a combination thereof in situ.

In some embodiments, the implant comprises an ingrowth matrix on at least a portion of the implant adjacent the femur. In some embodiments, the ingrowth matrix comprises living chondrocytes. In some embodiments, the implant is configured to release the chondrocytes over time. In some embodiments, the implant comprises a bioabsorbable polymer configured to release the chondrocytes over time. In some embodiments, the implant comprises a polymer configured to release the chondrocytes over time, wherein the polymer is not bioabsorbable. In some embodiments, the ingrowth matrix comprises at least one of: autologous cells, allograph cells, and xenograph cells to restore an articular surface of the femur. In some embodiments, the ingrowth matrix comprises at least one of: autologous cells, allograph cells, and xenograph cells to repair an articular surface of the femur.

In some embodiments, the implant comprises couplers that couple the appendage to the femur. In some embodiments, the coupler is bioabsorbable. In some embodiments, the coupler is at least one of: a screw, a washer, a suture, a suture anchor, a rivot, a staple, a staple having teeth, a stabilizer, a glue, a hook, a wire, a string, a lasso, a lanyard, a spike, and combinations thereof. The implant may also and/or alternatively be attached via bone ingrowth.

In some embodiments, the implant comprises a phamacologic agent. In some embodiments, the pharmacologic agent is on a surface of the implant adjacent the femur. In some embodiments, the pharmacologic agent is released from the implant over time. In some embodiments, the pharmacologic agent is released from within the implant over time. In some embodiments, the pharmacologic agent is released from within the balloon over time.

In some embodiments, the inflation medium is compressible. In some embodiments, the inflation medium comprises a viscolubricant. In some embodiments, the inflation medium comprises an NSAID. In some embodiments, the inflation medium comprises chondrocytes.

In some embodiments, at least a portion of the implant is configured to anneal to a periphery of a cartilage defect.

In some embodiments, the implant comprises vacuoles of pharmacologic substances. In some embodiments, the vacuoles may be on a bone-engaging portion of the implant. In some embodiments, the implant comprises bubbles comprising an active substance such as a pharmacologic substance or other active agent. In some embodiments, the active agent comprises at least one of: stem cells, growth factors, antibiotics, and viscolubricants. In some embodiments, the active agent comprises iatrigenically gene mutated cells.

In some embodiments, the implant comprises enzyme absorptive microscopic sponges that could be sucked out or evacuated at or around the time of implant delivery to the joint.

In some embodiments, the implant comprises spaces filled with an active substance such as a pharmacologic substance or other active substance. In some embodiments, the implant is configured to deliver by dissolution of the implant material In some embodiments, the implant is configured to deliver by release through pores of the implant. In some embodiments, the implant is configured to deliver by fracture of a vacuole by a catalyst such as ultrasound or pressure or other fracturing catalyst.

In some embodiments, the implant is configured to at least one of: pad cartilage, cushion the joint, deliver a pharmacologic substance, remove noxious enzymes, debride upon implantation, debride the joint following implantation, deliver a therapeutic substance, deliver a biologic substance, and deliver living stem cells. In some embodiments, the implant is configured to deliver a chemotherapeutic agent to a bone or other surrounding tissues. In some embodiments, the implant is configured to deliver an anti-infectious medication to a bone or other surrounding tissues. In some embodiments, the implant is configured to deliver at least one of an antibiotic, antifungals, and analgesics agent.

In some embodiments, the implant is configured to be selectively inflated to realign limbs.

Provided herein is a method comprising: implanting a knee implant as described herein into a subject, wherein the implant reverses arthritis in the subject.

Provided herein is a method comprising: implanting a knee implant as described herein into a knee joint of a subject and treating a component of the knee joint of the subject with at least one of an allograph tissue, an autograph tissue, and an xenograph tissue. In some embodiments, the implanting step is at least one of: prior to the treating step, simultaneous with the treating step, and following the treating step.

Provided herein is a method comprising: implanting a knee implant as described herein into a subject, wherein the implant at least one of: restores joint function and controls arthopathies. In some embodiments, the implanting spares existing anatomy.

Provided herein is a method comprising: debriding a femur condyle of a knee joint of a subject, and implanting a knee implant as described herein into the knee joint of the subject, whereby the implant is configured to anneal to the cartilage of the subject. In some embodiments, the debriding is achieved by steam application.

Provided herein is a method comprising implanting a knee implant as described herein into a joint previously treated with a joint replacement. In some embodiments, the method comprises removing the joint replacement prior to implanting the knee implant. In some embodiments, the method comprises clearing infectious matter from the joint and/or surrounding tissues. In some embodiments, the method comprises implanting a second implant of any implant described herein following removing the implant previously implanted in the joint. In some embodiments, the method comprises replacing the joint of the subject following removing the implant previously implanted in the joint. In some embodiments, the method comprises debriding the bone of the joint, and implanting an implant of any implant described herein. In some embodiments, the method comprises repeating the debriding and implanting steps.

These and other advantages of the invention will become more apparent from the following detailed description and the attached exemplary drawings.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 13A-13D depict multiple views of a staple adapted to couple an implant to a bone of the joint.

FIG. 14 depicts an embodiment of the knee implant having appendages including holes and tabs and including slots to accommodate ligaments of the knee joint as well as side views of the same knee implant.

DETAILED DESCRIPTION OF THE INVENTION

Figure 1:
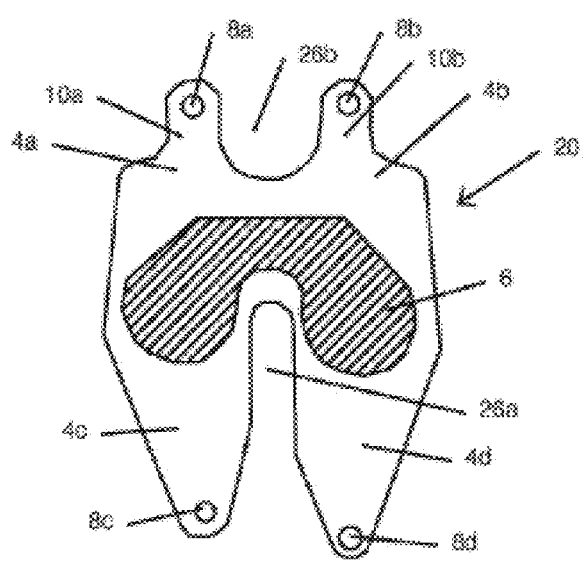
FIG. 1 depicts an embodiment of the knee implant having appendages including holes and tabs extending from a balloon and including slots to accommodate ligaments of the knee joint.

The present invention is directed to arthroplasty implants and procedures for a wide variety of joints such as, for example, hips, knees, shoulders, ankles, elbows, wrists, fingers, toes, temporomandibular joints and the like, but for clarity, as well as brevity, the discussion herein will focus on an implant for a knee joint or hip joint and an implant for replacing the talus bone of a patient's ankle.

Knee interpositional arthroplasty can replace existing total joint metal/plastic technology. It intends to fill the gap (literally in some embodiments of the implant) in cases where arthroscopic debridement fails to provide cure, since we can only 'polish arthritis' and 'clean up the joints' to date. The polymer medically inflatable implants may physiologically restore joint function. Padding is provided where cartilage is damaged, cushioning to both the femoral tibial and patella femoral joints when narrowed or pathologic. The implant in some embodiments is adapted to deliver cells, autologous (from the patient), allograph (from another member of the same species) or xenograph (from another species) that restore articular surfaces. Since cartilage is an immunologically privileged tissue, the antigens are buried in the cartilage matrix and antibodies do not reject the refurbished surface coating.

The gap (or gaps) filled by the balloon or balloons of the implant will provide compliance between opposing joint surfaces (the femoral condyle or condyles and tibial plateau). The femur may have some portion (of not all) of the retropatellar rounded facet "V" shape of hyaline, normally about 5 mm thick, or it may not have such hyaline when the implant is inserted. The tibial plateau may have some portion of meniscal fibrocartilages, including all of said fibrocartilages, none of said fibrocartilages, or some portion thereof. When the knee is extended (straight) the implant buffers the femoro-tibial joint. When the knee is flexed, the implant balloon apposition is more between the trochlear groove portion of the anterior distal femur (groove between the condyles on the 'front of the knee') and the patella.

The knee anatomy is unique to other joint anatomies and thus has a unique set of challenges that are addressed by the implant embodiments described herein. For example, the knee is not a ball and socket joint like a hip; it is a combination of two joints—the femoral-tibial joint and the patellar-femoral joint. The bones of the knee have facets and irregularities that must be accommodated by a conformable implant directed to the particular shapes of the bones without impeding the joints' functions and movements, and/or which minimizes impedance to such function and movement. Not only do the joints of the knee work together to allow extension and flexion of the knee, but the knee is also designed to allow rotational movement in a screw-like manner. That is, as the tibia is twisted relative to the femur, the joints are uniquely designed to allow this twist, but to limit the twist as well. Furthermore, the knee joints are able to withstand forces that vary depending on the particular movement of the individual, not only in force strength, but in direction as well. Thus, the implants as described herein are uniquely designed to account for these factors and result in a knee having preserved natural tissues as well as preserved function and movement as compared to typical arthroplasty procedures (such as partial or full knee replacements).

As described herein, embodiments of the implant conform to the patient's own joint features not only in that it can be pre-molded and/or adapted to couple to the contours of the patient's bone (condyle, etc), but in that it has a balloon having an inflation medium that is conformable to the joint anatomy and allow freedom of joint movement much like natural joint while preserving the joint and bone natural tissues as much as possible. With the ability to fill various chambers of the balloon with varying materials, and to add rigid and/or semi-rigid pieces to the implant, the implant can additionally have leveling capabilities and alignment capabilities.

Diagnoses:

Patients may complain of pain and knee joint dysfunction signaled by locking, clicking, or giving way. Knees may be swollen, malaligned or show crepitus (palpable crunching on movement.) Instability of ligaments whether anterior/posterior cruciates, or medial/lateral conlaterals, are treated by techniques separate for those entities via allowance for healing (as for collaterals) or via cruciate repair or reconstruction.

Indications for use of implants provided herein may be those patients recognizing greater than or equal to 2 Sq cm of 3-4+/4 traumatic arthritis (ala Carticel or MACI). In such cases, the cartilage defect is often precisely locally symptomatic, with point tenderness, clicking if a loose cartilage flap exists, and may be visible on MRI and/or arthroscopic inspection and/or through palpation. The implants used herein may additionally and/or alternatively be appropriate when existed techniques such as 'picking', K wire drills, and/or allograph implants fail.

Patients with knee problems typically complain of pain and dysfunction. Pathognomonic symptoms for meniscal tearing include locking, clicking, giving way from wear or twisting the knee. Aching diffusely may arise from arthritis or synovitis; anterior knee pain is generally patella-femoral, increased with stair use due to magnified body weight forces. Diagnosis should be accurate as distinguished from pain through the knee actually arising in the back caused by L4 nerve root irritation. Physical Exam findings of pathologic knees include observed swelling, redness, or deformity. Palpation often aids focus on which compartments are involved. The patella inhibition test position connotes retropatellar pathology, and often tracking problems that warrant soft tissue or boney correct. Improved limb alignment will increase benefits, and can in part accrue from selective inflation of embodiments of the implants provided herein. X-rays of the knee are best evaluated in weight bearing views, and should be coupled with other data including MRI or CT. Relative compartment narrowing suggests cartilage degradation. Once an embodiment of an implant described herein has been successfully implanted and the knee adequately rehabilitated, the appearance of a knee with such implant should resemble a normal joint X-ray. Knee distension is from saline and/or air insufflation. Knee implant patients will benefit from tailored rehab programs, cautious weight bearing, early motion, and potential the use of constant passive motion machine regimens.

General Features

Implant Aspects

Provided herein is a resilient implant for implantation into knee joints to act as a cushion allowing for renewed joint motion. The implant may endure variable knee joint forces and cyclic loads while reducing pain and improving function after injury or disease to repair, reconstruct, and regenerate joint integrity. The implant may be deployed in a prepared debrided knee joint space, secured to at least one of the knee joint bones and expanded in the space, molding to surrounding structures with sufficient stability to avoid extrusion or dislocation. The implant may have has opposing walls that move in varied directions, and an inner space filled with suitable filler to accommodate motions which mimic or approximate normal knee joint motion. The implant may pad the damaged joint surfaces, restores cushioning immediately and may be employed to restore cartilage to normal by delivering regenerative cells.

Provided herein is a resilient interpositional arthroplasty implant for application into knee joints to pad cartilage defects, cushion joints, and replace or restore the articular surface, preserving joint integrity, reducing pain and improving function. The implant may endure variable knee joint compressive and shear forces, and millions of cyclic loads, after injury or disease requires intervention. The implant may repair, reconstruct, and regenerate knee joint anatomy in a minimally morbid fashion, with physiologic solutions that improve upon the rigid existing joint replacement alternatives of plastic and metal. In cases where cells have been used for joint resurfacing requiring massive periosteal harvesting for containment, the polymer walls of some embodiments of the implant can capture, distribute and hold living cells until aggregation and hyaline cartilage regrowth occurs. The implant may be deployed into a prepared debrided knee joint space, molding and conforming to surrounding structures with sufficient stability to avoid extrusion or dislocation. Appendages (or tabs) of the implant may serve to repair or reconstruct tendons or ligaments. The implant may have opposing walls that move in varied directions, and an inner space, singular or divided, filled with suitable gas, liquid, and/or complex polymer layers as force-absorbing mobile constituents, such than robust valid and reliable joint motion is enabled.

Provided herein is a resilient orthopedic implant configured for deployment between a femur and at least one second bone of a joint. The second bone may be a tibia. The second bone may be a patella. The implant further comprises a balloon comprising a first portion that is configured to engage the femur, a second portion that is configured to engage the second bone of the joint, a side portion connecting the first portion and the second portion, in which the side portion facilitates relative motion between the first portion and the second portion, and an interior that is optionally inflatable with a first inflation medium; and a first appendage configured to couple the balloon to the femur. The terms "balloon" and "bladder" may be used interchangeably throughout this disclosure to describe an implant having the features described herein.

In some embodiments, at least two of the first portion, the second portion, and the side portion are contiguous. In some embodiments, the first portion comprises a first wall, the second portion comprises a second wall, and the side portion comprises a side wall. As used herein, each of the terms the "first portion", the "second portion", and the "side portion" is used to describe a part of the balloon, and may not be separate parts in some embodiments. Rather, in some embodiments, each is named in order to indicate the general geometry and location of each portion relative to the other of the portions and/or relative to bones and/or ligaments and/or tendons of the joint. Likewise, as used herein, each of the terms the "first wall", the "second wall", and the "side wall" is used to describe a part of the balloon, and may not be separate parts of the balloon in some embodiments. Rather, in some embodiments, each of the walls is named in order to indicate the general geometry and location of each portion relative to the other of the portions and/or relative to bones and/or ligaments and/or tendons of the joint. In some embodiments, at least two of first wall, the second wall, and the side wall are contiguous. Nevertheless, each of the walls may, in some embodiments, be separate parts of the implant that are joined to form the implant. Likewise, each of the portions may, indeed, in some embodiments, be separate parts of the implant that are joined to form the implant.

In some embodiments, the first portion is a term used interchangeably with the first wall. In some embodiments, the second portion is a term used interchangeably with the second wall. In some embodiments, the side portion is a term used interchangeably with the side wall. In some embodiments, a wall (whether a first wall, a second wall, and/or a side wall) of the implant may comprise a plurality of layers. The wall may comprise multiple materials to impart physical and/or therapeutic characteristics to the wall.

In some embodiments, the implant comprises a second appendage coupling the balloon to the first bone of the joint. In some embodiments, the implant comprises a second appendage coupling the balloon to at least one second bone of the joint. In some embodiments, the implant comprises a second appendage configured to couple at least one of the first portion, the second portion, and the side portion to at least one of the first bone and at least one second bone of the joint. In some embodiments, the first appendage and the second appendage are configured to provide ligamentary-like support to the first bone and the at least one second bone of the joint. In some embodiments, the first appendage and the second appendage are configured to provide ligamentary-like support to the joint. In some embodiments, the first appendage and the second appendage are configured to provide tendon-like support to the first bone and the at least one second bone of the joint. In some embodiments, the first appendage and the second appendage are configured to provide tendon-like support to the joint.

In some embodiments, the implant comprises an inflation port in communication with the interior of the balloon for inflation of the interior of the balloon with the first inflation medium. In some embodiments, the balloon is punctured to inflate the interior of the balloon with the first inflation medium. In some embodiments, the balloon is self-sealing. In some embodiments, the balloon is self-sealing upon inflation of the interior of the balloon with the first inflation medium. In some embodiments, the implant comprises a seal capable of closing the interior of the balloon.

In some embodiments, the interior comprises a plurality of inflatable chambers. In some embodiments, the interior comprises a plurality of individually inflatable chambers. In some embodiments, a first chamber of the plurality of individually inflatable chambers is adapted to be inflated with the first inflation medium, and a second chamber of the plurality of individually inflatable chambers is adapted to be inflated with a second inflation medium.

In some embodiments, the interior comprises a honeycomb structure. In some embodiments, the interior comprises a mesh structure. In some embodiments, the interior comprises a sponge structure.

In many embodiments the implant (or a portion thereof, such as the balloon or balloons) is a weight bearing spacer that will allow joint motions to approach normal, whether filling the space left by an entirely collapsed joint bone or the space of ablated cartilage proximate surfaces diffusely as in osteoarthritis or succinctly as in osteonecrotic defects or localized trauma. The walls of the implant may be used as a membrane for holding living cells in proximity of the osteochondral defect long enough for the cells to attach (e.g. 24 hours) or to deeply adhere (up to 28 days) or return to normal (up to one year). Weight bearing will be expected to increase as distal lower extremity joints are treated.

Figure 9A:
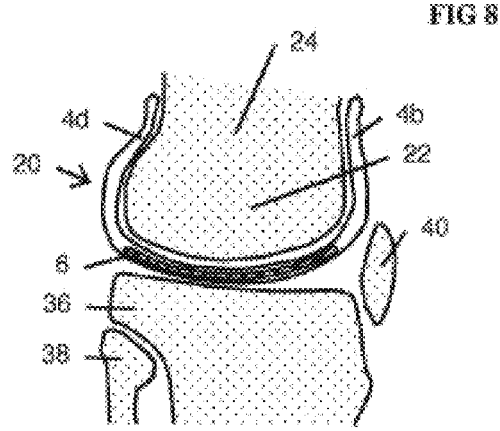
FIG. 9A depicts a side view of an embodiment of the knee implant curved about at least one condyle of a femur, the implant having appendages extending from an uninflated or minimally inflated balloon.
Figure 9B:
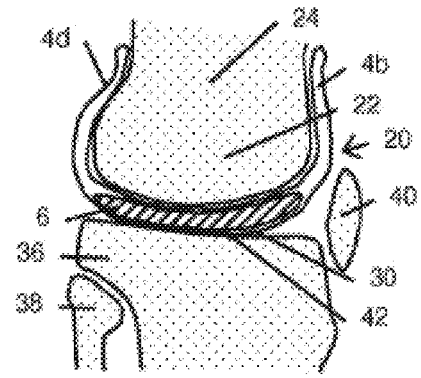
FIG. 9B depicts a side view of an embodiment of the knee implant curved about at least one condyle of a femur, the implant having appendages extending from an inflated balloon.
Figure 9C:
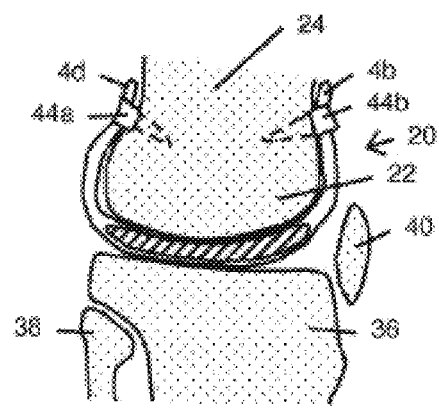
FIG. 9C depicts a side view of an embodiment of the knee implant curved about at least one condyle of a femur, the implant having appendages extending from an inflated balloon and having staples or screws coupling the appendages to the femur.
Figure 10A:
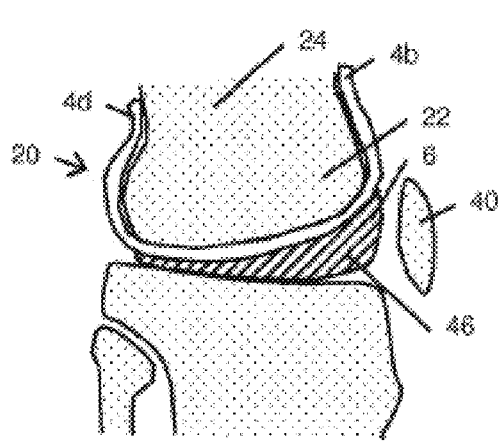
FIG. 10A depicts a side view of an embodiment of the knee implant curved about at least one condyle of a femur, the implant having appendages extending from an inflated balloon and showing the inflation medium moved anteriorly toward the patella when the knee joint is flexed.
Figure 10B:
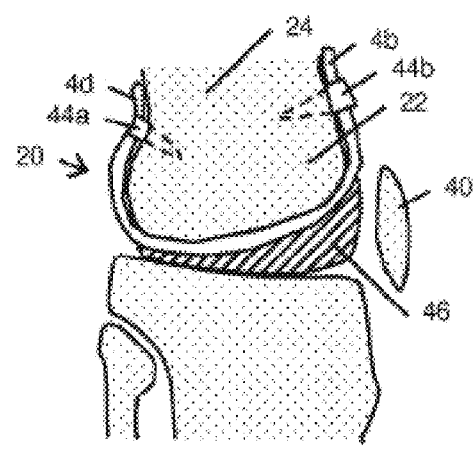
FIG. 10B depicts a side view of an embodiment of the knee implant curved about at least one condyle of a femur, the implant having appendages extending from an inflated balloon and having staples or screws coupling the appendages to the femur and showing the inflation medium moved anteriorly toward the patella when the knee joint is flexed.

Movement (whether linear or curvilinear) between the first and second walls of the implant (i.e. of the balloon) as a result of movement of the femur and the tibia is illustrated in the comparison between FIGS. 9B and 10A, or in the comparison between FIGS. 9C and 10B. In some embodiments, the implant may comprise a balloon that is configured to allow a wall of the implant rolling upon another wall (or the same wall) of the implant (e.g. the side wall rolling upon the first wall, the first wall rolling upon the second wall, the second wall rolling upon the first wall, the first wall rolling upon the side wall, the second wall rolling upon the side wall, the side wall rolling upon the second wall, the first wall rolling upon the first wall, the second wall rolling upon the second wall, and/or the side wall rolling upon the side wall). In some embodiments, the implant may comprise a balloon that is configured to allow a portion of the implant rolling upon another portion (or the same portion) of the implant (for non-limiting example, the side wall rolling upon an appendage, the first wall rolling upon an appendage, and/or the second wall rolling upon an appendage). In some embodiments, the implant may comprise a balloon that is configured to allow movement of a portion of the implant rolling upon cartilage. While not shown in the drawings, there may be slippage between the a portion of the implant (whether an appendage, a wall, or some other portion of the implant) and a joint component (whether a bone, ligament, tendon or other tissue). This slippage may be in addition to wall movements within the implant per se to provide desired joint movements. While not shown in the drawings, there may be slippage between the second bone (for example, the tibia) and the second wall in addition to wall movements within the implant per se to provide desired joint movements. The appendage (or appendages) is (are) designed to secure the implant to the knee joint structure so as to avoid dislocation of the implant. Movement of the joint with the implant in place will be a shared function of both the moving opposing walls of the implant but also a function of the movement of the wall which may be less attached to the joint members. There may be slight movement between the appendage, first wall and the femur. The walls of the balloon may compress and/or stretch to accommodate bone interface movement. Material choices, material dimensions, and implant dimensions, placement and/or coupling may be chosen to allow for the desired amount of compression, stretching relative movement of various joint and/or implant components. For non-limiting example, the walls of the implant may be thicker is some areas to accommodate particular loads and the side wall may be thinner and more elastic to accommodate rolling and stretching thereof.

Motion is believed to be primarily between the spaced walls (or portions) of the implant peripherally secured to joint structures, although some motion may occur between the implant and the joint surfaces. As shown multiple Figures (including, FIGS. 1-7), the implant may be provided with a slot extending from the periphery of the implant toward the balloon of the implant to accommodate at least one ligament of the joint. Knee implants may have two slots leading to separate passages for receiving the anterior and posterior cruciate ligaments. Implant walls should have sufficient inherent flexibility to mold to the existing deformities imposed by either natural ligament, bone, tendon and remaining cartilage deformities of the internal joint space filled as a cushion. The wall exteriors may be flat or formed with random or specific patterns for purposes of glide or trends for traction against adjacent surfaces, or as sulci or venues for cell delivery materials.

The exterior of the implant may have a mesh material with a plurality of chords (or appendages) for securing the implant to adjacent bones or to remnant ligaments which are attached to adjacent bones.

The dimensions of the various implant walls will vary depending upon the material properties thereof as well as the needs for a particular joint. Additionally, the first and second walls may require a thickness different from the side wall. Generally, the implant may have a wall thicknesses of about 0.125 mm to about 3 mm, preferably about 0.5 mm to about 1.5 mm. The spacing between the first and second wall within the interior can vary from about 0.5 mm to about 5 mm.

Figure 11A:
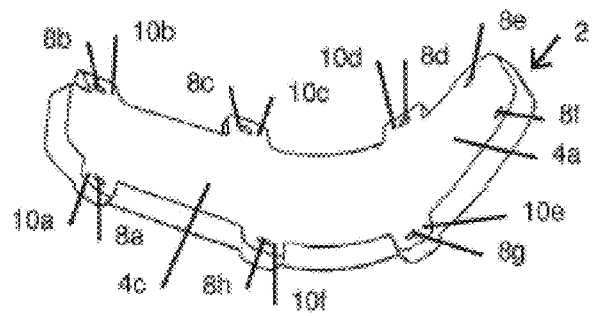
FIG. 11A depicts an embodiment of the unicompartment knee implant curved to simulate curvature about one condyle of a femur, the implant having appendages extending from an uninflated balloon (not shown) and including tabs and holes which may be used with couplers to couple the implant to the femur of the knee joint.
Figure 11B:
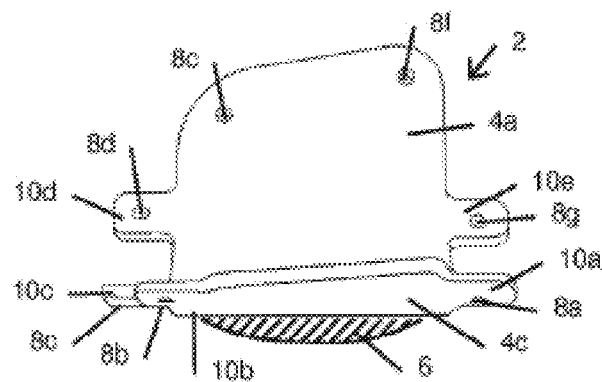
FIG. 11B depicts an embodiment of the unicompartment knee implant curved to simulate curvature about one condyle of a femur, the implant having appendages extending from an inflated balloon and including tabs and holes which may be used with couplers to couple the implant to the femur of the knee joint.
Figure 11C:
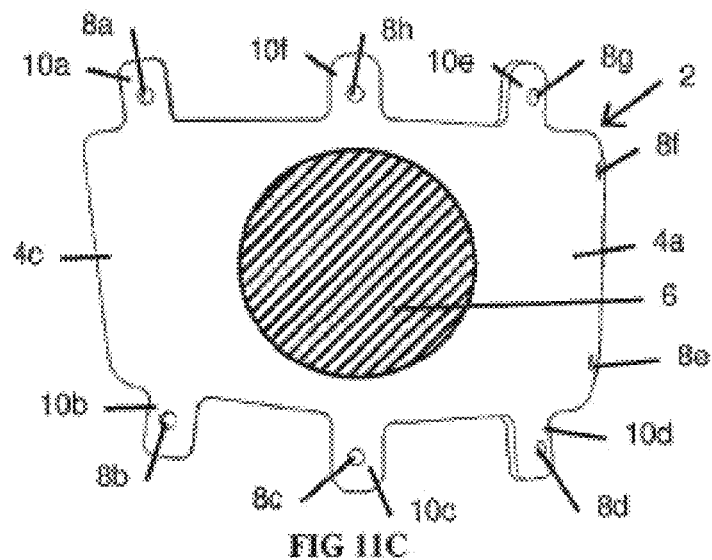
FIG. 11C depicts a bottom-up view of an embodiment of the unicompartment knee implant curved to simulate curvature about one condyle of a femur, the implant having appendages extending from an inflated balloon and including tabs and holes which may be used with couplers to couple the implant to the femur of the knee joint.
Figure 12A:
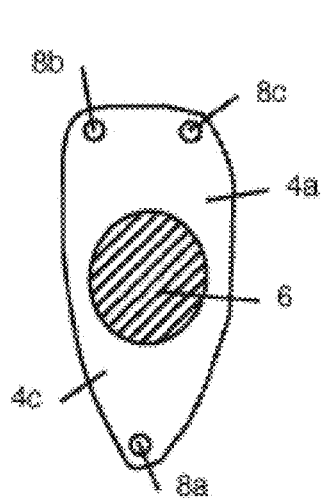
FIG. 12A depicts a bottom-up view of an embodiment of the unicompartment knee implant or patch implant, the implant having appendages, extending from a balloon and including holes, which may be used with couplers (not shown) to couple the implant to the femur of the knee joint.
Figure 12B:
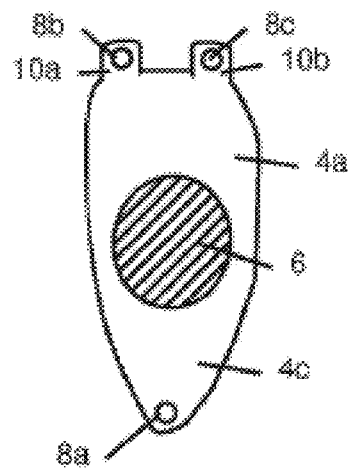
FIG. 12B depicts a bottom-up view of an embodiment of the unicompartment knee implant or patch implant, the implant having appendages, extending from a balloon and including tabs and a hole which may be used with couplers (not shown) to couple the implant to the femur of the knee joint.
Figure 12C:
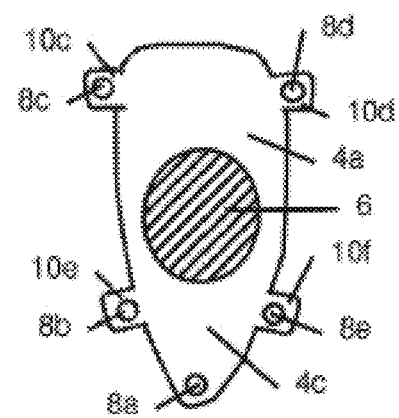
FIG. 12C depicts a bottom-up view of an embodiment of the unicompartment knee implant or patch implant, the implant having appendages, extending from a balloon and including tabs and a hole which may be used with couplers (not shown) to couple the implant to the femur of the knee joint.

In some embodiments, the implant has a first wall, a second wall, and a side wall which define the implant interior (or interior) which contains filling material. In some embodiments, the filling material is an inflation medium. The first wall is secured to the end of the femur by at least one appendage that extends from the first wall and the second wall engages the end surface of the second bone (which in the case of a femoral-tibial joint implant, would be the tibia) and may also be secured thereto. The side wall extending between the first and second walls defines at least in part the implant interior which is filled with filling material (or an inflation medium). The inner surfaces of wall and appendage may conform to the particular surface femur, for example by being wider in particular locations and/or longer in particular areas. For example a dual compartment implant (described herein) may have a wider section to cover the medial condyle than the lateral condyle (as shown in FIGS. 1, 2, 3, 6A, 6B, and 7). In another example, the length of the implant the along the external edge may be longer than the length of the implant along the trochlear groove edge (as shown in FIGS. 11A, 11B and 11C). In yet another example, the width may vary along a single condyle, such as is shown in FIGS. 12A-12C, wherein the wider edge of the implant is adapted to fit over at least a portion of the anterior condyle, and the narrower portion is adapted to fit over at least a portion of the posterior condyle. In some embodiments, the inner surfaces of the first wall and appendages preferably conform to the particular surface of the patient's femur, and do so by not only dimensions of the implant (lengths, widths, balloon location and shape), but also and/or alternatively due to appendage and/or tab and/or hole and/or coupler location and/or surface contours of the first wall. The outer surface of the second wall may be configured to conform to the end surface of the second bone (which may be a tibia or a patella, for example). In some embodiments, the outer surface of the second wall is configured to conform to a surface of the second bone (which may be a tibia or a patella, for example). The figures provided herein are highly schematic and do not depict details of the joint surface features, since human pathology and variation reflects both the patient's immediate and evolving pathophysiology. Neither do the figures depict other joint features such as cartilage, tendons, ligaments and other soft tissues and fluids of the joint for ease of viewing that which is depicted.

In some embodiments, the implant is configured to resemble the shape of the natural hyaline of a normal knee. For example, the normal hyaline is typically "H" shaped, thus certain embodiments of the implant are generally "H" shaped.

Implant Materials and Material Features

In some embodiments, the implant comprises polymer. Polymers may comprise at least one of: a polyurethane (such as, for example, ChronoFlex AR), a polycarbonate urethane, a thermoplastic polycarbonate urethane (such as Bionate 55, Bionate®80, Bionate®80A), ethylene-vinyl acetate copolymer, multiblock copolymers of poly(ethylene oxide) (PEO) and poly(butylene terephthalate) (PBT), PEG, PEO, and a polyetheylene. In some embodiments the implant comprises a 125 micron thickness thermoplastic polycarbonate urethane.

The implant may comprise to a plurality of layers of polymer (such as ChronoFlex AR) in a solvent and evaporating the solvent after applying each layer. In some embodiments, the implant comprises a polyurethane that is sprayed and dried (wherein the spraying and drying is repeated at least once) to a desired thickness.

In some embodiments, the implant comprises polymer. Polymers may comprise at least one of: a polyurethane (such as, for example, ChronoFlex AR, ChronoFlex AL®, ChronoFlec C®), a polycarbonate urethane, a thermoplastic polycarbonate urethane (such as BIONATE®, e.g., BIONATE® I, BIONATE® II, BIONATE® 55D, BIONATE® 65D, BIONATE® 75D, BIONATE® 80A, BIONATE® 90A, BIONATE® 55 or BIONATE® 80), ethylene-vinyl acetate copolymer, multiblock copolymers of poly(ethylene oxide) (PEO) and poly(butylene terephthalate) (PBT), PEG, PEO, and a polyetheylene.

The implant may comprise to a plurality of layers of polymer (such as ChronoFlex AR, ChronoFlexAR®, ChronoFlex AL®), ChronoFlec C®) in a solvent and evaporating the solvent after applying each layer. In some embodiments, the implant comprises a polyurethane that is sprayed and dried (wherein the spraying and drying is repeated at least once) to a desired thickness.

The implant may be formed of suitable bioabsorbable materials so that the implant may be absorbed within a particular predetermined time frame. Suitable bioabsorbable materials include polylactic acid, polyglycolic acid, polycaprolactone, copolymers, blends and variants thereof. Suitable bioabsorbable materials may also/alternatively include poly(hydroxyalkanoate)s of the PHB-PHV class, additional poly(ester)s, and natural polymers, particularly, modified poly(saccharide)s, e.g., starch, cellulose, and chitosan. The walls of the implant may be (in whole and/or in part) bioabsorbable. The balloon may be (in whole and/or in part) bioabsorbable. As used herein the terms bioabsorbable, bioerodable, and/or bioabsorbable may be used interchangeably. The walls of the implant may release a pharmaceutical agent or an biological agent (such as stem cells, differentiated cells, pluripotent cells, post-mitotic cells, living chondrocytes, gene therapies, and the like). The release of such agents (whether biological or pharmaceutical, or a combination thereof) may occur over time, as the wall of the implant (or as the balloon) bioabsorbs in some embodiments, or as the joint is used (i.e. through pressure, for non-limiting example). In some embodiments, at least one of the implant walls is permeable to a pharmaceutical agent and/or a biological agent, such as in an embodiment wherein the inflation medium comprises the pharmaceutical agent and/or biological agent. In some embodiments, at least one of the implant walls has pores through which the pharmaceutical agent and/or the biological agent may fit, such as in an embodiment wherein the inflation medium comprises the pharmaceutical agent and/or biological agent. In some embodiments the contents may contain targeting drugs such as gleevac that turn off tumor molecules as those in GIST. Cell-specific drugs targeting tumors by design may require nano-sized micelles with hydrophilic shells to protect core agents. In some embodiment hydrogels are used and tailored to swell thus releasing trapped molecules or cells through weblike surfaces, controlled by internal or external triggers such as ph, magnetic fields, or temperature. Dendritic macromolecules may be used in implants to deliver agents en masse deploying a controllable size and structure. In some embodiments, individual agent molecules or hubs may be incorporated via covalent bonds.

In some embodiments, the implant is created by dip molding a mandrel having a shape of a bone of the knee joint (the medial condyle, the lateral condyle, the tibia, for non-limiting example) into a polymer solution (for non-limiting example, a urethane polymer such as Chronoflex). Following each dip, the implant is dried for a specified time, which may be, for example, about 3 seconds, about 4 seconds, about 5 seconds, about 6 seconds, about 7 seconds, about 8 seconds, about 9 seconds, about 10 seconds, about 15 seconds, about 20 seconds, about 25 seconds, about 30 seconds, about 45 seconds, about 1 minute, about 2 minutes, about 5 minutes, about 10 minutes, about 15 minutes, and over about 15 minutes. The term "about" used herein in reference to drying time of the implant can mean variations of at least one of 5%, 10%, 25%, and 50%, In some embodiments, no drying step is used. The dipping may be repeated multiple times. In some embodiments a single dip is sufficient. In some embodiments, the dipping is repeated 2 times. In some embodiments, the dipping is repeated 3 times. In some embodiments, the dipping is repeated 4 times. In some embodiments, the dipping is repeated 5 times. In some embodiments, the dipping is repeated 6 times. In some embodiments, the dipping is repeated 7 times. In some embodiments, the dipping is repeated 8 times. In some embodiments, the dipping is repeated 9 times. In some embodiments, the dipping is repeated 10 times. In some embodiments, the dipping is repeated 11 times. In some embodiments, the dipping is repeated 12 times. In some embodiments, the dipping is repeated 13 times. In some embodiments, the dipping is repeated 14 times. In some embodiments, the dipping is repeated 15 times. In some embodiments, the dipping is repeated 16 times. In some embodiments, the dipping is repeated 17 times. In some embodiments, the dipping is repeated 18 times. In some embodiments, the dipping is repeated 19 times. In some embodiments, the dipping is repeated 20 times. In some embodiments, the dipping is repeated 21 times. In some embodiments, the dipping is repeated 22 times. In some embodiments, the dipping is repeated 23 times. In some embodiments, the dipping is repeated 24 times. In some embodiments, the dipping is repeated 25 times. In some embodiments, the dipping is repeated over 25 times. In some embodiments, the dipping is repeated a sufficient number of times to create an implant that is a prescribed thickness. The thickness may vary depending on the polymer and depending on the embodiment of the implant. The thickness may be at least one of: about 25 microns thick, about 50 microns thick, about 100 microns thick, about 125 microns thick, about 150 microns thick, about 200 microns thick, about 250 microns thick, about 300 microns thick, about 350 microns thick, about 400 microns thick, about 25-50 microns thick, about 50-100 microns thick, about 50-200 microns thick, about 100-150 microns thick, about 150-300 microns thick, about 100-300 microns thick, about 100-500 microns thick, about 200-500 microns thick, and about 200-1000 microns thick. The term "about" used herein in reference to thickness of the implant can mean variations of at least one of 5%, 10%, 25%, and 50%, The thickness may vary at different locations of the implant. In some embodiments, the implant is fabricated in two pieces, one or more of which is molded to form an interior when the two pieces are put together. In some embodiments, the implant is filled by puncturing the implant wall and sealing the puncture hole with a plug, patch or other sealant. The plug, patch, or other sealant may comprise Chronoflex material, for non-limiting example. The plug, patch, or other sealant may comprise the same material from which the implant is constructed, for non-limiting example.

The walls of the implant embodying features of the invention may be composite structures. For example, the innermost layer may be impervious to preclude escape of inflation or other filling media, a central layer may be porous or otherwise contain treatment or cell regeneration agents, and the outer layer may be a thin, but strong layer of a thermoplastic, such as a thermoplastic polyurethane for non-limiting example, which has microporosity sufficient to allow passage or egress of treatment or cell regeneration agents from the central layer (or second layer). The degree of microporosity to enable egress of treatment or cell regeneration agents from the central layer is found in polymer layers such as Chronoflex or Bionate 55.

The external wall (and/or the bone engaging surface) of the implant may be coated and/or impregnated with a latticework of polymer that is surface sprayed or layered on the outside (or bone engaging surface) of the implant to promote cartilage tissue regeneration. This most external surface coating may contain living chondrocytes (for example, as is provided in the Carticel procedure by the Genzyme company), and/or may contain stem cells with directed gene mutations to enhance adherence of the coating to the implant. The bone engaging surface may comprise peaks and troughs. The living cells may be imposed in between (and/or provided in the) troughs of the implant surface while the surface areas of prominence (the peaks of the surface) may be used for at least one of: space validation, traction, and cell protection. The bone engaging surface may have a roughness to it or may have a different texture than the articulating surface. The articulating surface may be smooth.

The implant may be formed of suitable bioabsorbable materials so that the implant may be absorbed within a particular predetermined time frame. Suitable bioabsorbable materials include polylactic acid, polyglycolic acid, polycaprolactone, copolymers, blends and variants thereof. Suitable bioabsorbable materials may also/alternatively include poly(hydroxyalkanoate)s of the PHB-PHV class, additional poly(ester)s, and natural polymers, particularly, modified poly(saccharide)s, e.g., starch, cellulose, and chitosan. The walls of the implant may be (in whole and/or in part) bioabsorbable. The balloon may be (in whole and/or in part) bioabsorbable. As used herein the terms bioabsorbable, bioerodable, and/or bioabsorbable may be used interchangeably. The walls of the implant may release a pharmaceutical agent or an biological agent (such as stem cells, living chondrocytes, gene therapies, and the like). The release of such agents (whether biological or pharmaceutical, or a combination thereof) may occur over time, as the wall of the implant (or as the balloon) bioabsorbs in some embodiments, or as the joint is used (i.e. through pressure, for non-limiting example). In some embodiments, at least one of the implant walls is permeable to a pharmaceutical agent and/or a biological agent, such as in an embodiment wherein the inflation medium comprises the pharmaceutical agent and/or biological agent. In some embodiments, at least one of the implant walls has pores through which the pharmaceutical agent and/or the biological agent may fit, such as in an embodiment wherein the inflation medium comprises the pharmaceutical agent and/or biological agent.

The implant may be provided with latticework or other reinforcing strands, preferably on the exterior or within the wall thereof to control the maximum expansion of the implant when deployed at the orthopedic site.

In some embodiments, the implant comprises amniotic membrane (and/or a component thereof). In some embodiments, the implant comprises amniotic sac (and/or a component thereof). In some embodiments, the implant comprises amniotic tissue (and/or a component thereof). Amniotic membrane (and/or sac and/or tissue) is unique in that its mechanical properties include that it slippery on one side (lubricious, low modulus of elasticity) and sticky (adherent) on the other. In some embodiments, at least one of the first wall, the second wall and the side wall comprise amniotic membrane or a component thereof. In some embodiments, at least one of the first wall, the second wall and the side wall comprise amniotic sac or a component thereof. In some embodiments, at least one of the first wall, the second wall and the side wall comprise amniotic tissue or a component thereof. The amniotic membrane and/or amniotic sac and/or amniotic tissue may be used in conjunction with other biologic agents, pharmaceutical agents, and/or therapeutic agents. Amniotic tissue is used extensively in pleuripotential cells. It qualifies as HTBP (Human Tissue Based Product) because of the short term time span on the product and origin.

In some embodiments, the balloon is a composite structure. In some embodiments, the balloon comprises layers of porous and/or non-porous materials, or otherwise contain treatment or cell regeneration agents. In some embodiments, a first layer of the balloon is a thin, but strong layer of a thermoplastic, such as a thermoplastic polyurethane, for non-limiting example, which has microporosity sufficient to allow passage or egress of treatment or cell regeneration agents from a second layer. The second layer may be a central layer (which lies between the first layer and a third layer or a fourth layer or more layers). The first layer may comprise a bone engaging surface in some embodiments. The degree of microporosity to enable egress of treatment or cell regeneration agents from the second layer is found in polymer layers such as Chronoflex or Bionate 55. The bone engaging surface of the implant may be coated and/or impregnated with a latticework of polymer that is surface sprayed or layered on the bone engaging surface of the implant to promote cartilage tissue regeneration. This bone engaging surface coating may contain living chondrocytes (for example, as is provided in the Carticel procedure by the Genzyme company), and/or may contain stem cells with directed gene mutations to enhance adherence of the coating to the implant. The bone engaging surface may comprise peaks and troughs. The living cells may be provided in troughs while the surface peaks may be used for at least one of: space validation, traction, and cell protection.

In some embodiments, the implant is pre-molded to fit about at least one condyle of the femur. In some embodiments, the implant comprises a memory plastic. In some embodiments, the implant comprises a wire frame. In some embodiments, the wire of the wire frame comprises a memory metal. In some embodiments, the memory metal comprises nitinol. In some embodiments, the wire frame is disposed in the periphery of the implant or a portion thereof. In some embodiments, the wire frame is configured to aid in placement against the posterior of the condyle.

In some embodiments, at least a portion of the implant comprises a slippery surface. In some embodiments the slippery surface is configured to allow for relative movement between the implant (or a portion thereof) that is coupled to the femur and the tibia. In some embodiments the slippery surface is configured to allow for relative movement between the implant (or a portion thereof) that is coupled to the femur and the patella.

Inflation Medium and Inflation or Filling of the Implant Interior

In some embodiments, the implant comprises an inflation medium that is compressible. In some embodiments, the implant comprises an inflation medium that comprises a viscolubricant. In some embodiments, the implant comprises an inflation medium that comprises a pharmacologic substance. In some embodiments, the implant comprises an inflation medium that comprises an NSAID. In some embodiments, the implant comprises an inflation medium that comprises chondrocytes. In some embodiments the implant is configured to anneal the outer most layer of the implant (or a portion thereof) to the peripheral of succinct cartilage defects so as to cover them, allowing for healing. In some embodiments the implant is configured to anneal the outer most layer of the implant (or a portion thereof) to the peripheral of succinct cartilage defects so as to cover them, allowing for healing once new chondrocytes have been installed.

The implant interior (balloon interior) may be inflated with gas. The implant interior (balloon interior) may be inflated with liquid. The implant interior (balloon interior) may be inflated with saline. The implant interior (balloon interior) may be inflated with suspended stem cells. The implant interior (balloon interior) may be inflated with gel. The implant interior (balloon interior) may be inflated with a viscolubricant. The inflation medium in some embodiments stays within the balloon, or a portion thereof (as where there are multiple chambers to the balloon). In some embodiments, balloon contents disburse through microporosities and/or dissolving membranes into the joint. In some embodiments, balloon contents disburse by expulsive or evacuation precipitated through an implant wall after pressure from limb use. In some embodiments, balloon contents disburse by expulsive or evacuation precipitated through an implant wall from planned osmosis. In some embodiments, balloon contents disburse by expulsive or evacuation precipitated through an implant wall from vacuole rupture (whether mechanical rupture, ultrasound, or chemical rupture, for non-limiting example). In some embodiments, balloon contents disburse by expulsive or evacuation precipitated through an implant wall thereby distributing contents of the implant interior to joints as lubricious, analgesic, anti-inflammatory and/or otherwise healing substances. In some embodiments, the implant may comprise solid beads or beads containing gel or liquid for sequential disbursement by compressive force through rupture with varied bead wall thicknesses, or the beads may be time-released (opened) chemically, pharmacologically, or by an outside ultrasound or magnetic force external knee application at appropriate clinical intervals. In some embodiments, the implant may comprise vacuoles containing gel or liquid for sequential disbursement by compressive force through rupture with varied vacuole wall thicknesses, or the vacuoles may be time-released (opened) chemically, pharmacologically, or by an outside ultrasound or magnetic force external knee application at appropriate clinical intervals.

The implant interior (or balloon interior) between the first wall and the second wall is filled with filler material (or an inflation medium) which aids in maintaining the desired implant dynamics within the joint structure. The nature of the filler material such as a fluid and the characteristics of the walls may be selected to maintain a desired spacing between the walls in order to accommodate the pressure applied by the bones of the joint structure to the implant and to allow suitable motion between the first and second walls of the implant which facilitate bone motion which mimics or approximates normal movement for the joint members involved.

Alternatively (and/or additionally), the inner chamber (interior or a portion thereof) may be filled with resilient material to provide the desired spacing, pressure accommodation, while allowing desired physiologic motion between implant layers. The implant may be configured to be shaped like the joint space and bone surfaces being replaced or to fill the void produced by injury or disease so that the natural joint spacing and cushioning of the joint interface is restored toward normal physiologic appearance and function. Fluids such as saline, mineral oil and the like may be employed to inflate the implant.

The interior of implant is adjustably filled by the physician from an appropriate source thereof after the implant is deployed to ensure that the pathologic joint space becomes a resilient cushion again which aids restoration of worn or damaged cartilage interfaces in the joint by covering cartilage defects with the implant material, cushioning the joint and defects therein and delivering cell regeneration agents. In one embodiment, the implant comprises a bio-compatible inflatable member (balloon) that is filled with a biocompatible fill material (inflation medium) such as a gas, liquid, gel or slurry, or fluid that becomes a resilient solid to provide relative movement between the first and second walls. The filling or inflation media may be inserted through an injection valve site leading to the cannula which delivers the material into the interior of the implant. In an alternative embodiment, the implant may be filled with or have an interior formed of biologically compatible resilient material, e.g. a closed cell sponge filled with suitable fluid that is inserted into the interior of the implant prior to the implant's deployment or injected into the interior after the implant is deployed at the joint site. The interior of the implant may be provided with lubricious material to facilitate movement between the inner wall surfaces and to minimize contact wear therebetween. The polymeric walls of the implant may be impregnated with or otherwise carry tissue regeneration agents such as stem cells, living chondrocytes, and/or genes to repair joint surfaces.

In some embodiments, the first inflation medium imparts rigidity in the implant. In some embodiments, the first inflation medium imparts cushion in the implant. In some embodiments, the inflation medium chosen for the first inflation medium, and/or the particular choice of chamber (in embodiments having multiple chambers) filled with such first inflation medium aligns the joint. In some embodiments, the inflation medium chosen for the first inflation medium, and/or the particular choice of chamber (in embodiments having multiple chambers) filled with such first inflation medium aligns the bones of the joint. In some embodiments, the inflation medium chosen for the first inflation medium, and/or the particular choice of chamber (in embodiments having multiple chambers) filled with such first inflation medium changes the bone alignment. In some embodiments, the inflation medium chosen for the first inflation medium, and/or the particular choice of chamber (in embodiments having multiple chambers) filled with such first inflation medium improves joint alignment. In some embodiments, the inflation medium chosen for the first inflation medium, and/or the particular choice of chamber (in embodiments having multiple chambers) filled with such first inflation medium restores, at least in part, joint alignment. In some embodiments, individual chambers of the interior may be selectively inflated with a first inflation medium and/or a second inflation medium. In some embodiments, individual chambers of the interior are selectively inflated with a first inflation medium and/or a second inflation medium in order to reconstruct the joint and/or bones of the joint.

In some embodiments the inflation medium comprises living chondrocytes.

The implant interior (balloon interior) may be inflated with methymethacrylate as a liquid that becomes a solid or semi-solid (rigid or semi-rigid). In some embodiments, the inflation medium is a methyl methacrylate or other biocompatible hardening substance which can flow when initially put into the chamber, and hardens to become a rigid piece or semi-rigid piece or solid piece. The methyl methacrylate or other biocompatible hardening substance may conform to the shape of the chamber, or may conform to the shape of a space between bones and/or other joint structures. The methyl methacrylate or other biocompatible hardening substance may conform to a form chosen by the surgeon using tools and/or pressure to influence the final shape of the rigid piece formed by the methyl methacrylate or other biocompatible hardening substance upon hardening.

The side wall extends between the first and second walls to form an interior which receives filling material through tube (also called a conduit herein, or may be called an inflation port). In some embodiments, the inflation port is not a tube, but is a valve which may or may not extend from a wall of the implant. The valve may be part of a wall of the implant, or part of the balloon or a portion thereof. The implant would also be appropriate for one condyle of the knee, but other shapes may be desired for other joint configurations whether relatively flat or more inflated toward a ballooning construct. In some embodiments, the inner diameter of the inflation port (or tube) is 5 millimeters maximum. In some embodiments, the inner diameter of the inflation port is about 1 millimeter. In some embodiments, the inner diameter of the inflation port is about 2 millimeters. In some embodiments, a needle (of typical needle sizes) may be used to inflate the implant.

A separate portal or tube (not shown) or the existing conduit (tube or valve), may be used to extract noxious inflammatory enzymes that can be aspirated at appropriate clinical intervals. Inflammatory enzymes in the COX1, COX2 and or 5LOX pathways can be extracted. Viscolubricants can be injected into the interior of the resilient arthroplasty implant through existing conduit or through a long needle to aide in distension, expansion, lubrication (with predetermined microporosity).

In some embodiments, an inflation medium that generates heat (by means of a catalyst reaction or other means) may be used to delver heat to a joint structure. The heat may aide hyaline cartilage annealing. Thermal effects of the implant materials are calculated accordingly to benefit and protect the joint surface analogous to a dry suit or wet suit for a scuba diver exposed to temperature extremes. Embodiments of the implant generally seek to avoid head from friction via lubricious coatings whether allograph as amniotic membrane or polymer, for non-limiting example.

The implant design allows for ease of implantation. In one embodiment, the implant can be inserted into the knee joint via a cannula. Because of the design of the implant, the implant may be inserted into the joint capsule. In one embodiment, the implant, is deployed into the joint capsule.

The implant in some embodiments is inserted arthroscopically through a cannula about 10 mm in diameter with the implant in the deflated construct, and once inside the prepared joint space and secured therein by the appendages or tabs, the implant will be distended or inflated with gas, gel, fluid or fluid that becomes a resilient solid to fill the original natural space of a bone of the joint (whether the tibia, femur or patella). Tensioning will be by the surgeon's sense of proper pressure application aided by a gauged syringe for insertion of viscolubricants such as Synvisc, Hyalgan, Supartz and/or analgesics such as lidocaine gel. The insertion of liquids to the joint per se may be directly, through a cannula to the joint space previously in place for debridement, and or via a cannula or tube that is not part of the original implant assembly. Once the joint is cleaned, the implant is inserted and appropriately fixed to avoid extrusion or dislocation thereof. This may be via attachment of the implant tabs and/or by a combination of tab use plus intended friction created by implant surface coverings (analogous to Velcro) or a draw string at the smaller base of the implant.

Attachment Elements and Couplers

In some embodiments the attachment elements of the implant comprises holes through which screws or other couplers may be placed to attach the implant to an attachment site (or connection site) in the bone of the knee. In some embodiments, the holes are created arthroscopically. In some embodiments the holes are pre-fabricated in the implant. In some embodiments, the holes may be made prior to implantation based on the patient's particular anatomy. In some embodiments, the holes are reinforced by a reinforcing material of the implant. The reinforcing material may be a polymer of sufficient durometer and/or tear resistance to reinforce the screw hole. The reinforcing material may be comprise metal. In some embodiments, there is no preformed hole, but rather screws (or another coupler) secure the attachment tabs (which may be a non-balloon portion of the implant) to the joint component (bone, etc) by creating their own hole when implanted. In some embodiments, the implant may comprise tabs that are adapted to receive staples or other couplers described elsewhere herein.

The implants described herein may comprise attachment elements (or tabs) which may then by attached or coupled to tissue of a component of the joint (whether to a bone or a ligament or a tendon or other joint component) by a coupling device. Coupling devices (or couplers) may comprise at least one of screws, washers, sutures, suture anchors (metal and/or biodegradable), rivots, staples (with and/or without teeth), stabilizers, glues, hooks of cylindrical wire or flattened sheet metal into bone holes or slots respectively. The coupling devices may be resorbable or not. Also, the coupling devices may comprise at least one of strings (i.e. drawstrings), reigns, lassos, sutures, and lanyards. The strings, reigns. lassos, sutures, and/or lanyards may join with themselves and/or other coupling devices. The strings, reigns. lassos, sutures and/or lanyards may be directed not only into bone with or without anchors, but also through ligaments, tendons or loose segments of cartilage that the surgeon intends to preserve.

The implant may be affixed to the femur. The methods to affix, secure, anchor, screw or stabilize the implant are described herein. The implant can be secured in a manner designated by one of ordinary skill in the art. In one embodiment, the implant may have pre-fabricated holes to allow for screws or other types of anchoring devices. The implant may have from 0-20 holes. Preferably, there are 3-10 holes. A preferred embodiment is disclosed which comprises 5 holes. In one embodiment, one hole is specifically located on the implant in a location adjacent the condyle notch of the knee. The holes may be 0.01 mm to 30 mm in diameter. Preferably, the diameter of the holes is from 0.5 to 7 mm. More preferably the diameter of the holes is from 2 to 5 mm. In some instances, the holes have a 4.5 mm diameter. In other instances, each hole has a different diameter. In still another instance, some holes may have a first diameter while other holes a second or third diameter. In a preferred embodiment, the holes are circular, however the holes may be square, rectangular, crescent shaped, or any appropriate shape for aiding in the coupling or attaching of the implant to an area in the joint such as to bone. The part of the implant defining the holes can be made of the same or a different material so as to fortify or strengthen the implant near or around the anchoring or coupling means.

The implant can be secured with a coupling device as described herein. In some embodiments, from 0 to 30 coupling devices are used. More preferably, from 5 to 10 coupling devices are used.

In some embodiments the implant is fashioned for a left knee. In other embodiments the implant is fashioned for a right knee. The rim may engage a bone or cartilage. The rim may comprise a scaffold. The rim may engage the joint capsule. The rim may be filleted or demonstrate a variable fillet. In a separate embodiment, the rim may be raised.

In some embodiments, the implant is of a standard size. In other embodiments, the implant is fitted for a right knee. In other embodiments, the implant is fitted for a left knee. In some embodiments, the appendage that engages the medial femoral condyle is larger than the appendage which engages the lateral femoral condyle.

The posterior of the knee can be difficult to access without disturbing joint components (or in order to minimize such disturbance) such as tendons, ligaments, etc. Thus, in some embodiments, the implant comprises strings, reigns. lassos, and/or lanyards that may pass from the posterior of the implant via the intercondylar notch anteriorly to join with themselves and/or other coupling devices. These couplers may be pre-coupled to the implant, and the implant and its couplers may be configured to be pulled (or cinched) from the anterior of the implant once the implant is in its general location relative to the condyle in order to finally position the implant about the condyle—in particular in order to cinch the implant about the posterior of the condyle. Likewise, in some embodiments where the implant is premolded, the coupler as described are adapted to move the implant to its final position with conformity to the condyle's posterior with minimal disturbance to the joint structures at the joint's posterior (minimal cutting, minimal moving, and or minimal detachment, for non-limiting example).

In some embodiments, the implant comprises a skirt (or sleeve) that conforms to the contours of the bone (whether a condyle of the femur, a patella, or a tibia) as a coupler.

In some embodiments, a screw through tab having reinforced center holes may be part of the implant. For example, the implant may comprise polymer covered metal washer holes. The screw may go through the holes. Another embodiment may comprise a staple having spikes as shown in FIGS. 13A-13D. FIGS. 13A-13D depict multiple views of a staple adapted to couple an implant to a bone of the joint. FIG. 13A depicts an embodiment of an implant 20 having a tab 10*a* that is coupled to bone using a staple 12. FIGS. 13B & 13C depict a staple 12 as described herein having teeth 18. FIG. 13C depicts an embodiment of a tab 10*a* that is coupled to bone using a staple 12 having teeth 18. Combinations of spikes and screws may be used in some embodiments, or combinations of other couplers. The implant may be configured to allow a surgeon the option of several types and sizes of couplers, as each patient differs with regard to size and depth of lesion, bone stock, regrowth capability, and compliance with advised recovery, and each surgeon has his own strengths and comforts when working with such implants.

The edge of the implant may have a depending skirt to secure or anchor the implant to the end of bone (femur), but may have one or more depending tabs (or appendages) that may be employed for similar functions as will be discussed in other embodiments. The skirt (and/or tabs, and/or appendages) may tightly fit about the end of the femur, or the skirt can be secured by adhesive (e.g. methyl methacrylate, bone ingrowth) to the supporting bone structure or be mechanically connected by staples, screws and the like. Moreover, the lower portion of the skirt may be secured by a purse string suture or a suitable strand (elastic or tied) that is tightly bound about the outside of the skirt.

FIGS. 12A, 12B, and/or 12C alternatively may be used to describe a patch implant or a unicompartment knee implant described herein, having appendages 4*a*, 4*c*, extending from a balloon 6 and including holes 8*a*, 8*b*, 8*c*, and/or tabs 10*a*, 10*b*. 10*c*, 10*d*, 10*e*, 10*f*, which may be used with couplers (not shown) to couple the implant to a bone of the knee joint (which may be the femur, the tibia, or the patella). Features shown in FIG. 12A, 12B, and or 12C are common to both the unicompartment knee implant (also discussed elsewhere herein) and the patch implant (also discussed elsewhere herein), although dimensions may differ as described elsewhere herein.

FIGS. 13A-13D depict multiple views of a staple 12 adapted to couple implant 14 (such as those described herein) to a bone 16 of the joint. FIG. 13A depicts a staple 12 coupling a tab 10*a* of an appendage 4*a* to the bone 16 of the joint (wherein the portion of the staple 12 embedded in the bone 16 is shown as a dashed line). FIG. 13B depicts a view of a staple 12 having teeth 18 to grasp the tab 10*a* of the implant 14. Similarly, FIG. 13C depicts a view of a staple 12 having teeth 18 to grasp the tab 10*a* of the implant 14. FIG. 13D depicts a staple 12 attaching the tab 10*a* of an implant to a bone 16, the dotted lines show the portion of the tab 10*a* that is compressed by the staple 12 and teeth 18 thereof.

For example, FIG. 14 depicts an embodiment of the knee implant 20 having appendages 4 *a*, 4 *b*, 4 *c*, 4 *d*, including holes 8 *a*, 8 *b*, 8 *c*, 8 *d* and tabs 10 *a*, 10 *b* and including slots 26 *a*, 26 *b* to accommodate ligaments of the knee joint as well as side views of the same knee implant. Couplers as described elsewhere herein may be used to couple the implant 20 to the distal femur. In some embodiments, there may only tabs, only holes, or only appendages, or combinations thereof. In some embodiments, there may be other ways to couple the implant to the distal femur, as described elsewhere herein (sutures, drawstrings, skirts, glue, etc). In some embodiments, the couplers create the holes 8 *a*, 8 *b*, 8 *c*, 8 *d*, or other holes (not shown) when the implant is placed against the distal femur. In some embodiments, the holes are pre-formed in the appendage prior to implantation. In some embodiments, the holes are reinforced as described elsewhere herein. As shown here, the appendages in some embodiments are different in shape and/or size to accommodate the differences in condyle size and/or shape. For example the medial condyle tends to be larger than the lateral condyle, and thus appendage 4 *d* that is intended to wrap over the medial condyle may be longer and/or wider than the appendage 4 *c* intended to wrap over the lateral condyle. Shown in the embodiment depicted in FIG. 14 are the different hole placements from the side view, showing the differences in positioning of the holes to accommodate the differences in anatomic structure and size of the condyles. Likewise, the slots may be different in shape and/or size and/or position to accommodate the ligaments and/or tendons of the joint or other structures and functions of the joints of the knee, and to allow for placement of the implant with minimal disturbance (cutting, manipulation, for example) of the joint components such as tendons, ligaments, and other soft or hard tissues. For example, slot 26 *a* is shaped and positioned to accommodate the cruciate ligaments of the knee, at least. Additionally, as shown in the side views of the embodiment shown in FIG. 14, the implant has a first wall 28 adapted to be adjacent the femur that is of approximately the same thickness than the second wall 30. In some embodiments, the first wall 28 is configured to have therapeutic benefits (pharmacologic, healing, and/or in-growth properties) as described elsewhere herein. The second wall 30 may additionally and/or alternatively be configured to have a therapeutic effect (pharmacologic, healing, and/or in-growth properties). Additionally, the thickness of the implant in certain locations is variable to add cushioning to the implant as well as to provide joint spacing. In certain embodiments, the material is not variable in thickness, but provides the same cushioning and/or joint spacing for the bones of the joint. The central region in the embodiment of FIG. 14 is thicker material to add at least one of: cushioning, buffering, joint space, restore cushioning, and to respond to clinical need.

Any of the balloons described herein with regard to any of the figures may add cushioning, padding, strength, durability, flexibility, or any other aspect noted herein, and need not be a chamber per se, nor be inflatable per se. Rather they are merely distinguishable in certain embodiments from the walls which are on either side of them in composition or function or both. In some embodiments, the balloon and its interior is not materially different in composition or function from one of the walls. In some embodiments, they are not materially different in composition or function from either of the walls.

Figure 15A:
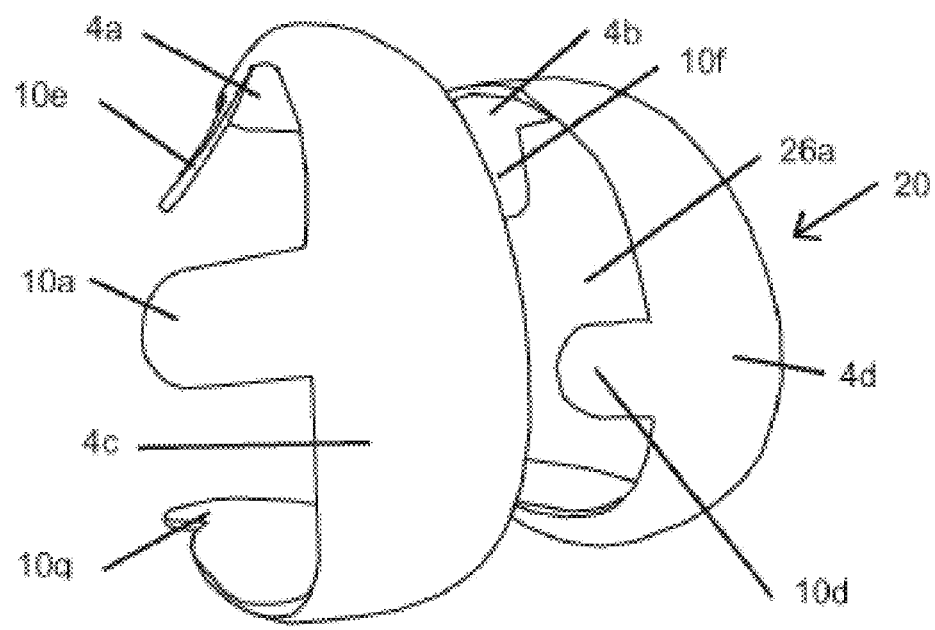
FIGS. 15A, 15B, and 15C show several views of an embodiment of an implant which has no definable chamber, rather the material of the implant itself provides the cushion to the bones of the joint (at least).
Figure 15B:
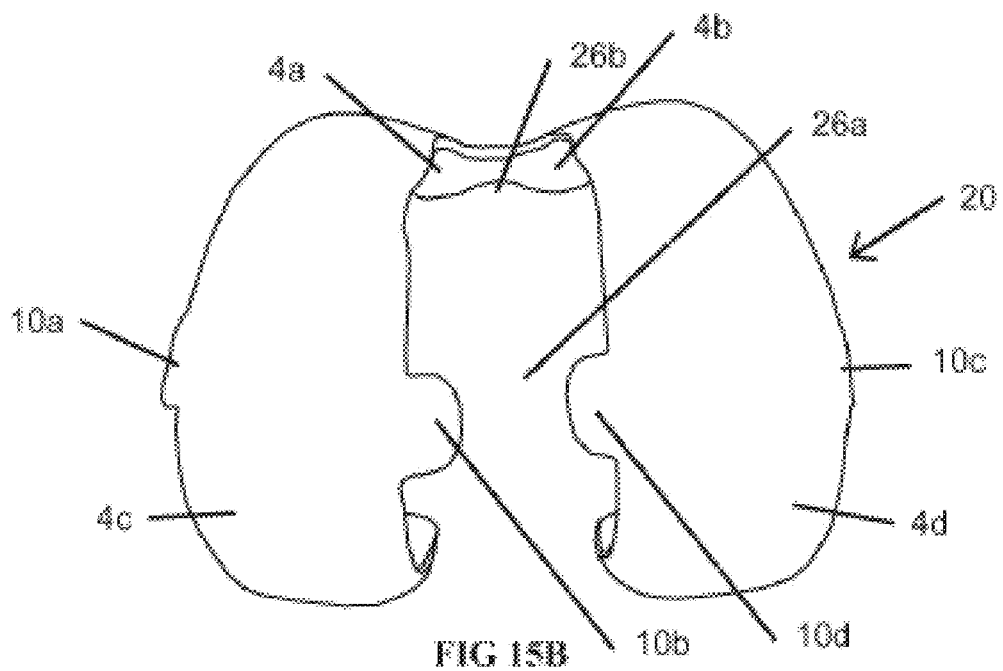
Figure 15C:
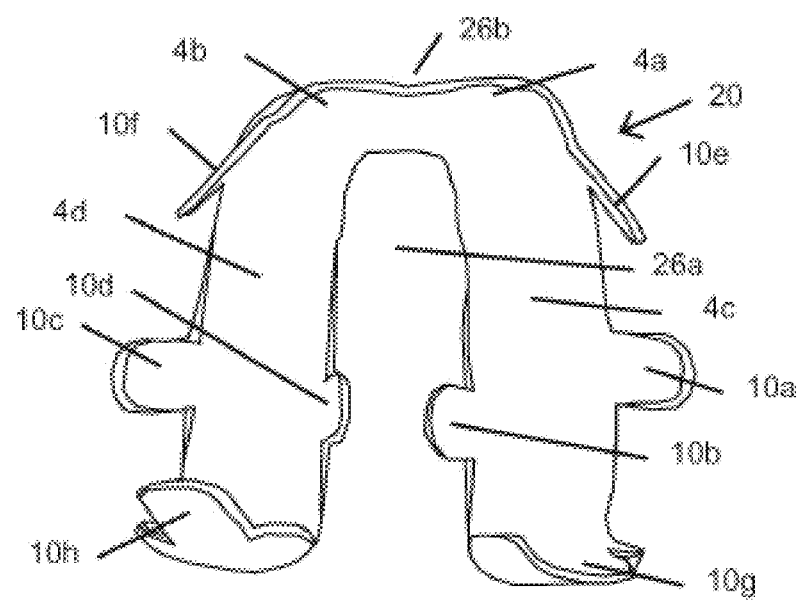

FIGS. 15A, 15B, and 15C show several views of an embodiment of an implant which has no definable chamber, rather the material of the implant itself provides the cushion to the bones of the joint (at least). The implant in 15A, 15B, and 15C is generally H or V-shaped, having a slot 26 *b* that is significantly smaller than as shown other embodiments (for example FIGS. 3, 4, 5, 6A, 6B, 7, 14). In certain embodiments, an implant shaped generally like FIGS. 15A, 15B, and 15 *c* may comprise a chamber which, if the implant were shown in cross section, may comprise a different material than the wall of the implant itself, or may be the same material but with different geometric or chemical or physical properties, as noted herein. FIGS. 15A, 15B, and 15C depict an embodiment of the knee implant 20 having appendages 4 a, 4 b, 4 c, 4 d and tabs 10 a, 10 b, 10 c, 10 d, 10 e, 10 f, 10 g, 10 h and including slots 26 a, 26 b to accommodate ligaments of the knee joint. Couplers as described elsewhere herein may be used to couple the implant 20 to the distal femur. In some embodiments, there may only tabs, only holes, or only appendages, or combinations thereof. In some embodiments, there may be other ways to couple the implant to the distal femur, as described elsewhere herein (sutures, drawstrings, skirts, glue, etc). In some embodiments, the couplers create holes (not shown) when the implant is placed against the distal femur. In some embodiments, the holes are pre-formed in the appendage prior to implantation. In some embodiments, the holes are reinforced as described elsewhere herein. As shown here, the appendages in some embodiments are different in shape and/or size to accommodate the differences in condyle size and/or shape. For example the medial condyle tends to be larger than the lateral condyle, and thus appendage 4 d that is intended to wrap over the medial condyle may be longer and/or wider than the appendage 4 c intended to wrap over the lateral condyle. The slots may be different in shape and/or size and/or position to accommodate the ligaments and/or tendons of the joint or other structures and functions of the joints of the knee, and to allow for placement of the implant with minimal disturbance (cutting, manipulation, for example) of the joint components such as tendons, ligaments, and other soft or hard tissues. For example, slot 26 a is shaped and positioned to accommodate the cruciate ligaments of the knee, at least. The thickness of the implant in certain locations is variable to add cushioning to the implant as well as to provide joint spacing. In certain embodiments, the material is not variable in thickness, but provides the same cushioning and/or joint spacing for the bones of the joint.

Figure 16:
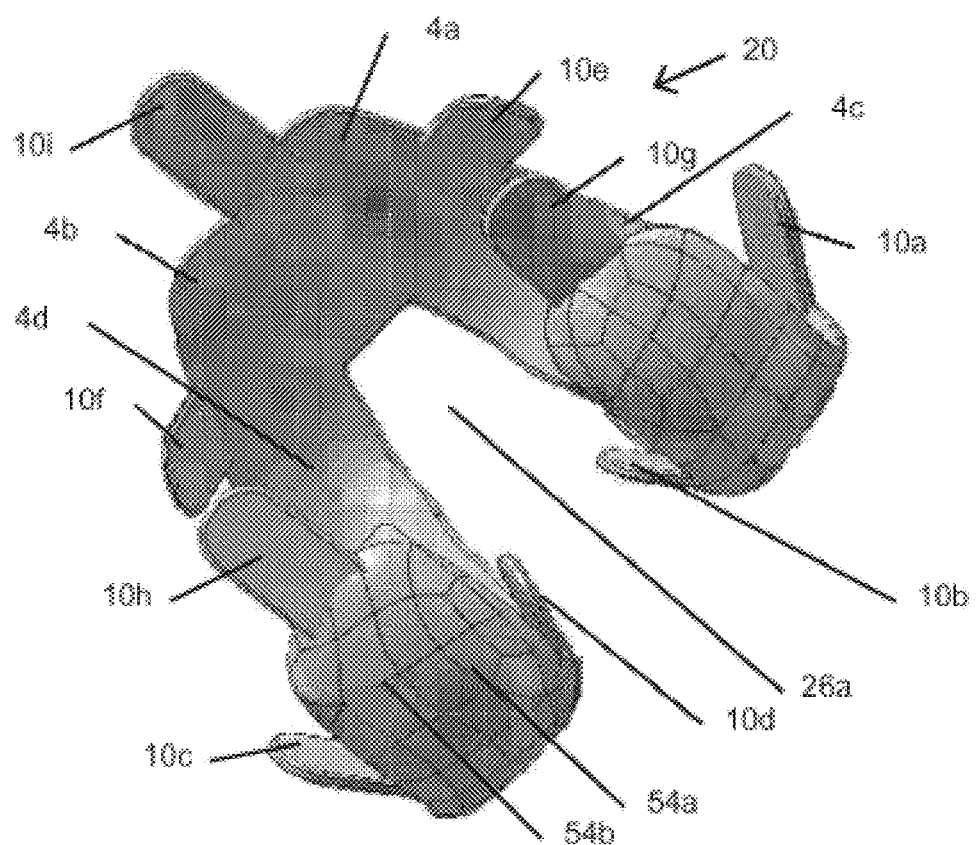
FIG. 16 depicts a knee implant embodiment that is generally H or V-shaped, having a slot 26 *b* that is significantly smaller than other embodiments, and in this embodiment is effectively replaced with a tab 10 *i* at the same location (e.g. 10 *i*).

FIG. 16 depicts a knee implant embodiment that is generally H or V-shaped, having a slot 26 b that is significantly smaller than other embodiments, and in this embodiment is effectively replaced with a tab 10 i at the same location (e.g. 10 i). FIG. 16 depicts an embodiment of the knee implant 20 having appendages 4 a, 4 b, 4 c, 4 d and tabs 10 a, 10 b, 10 c, 10 d, 10 e, 10 f, 10 g, 10 h, 10 i and including a slots 26 a to accommodate ligament(s) of the knee joint. Couplers as described elsewhere herein may be used to couple the implant 20 to the distal femur. Contour lines 54 a, 54 b, for example, are also depicted in FIG. 16, however these are not necessarily significant other than to show contour of parts of the implant 20, although they may be in the case where a mesh is provided in the implant. In some embodiments, there may only tabs, only holes, or only appendages, or combinations thereof. In some embodiments, there may be other ways to couple the implant to the distal femur, as described elsewhere herein (sutures, drawstrings, skirts, glue, etc). In some embodiments, the couplers create holes (not shown) when the implant is placed against the distal femur. In some embodiments, the holes are pre-formed in the appendage prior to implantation. In some embodiments, the holes are reinforced as described elsewhere herein. As shown here, the appendages in some embodiments are different in shape and/or size to accommodate the differences in condyle size and/or shape. For example the medial condyle tends to be larger than the lateral condyle, and thus appendage 4 d that is intended to wrap over the medial condyle may be longer and/or wider than the appendage 4 c intended to wrap over the lateral condyle. The slot 26 a may be different in shape and/or size and/or position to accommodate the ligaments and/or tendons of the joint or other structures and functions of the joints of the knee, and to allow for placement of the implant with minimal disturbance (cutting, manipulation, for example) of the joint components such as tendons, ligaments, and other soft or hard tissues. For example, slot 26 a is shaped and positioned to accommodate the cruciate ligaments of the knee, at least. The thickness of the implant in certain locations is variable to add cushioning to the implant as well as to provide joint spacing. In certain embodiments, the material is not variable in thickness, but provides the same cushioning and/or joint spacing for the bones of the joint. In certain embodiments, an implant shaped generally like FIG. 16 may or may not comprise a chamber which, if the implant were shown in cross section, may comprise a several materials which may be the same as or different from any wall of the implant itself, or may be the same material but with different geometric or chemical or physical properties, as noted herein.

Figure 17:
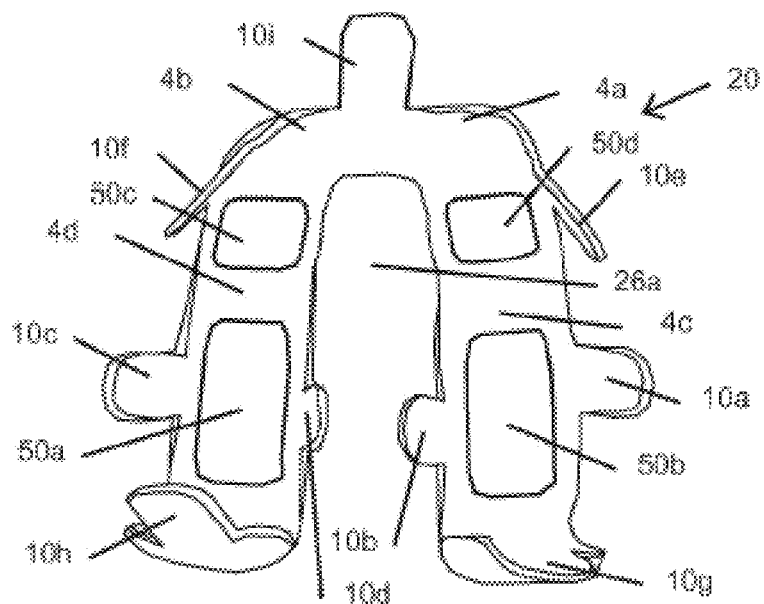
FIG. 17 depicts a knee implant embodiment similar to FIG. 16 which shows a posterior view including the location(s) 50 *a*-50 *d* where a fill material such as cement may be placed.

FIG. 17 depicts a knee implant embodiment similar to FIG. 16 which shows a posterior view including the location(s) 50 a-50 d where a fill material such as cement may be placed. The fill material may be added in any one location 50 a, 50 b, 50 c, or 50 d, or added in several of locations 50 a, 50 b, 50 c, and 50 d or likewise be added anywhere on the first or second wall of the implant which contacts the first, second, and/or third bone. The fill material may be used to both cushion (as do balloons 6 in other figures) and/or secure the device to the bone in the case of a bone cement or a combination of these functions. In the case where the cement is used as the fill material, the cement may be used in an element that may or may not have any, some, or all of tabs 10 a-10 i. The cushion, thus can act as a coupler (fixation element) and/or as a cushion and/or spacer for the joint bones. The cushion (whether a fill material such as cement or another material) may also be placed adjacent to a first wall or second wall, and not necessarily between said first wall and second wall.

Figure 18:
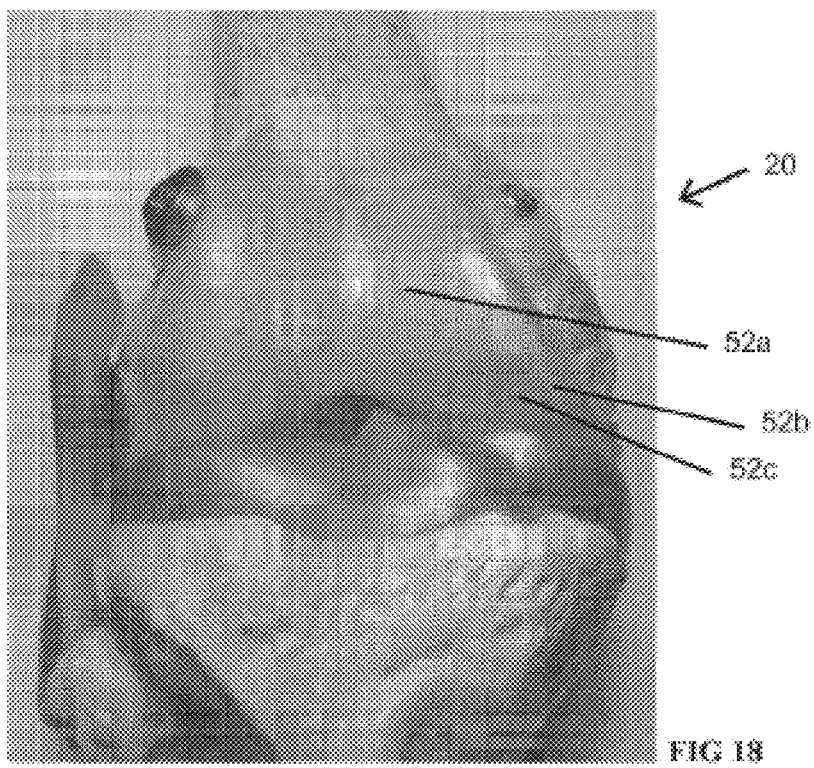
FIG. 18 is an anterior-posterior view of an embodiment of the implant 20 attached to a knee model.

FIG. 18 is an anterior-posterior view of an embodiment of the implant 20 attached to a knee model. The implant here comprises chambers 52 a, 52 b, 53 c, at least (in this case, nano-inflated air pockets). Although sparsely shown in this embodiment, the frequency, size, etc. could be adapted to smaller chambers, larger chambers, more frequent chambers, more concentrated in particular areas of the implant, less concentrated in particular areas of the implant, or similarly adjusted. The chambers can be diffuse, of any size, containing compressible gas (air), cells, pharmacologics, liquids, beads, metals, or other materials as noted herein.

Figure 19:
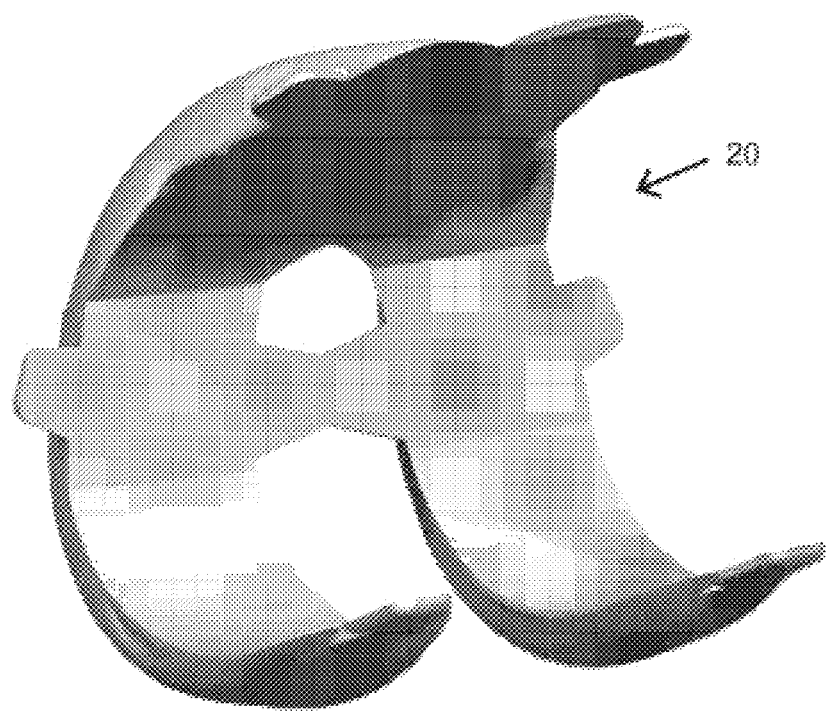
FIG. 19 depicts an implant 20 which is more squarely cut for interface with a femur, for example, which has been cut square such as is done in certain total knee arthroplasty procedures.

FIG. 19 depicts an implant 20 which is more squarely cut for interface with a femur, for example, which has been cut square such as is done in certain total knee arthroplasty procedures. The implant in this situation may comprise a polymer alone (of soft or hard durometer) and/or metal. The walls may be contiguous or include a chamber that is optionally filled or fillable as noted herein. Although tabs are shown in FIG. 19, these are optional in embodiments where another attachment element (fixation element) is used such as cement or a metal pin or screw or snap through an appendage of the device.

Figure 20A:
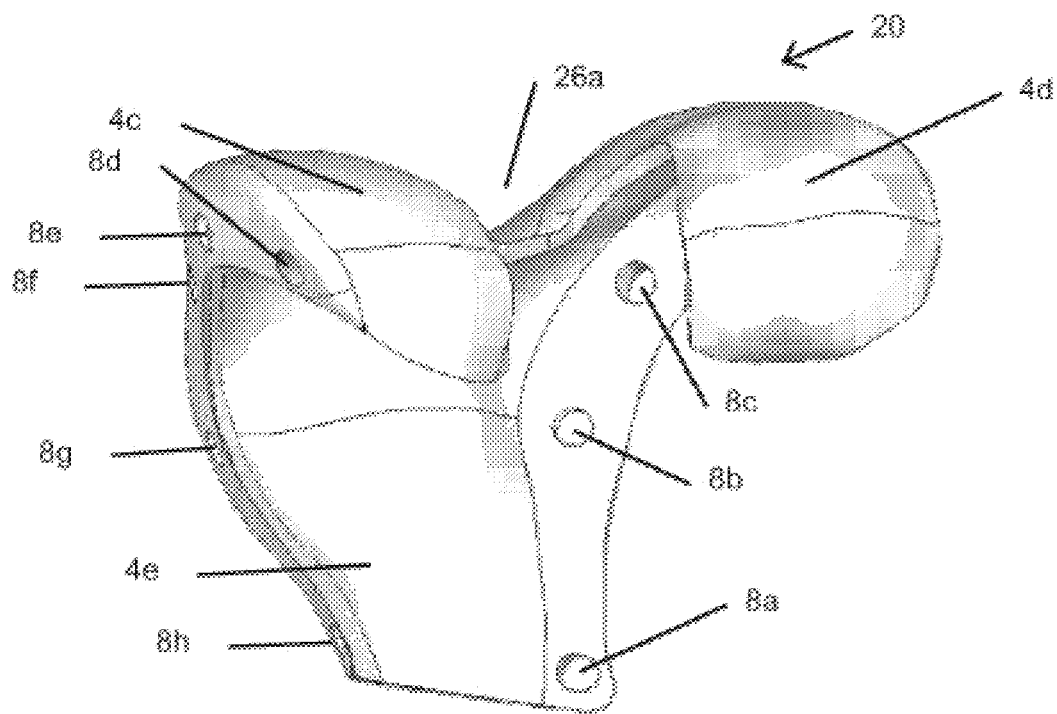
FIGS. 20A and 20B depict a knee implant embodiment that is generally V-shaped or Y-shaped, and in this embodiment the notch 26 *b* of other embodiments, or the tab 10 *i* of other embodiments is effectively replaced with an appendage 4 *e* at the same location.
Figure 20B:
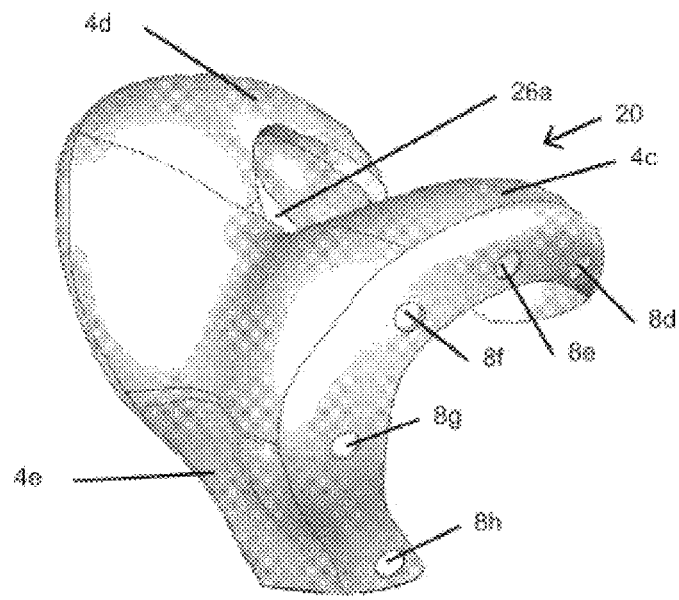

FIGS. 20A and 20B depict a knee implant embodiment that is generally V-shaped or Y-shaped, and in this embodiment the slot 26 b of other embodiments, or the tab 10 i of other embodiments is effectively replaced with an appendage 4 e at the same location. FIG. 20A depicts an embodiment of the knee implant 20 having appendages 4 c, 4 d, and 4 e and holes 8 a (not shown, in FIG. 20B), 8 b (not shown, in FIG. 20B), 8 c (not shown, in FIG. 20B), 8 d, 8 e, 8 f, 8 g, 8 h, 8 i, (not shown, substantially similarly positioned as 8 e on the same edge as 8 a-8 c of FIG. 20A), 8 j (not shown, substantially similarly positioned as 8 d on the same edge as 8 a-8 c of FIG. 20A), and including a slot 26 a to accommodate ligament(s) of the knee joint. Couplers as described elsewhere herein may be used to couple the implant 20 to the distal femur through slots 8 a-8 j. Contour lines are also depicted in FIGS. 20A and 20B, however these are not necessarily significant other than to show contour of parts of the implant 20, although they may be in the case where a mesh is provided in the implant. In some embodiments, there may only tabs, only holes, or only appendages, or combinations thereof. In some embodiments, there may be other ways to couple the implant to the distal femur, as described elsewhere herein (sutures, drawstrings, skirts, glue, etc). In some embodiments, the tabs comprise holes. In some embodiments, the couplers create holes (not shown) when the implant is placed against the distal femur. In some embodiments, the holes are within the peripheral rim of the knee implant. In some embodiments, the holes are within the region of the intercondylar notch medially and/or laterally. In some embodiments, the holes are through the polymer. In some embodiments, the holes are through a reinforced rim. In some embodiments, the holes are pre-formed in the appendage prior to implantation. In some embodiments, the holes are reinforced as described elsewhere herein. As shown here, the appendages in some embodiments are different in shape and/or size to accommodate the differences in condyle size and/or shape. For example the medial condyle tends to be larger than the lateral condyle, and thus appendage 4 d that is intended to wrap over the medial condyle may be longer and/or wider than the appendage 4 c intended to wrap over the lateral condyle. The slot 26 a may be different in shape and/or size and/or position to accommodate the ligaments and/or tendons of the joint or other structures and functions of the joints of the knee, and to allow for placement of the implant with minimal disturbance (cutting, manipulation, for example) of the joint components such as tendons, ligaments, and other soft or hard tissues. For example, slot 26 a is shaped and positioned to accommodate the cruciate ligaments of the knee, at least. The thickness of the implant in certain locations is variable to add cushioning to the implant as well as to provide joint spacing. In certain embodiments, the material is not variable in thickness, but provides the same cushioning and/or joint spacing for the bones of the joint. In certain embodiments, an implant shaped generally like FIG. 20A or 20B may or may not comprise a chamber which, if the implant were shown in cross section, may comprise a several materials which may be the same as or different from any wall of the implant itself, or may be the same material but with different geometric or chemical or physical properties, as noted herein. As shown in FIGS. 20A and 20B, thickness of between the first wall (part configured to touch the femur condyle) and the second wall (part configured to touch the tibia), is shown for example in the slot 26 a (which may be called a notch herein), thus showing a side wall as described elsewhere herein to provide the thickness to the implant at the condyle(s). This thickness may be a result of a thickness of a material of the implant (as in where the implant comprises a compliant polymer), or due to an inflation of a balloon that resides between the first wall and the second wall and the side wall. In some embodiments, the implant comprises a Dyneema® mesh. The implant may comprise Dyneema® fiber. In some instances, the implant comprises Dyneema Purity® fiber. In some embodiments, the implant comprises a Dyneema Purity® UG fiber. In some embodiments, the implant comprises a Dyneema Purity® VG fiber. The implant may comprise a fiber. The implant may comprise a polyethylene. The implant may comprise a polyethylene fiber.

In all descriptions provided herein of the dual compartment implant, the implant may instead be configured to couple to or emerge from the tibia and/or patella. In all descriptions provided herein of the dual compartment implant, the implant may instead be configured to couple to the tibia. It is the intention and understanding that the implant is suited for this purpose in certain embodiments with adjustments to account for dimensional differences of the tibia. Most descriptions provided herein are directed to embodiments coupling the implant to the femur, however, this is primarily for ease of description and continuity, and does not preclude embodiments wherein the implant is coupled to the tibia. Likewise, as noted elsewhere herein, there are embodiments where the implant may be coupled to two bones (at least), for example to both a tibia and a femur.

To be clear, in some embodiments, there is no chamber in the implant. In such an embodiment, the implant may have a single composition throughout the implant, and shaped as noted herein with attachment features as noted herein.

In some embodiments, the implant is a single layer polymer and has a variable thickness which is dependent or predicated upon the patient morphology or anatomy. Preferably, the implant thickness is predetermined based on a measurement of each patient's particular morphology. The measurements can be from MRIs, CT Scans, X-Rays, and/or arthroscopic inspection and/or through palpation or patient experience. Since a patients joint surface may not be perfectly smooth, the implant may be made with variable thicknesses or contours so that the underside or bone engaging side of the implant fills in any surface anomalies on the patients' bone or cartilage surface. The bone or femur engaging surface may comprise peaks and troughs. Living cells as mentioned may be imposed in between (and/or provided in or with the implant) troughs of the implant surface while the surface areas of prominence (the peaks of the surface) may be used for at least one of: space validation, traction, and cell protection. Pharmaceuticals may be coated on the bone engaging surface prior to, during or subsequent to implantation.

The joint space engaging side of the implant may be smooth with no texture or contours. In some embodiments, the bone engaging surface and the articulating surface have the same profile along any given dimensioned reference line as measured by the radius of curvature for each surface. In a particular embodiment, the underside or bone engaging side is adapted to fit and/or engage a patients existing anatomy. In another particular embodiment, the implant is of a thickness that fits into joint capsule without the need to make room in the joint by the removal of a patient's existing anatomy.

Figure 21A:
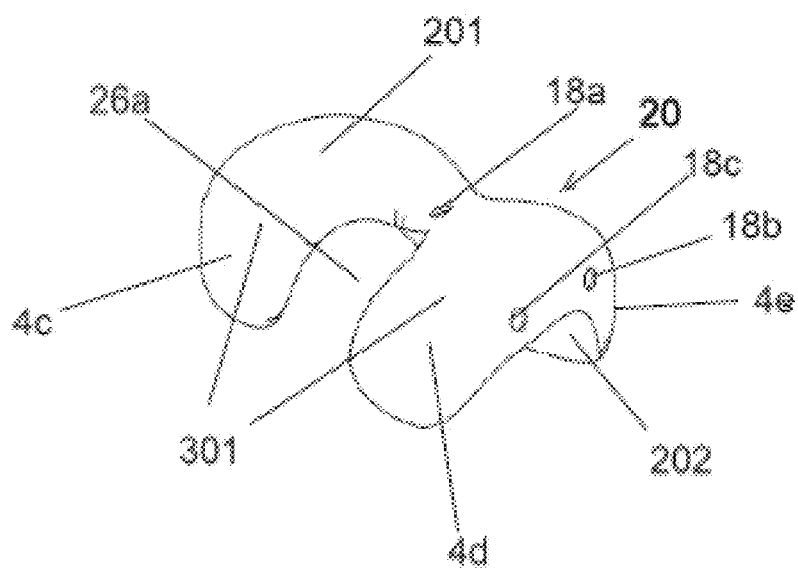
FIGS. 21A and 21B depict an oblique posterior view of a knee implant with medial and lateral appendages.

FIG. 21A depicts an embodiment of the implant 20 which has a main body 301 which hugs both the medial and lateral condyles and has no balloon. In some embodiments, the main body 301 may extend along the metathesis, epiphysis and/or diaphysis of the femur. The implant 20 may be designed to fit or hug the articulating end of a left femur and accommodate ligaments in slot 26a. Articulating surface 201 engages the joint space and underside surface 202 is a bone engaging surface. In preferred embodiments, the bone engaging surface is the surface that engages the femur, natural cartilage or remaining cartilage that is present on the end of the femur. The implant may be inserted into the capsule of the knee. Upon insertion of the implant into a right knee joint, appendage 4d will expand into the medial portion of the capsule or joint and appendage 4c will expand into the lateral portion of the capsule or joint. Upon insertion of the implant into a left knee joint or capsule, appendage 4d will expand into the lateral portion of the capsule or joint and appendage 4c will expand into the medial portion of the capsule or joint. Appendage 4e is designed to hug or engage an anterior portion of a femur and may be coextensive with appendages 4c and 4d. In some embodiments, the articulating surface of appendage 4e is designed to articulate relative to a patella. This FIG. 21A shows an implant with pre-fabricated holes 18a, 18b and 18c. The pre-fabricated holes can be used in combination with a coupling or attachment means as described herein. In some embodiments, the implant has no prefabricated holes (not shown).

Figure 21B:
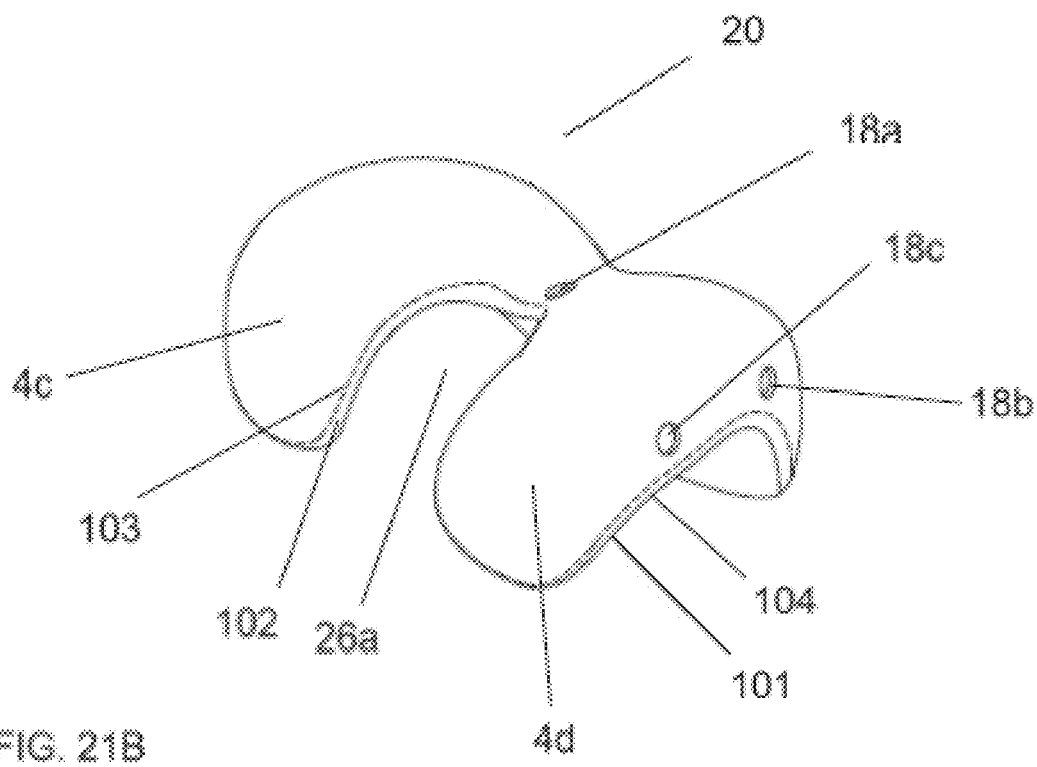

FIG. 21B shows an embodiment of implant 20 having a rim 101 circumscribing the implant including a lateral portion of the rim 104 and a medial portion of the rim (not shown). The rim 101 may extend and/or define the periphery of the implant. In some embodiments, the rim may be made of the same or different material as the implant and may extend along the metathesis, epiphysis and/or diaphysis of the femur. The rim may be filleted. The rim may have a variable fillet. FIG. 21B depicts the rim 101 having an outer most peripheral edge 102 and an inner boundary 103. The distance between the outer most peripheral edge 102 and an inner boundary 103 can be of variable lengths. Generally, the distance between the outer most peripheral edge 102 and an inner boundary 103 is 1.0 to 3.5 times the thickness of the implant. Most preferably, the distance between the outer most peripheral edge 102 and an inner boundary 103 is 1.5 to 2.5 times the thickness of the implant. For example, the distance between the outer most peripheral edge 102 and an inner boundary 103 is 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm, 4.0 mm, 4.1 mm, 4.2 mm, 4.3 mm, 4.4 mm, 4.5 mm, 4.6 mm, 4.7 mm, 4.8 mm, 4.9 mm, or 5.0 mm. The rim 101 may extend around all or part of the periphery of the implant. Pre-fabricated holes such as 18c and 18b may be fabricated in the rim 101 (not shown) and such holes may be used to facilitate anchoring of the implant. The implant rim 101 may be of variable thickness and construction independent of the rest of the implant. In some embodiments, the rim 101 may be of a different material than the rest of the implant. In other embodiments, the rim 101 may be contoured or textured, such as fashioned with protuberances.

Figure 22A:
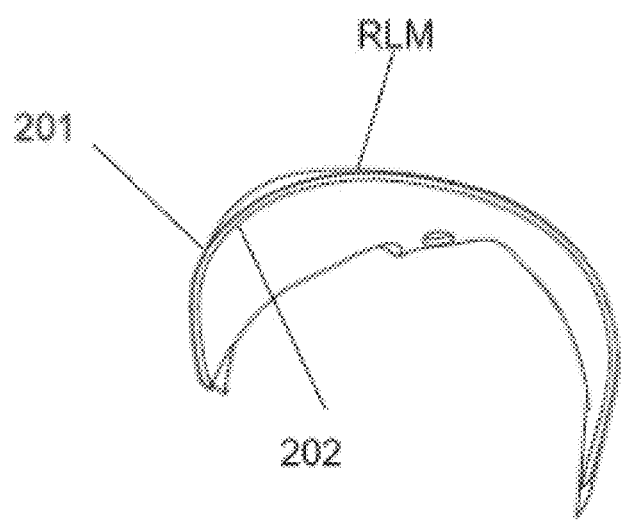
FIG. 22A depicts a lateral cutaway view of a knee implant.
Figure 22B:
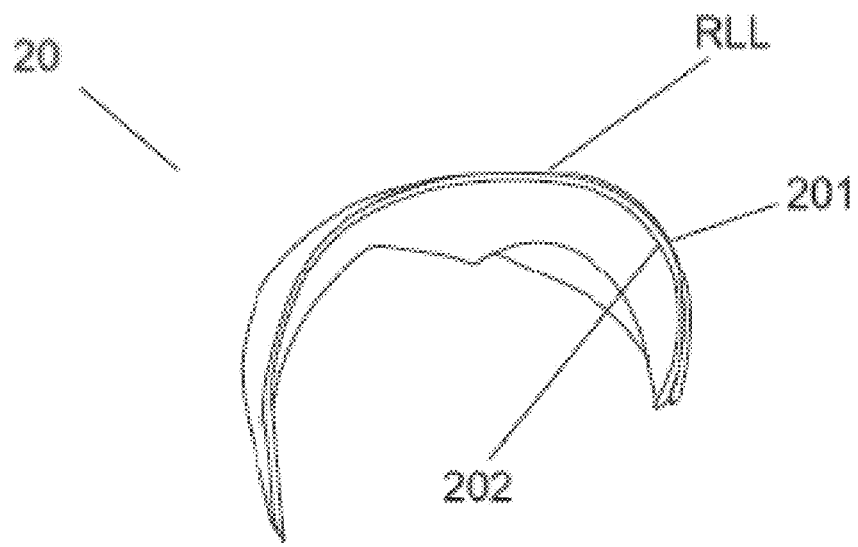
FIG. 22B depicts a medial cutaway view of a knee implant.
Figure 27:
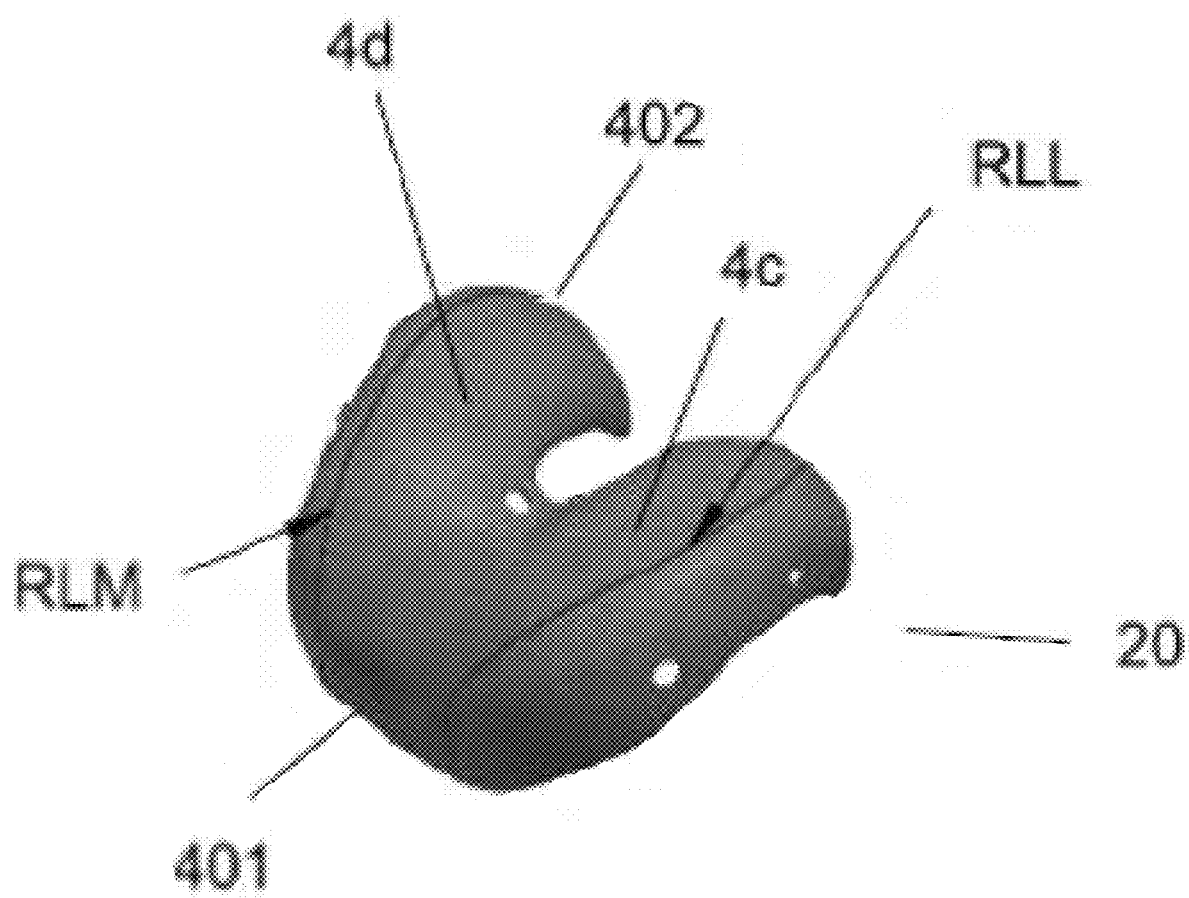
FIG. 27 depicts an isometric view of the joint articulating surface of an implant.

FIG. 22A shows a cross-sectional cutaway along RLM of FIG. 27 including the bone engaging surface 202 and joint articulating surface 201 which are also depicted. The thickness of the implant, which can be defined by the bone engaging surface 202 and the joint articulating surface 201 can be the same throughout the implant. In other words, the implant thickness can be the distance between the bone engaging surface 202 and the joint articulating surface 201. The implant thickness can be adjusted according to patient anatomy, physiology and need. In a preferred aspect, the thickness is 0.5 mm thick. In other aspects, the thickness can be from 0.01 mm to 5 mm. In some instances, the distance can be 0.02 mm, 0.03 mm, 0.04 mm, 0.05 mm, 0.06 mm, 0.07 mm, 0.08 mm, 0.09 mm, 0.1 mm, 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm, 4.0 mm, 4.1 mm, 4.2 mm, 4.3 mm, 4.4 mm, 4.5 mm, 4.6 mm, 4.7 mm, 4.8 mm, 4.9 mm, or 5.0 mm. The thickness of the implant may be made to a custom fit for a particular patient's knee (left or right). For example, the measurements for the custom fit can be particular such as 1.025 mm, 1.050 mm, or 1.075 mm. The thickness in some embodiments may vary throughout the implant to accommodate a particular patient's anatomy. FIG. 22B shows a medial cutaway of the implant along RLL (also shown in FIG. 27). In some embodiments, the thickness of the implant has an average consistency. In some embodiments, the thickness of the implant may vary to accommodate certain features of a patient's anatomy. In a preferred aspect, the average thickness of the implant is consistent throughout the main body of the implant.

Figure 23:
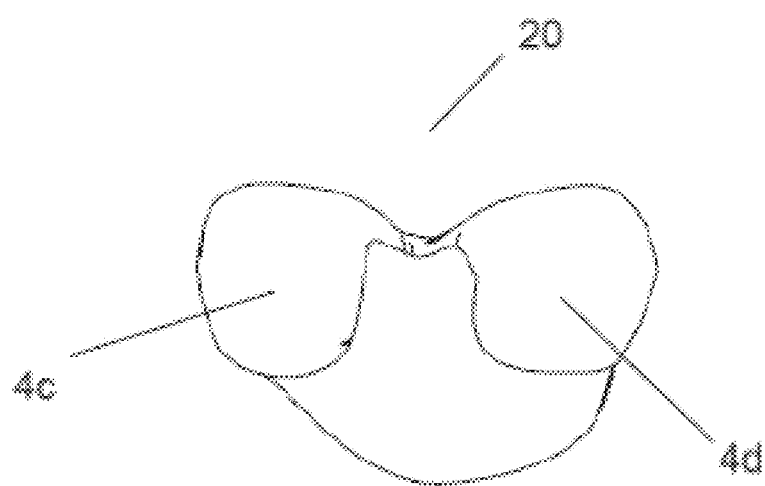
FIG. 23 depicts a posterior view of a knee implant with medial and lateral appendages.

FIG. 23 is a posterior view of the implant. Appendage 4d may be different from appendage 4c.

Figure 24:
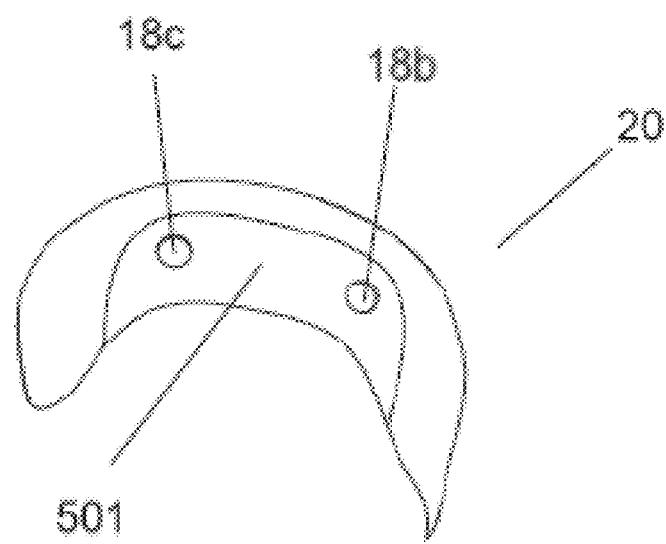
FIG. 24 depicts a side view of a knee implant.

FIG. 24 shows a side view of the implant 20 having a bridge support 501. The bridge support 501 may be a thickened flange on both the medial and lateral sides of the implant to provide stability and contact surface for adhering to the bone and or cartilage. The bridge support 501 may be coextensive with the main body of the implant. The bridge support 501 may be made of the same or different material as the implant and may extend along the metathesis, epiphysis and/or diaphysis of the femur. In a preferred embodiment, prefabricated holes 18b and 18c are constructed in the bridge support 501.

Figure 25:
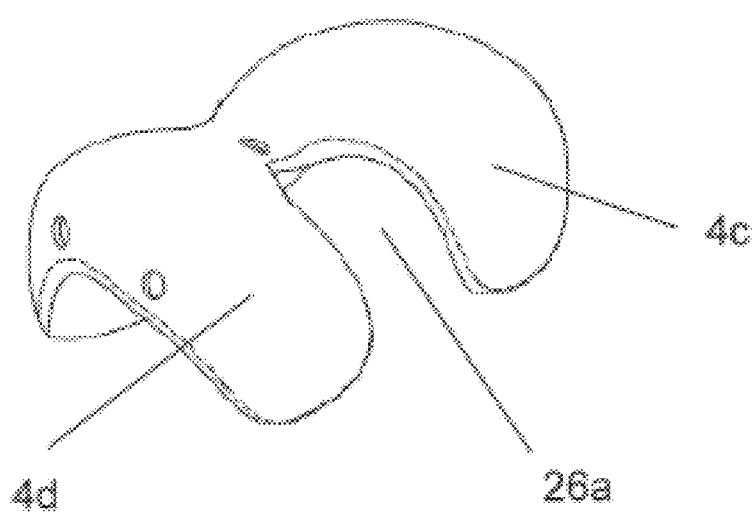
FIG. 25 depicts an oblique view of a right knee implant.

FIG. 25 depicts an implant for a right knee such that appendage 4d hugs a medial condyle of a femur and appendage 4c hugs a lateral condyle of a femur.

Figure 26:
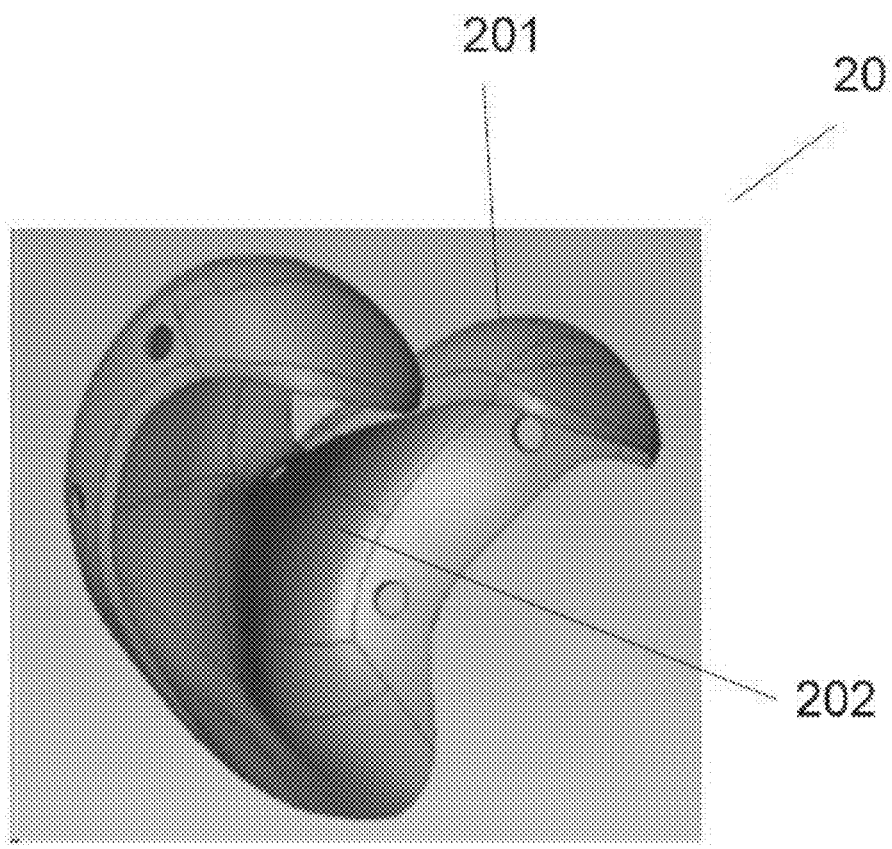
FIG. 26 depicts the bone engaging surface of an implant.

FIG. 26 depicts an implant showing an underside or bone engaging surface 202 of an implant 20. The bone engaging surface 202 may have the same radius of curvature profile as the articulating surface 201. However, the bone engaging surface 202 may have microfeatures such as indents, divits, contours, grooves, vacuoles or other irregularities to allow for bone in-growth and fixation of the implant to the bone and/or remaining cartilage.

FIG. 27 shows an isometric view of an implant for a left knee. Line RLL is a dimensioned reference line on the medial side of implant 20 and RLM is a dimensioned reference line on the lateral side of implant 20. Dimensioned reference line RLM extends from an anterior part of the implant periphery 401 to a posterior part of the implant periphery 402. Dimensioned reference line RLL extends from an anterior part of the implant periphery 401 to a posterior part of the implant periphery 402. The dimensional measurements along RLL may be different from those along RLM. Not shown is an implant design for a right knee with dimensioned reference lines. Dimensional measurements for an implant for a right knee may be the same or different than those for a left knee.

Figure 28:
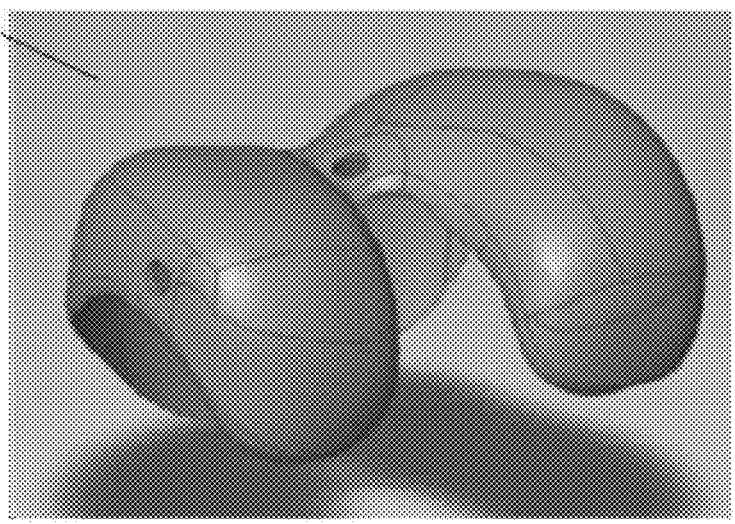
FIG. 28 depicts a posterior view of implant 20.

FIG. 28 depicts a posterior view of implant 20.

Figure 29:
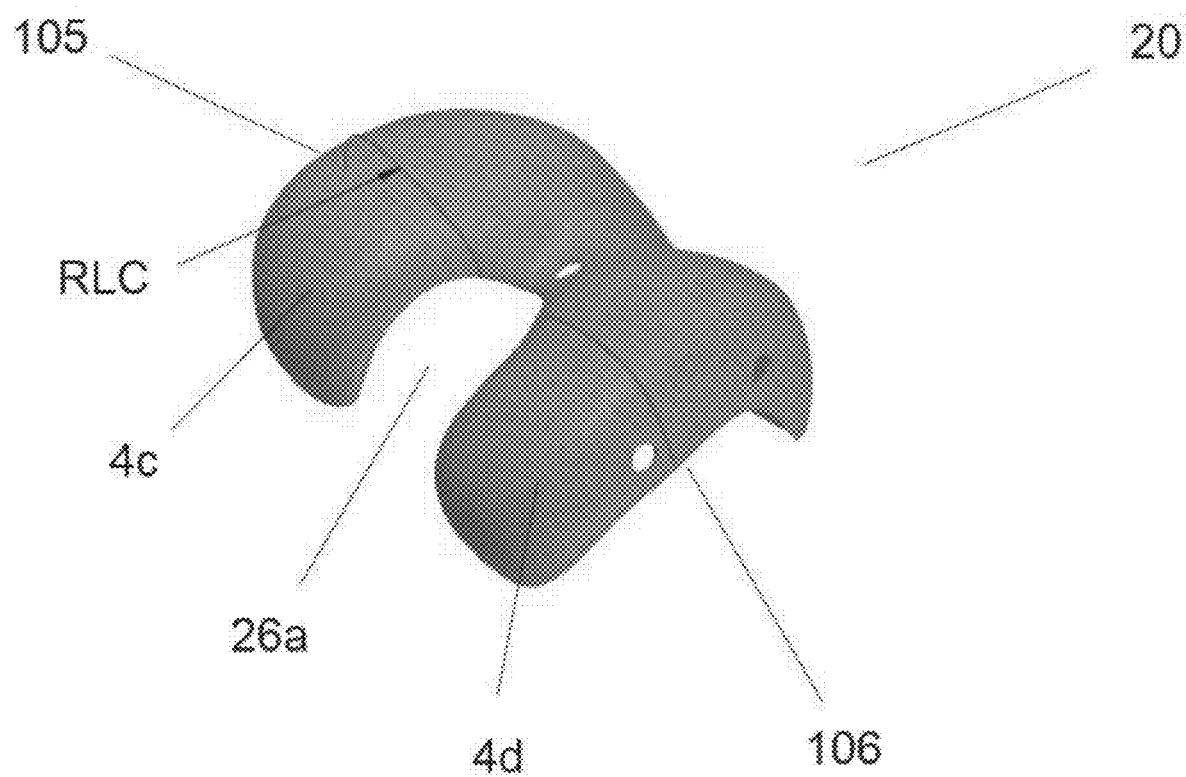
FIG. 29 depicts an oblique posterior view of the joint articulating surface of an implant.

FIG. 29 depicts an isometric view of an implant having a dimensioned reference line RLC. Dimensioned reference line RLC may extend from a lateral portion 106 of appendage 4d to a medial portion 105 of appendage 4c. The dimensional measurements along RLC may be the same or different for appendage 4d and appendage 4c. In one embodiment, the radial curvature profile for the appendage hugging and/or engaging the medial condyle may be different than the radial curvature profile for the appendage hugging and/or engaging the lateral condyle along dimensioned reference line RLC. Curvature profiles along dimensioned reference line RLC may be different for implants fabricated for right knees than curvature profiles along dimensioned reference line RLC for implants fabricated for left knees.

Example 1

Radius of curvature measurements can be taken along the cutaway profiles of the implant. An implant was designed for a sample left femur. Models were created from a 3D model of a SawBones femur. A sketch line was created along the distal end of the femur that follows the articular cartilage. After an acceptable outline was created, a surface of the femur was copied from within the outline. The next step was to thicken and extrude a single polymer layer of thermoplastic to a 1.0 mm thickness. This particular implant design had a filleted rim which was not included in the radius of curvature measurements. The radius of curvature was measured for both the joint articulating surface and the bone engaging surface. The segment lengths or arc lengths used for the basis of measurement for the joint articulating surface of the implant were 10.33 mm. The segment lengths or arc lengths used for the basis of measurement for the bone engaging surface were 10 mm. The segments lengths were taken along a dimensioned reference line similar to that of line RLM of FIG. 27 starting from an anterior point to a posterior point on the implant periphery. The segments along the joint articulating surface were numbered from 1-11 wherein the first segment was measured starting from an anterior point on the implant periphery, not including a filleted rim area. The segments along the bone engaging surface were numbered from 12-22 wherein the twelfth segment was measured starting from an anterior point on the implant periphery, not including a filleted rim area. Segments or arc lengths were measured and the radius of curvature for each arc length is provided in Table 1 and Table 2.

TABLE 1

| Segments - articulating surface | Radius of Curvature Value (radius in mm) |
| --- | --- |
| Segment 1 | 183.17 |
| Segment 2 | 26.48 |
| Segment 3 | 26.53 |
| Segment 4 | 23.28 |
| Segment 5 | 38.31 |
| Segment 6 | 65.30 |
| Segment 7 | 38.63 |
| Segment 8 | 30.74 |
| Segment 9 | 21.76 |
| Segment 10 | 15.36 |
| Segment 11 | 51.39 |

TABLE 2

| Segments - bone engaging surface | Radius of Curvature Value (radius in mm) |
| --- | --- |
| Segment 12 | 141.91 |
| Segment 13 | 26.58 |
| Segment 14 | 23.89 |
| Segment 15 | 22.05 |
| Segment 16 | 39.23 |
| Segment 17 | 60.95 |
| Segment 18 | 39.84 |
| Segment 19 | 28.71 |
| Segment 20 | 19.29 |
| Segment 21 | 14.67 |
| Segment 22 | 34.7 |

Figure 30:
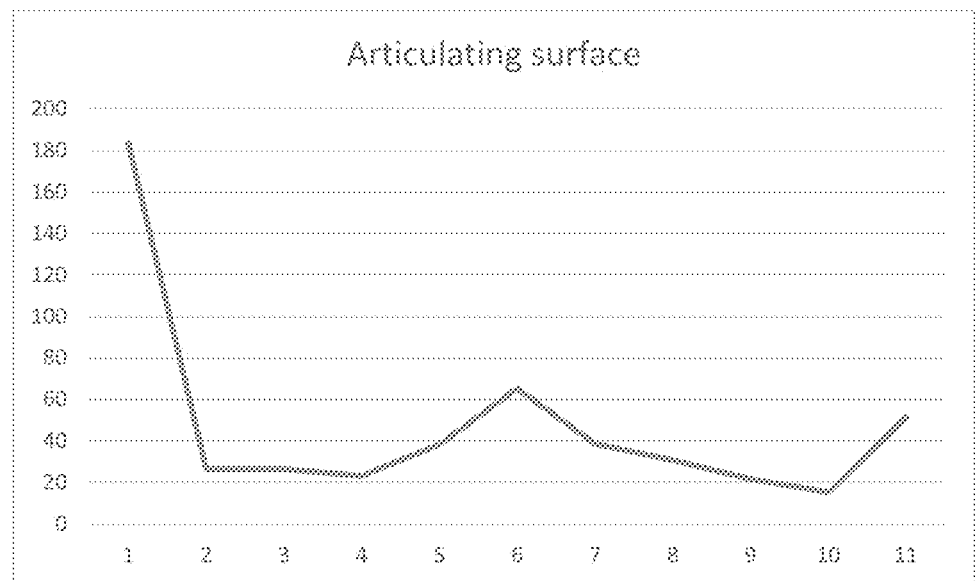
FIG. 30 is a graph of the radius of curvature profile of a joint articulating surface along a lateral dimensioned reference line of an implant.
Figure 31:
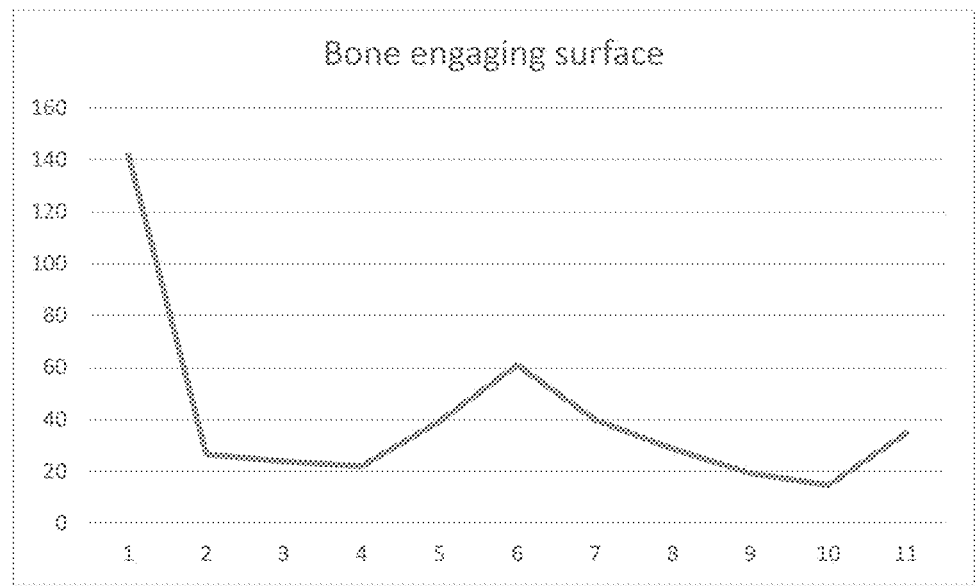
FIG. 31 is a graph of the radius of curvatures profile of a bone engaging surface along a lateral dimensioned reference line of an implant.

The results from Table 1 as graphed is shown in FIG. 30 and the results from Table 2 as graphed are shown in FIG. 31. FIG. 30 and FIG. 31 demonstrate that the radius of curvature profiles for both the articulating surface and the joint engaging surface are very similar. The similarity has to do in part with the consistent thickness of the implant and/or the average thickness of the implant.

Figure 32A:
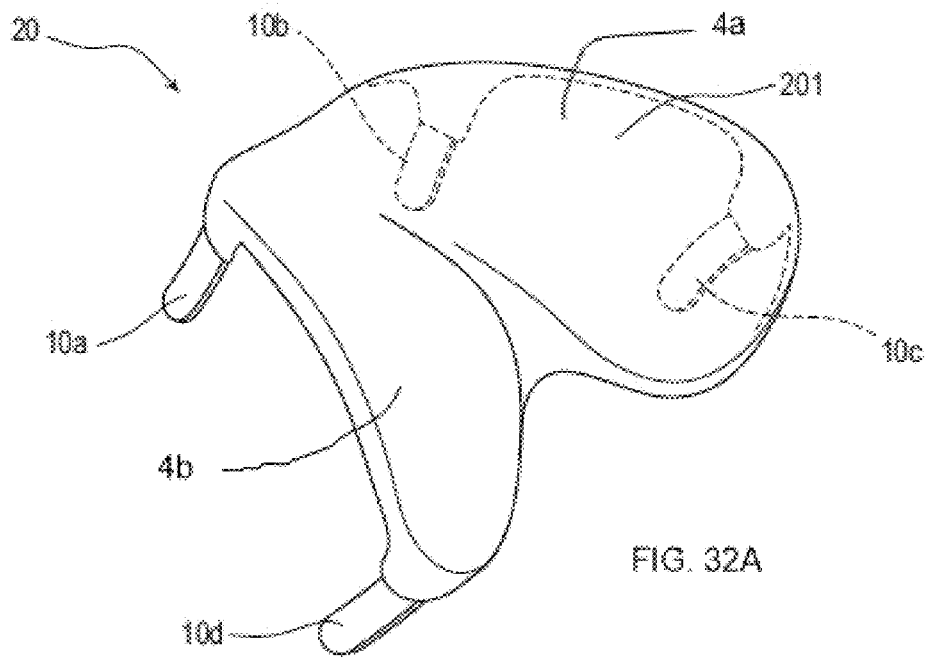
FIGS. 32A and 32B depict the bone engaging surface of a trochlear implant with tabs and preformed holes.

FIG. 32A depicts an implant 20 fitted for the trochlear groove of a knee joint having tabs 10a, 10b, 10c, 10d. As for any embodiments herein, additional tabs may be present or fewer tabs may be present depending on the requirements for best fit for a particular patient. Although tabs may be manufactured at any feasible location around the implant, one tab 10a may be located to fit into the intercondylar notch. The tabs may include preformed holes or slots (not shown) to accommodate couplers as described elsewhere herein. FIG. 32A may or may not comprise a chamber which, if the implant were shown in cross section, may comprise a several materials which may be the same as or different from any wall of the implant itself, or may be the same material but with different geometric or chemical or physical properties, as noted herein. The implant may be sized to fit a particular patient and may also be modified in some respects to fit particular knee shapes and sizes. The implant of FIG. 32A may be designed to fit or hug the trochlear groove and may be designed with the appropriate elasticity to hug or hold on to the trochlear groove. The implant may be a single polymeric layer. Articulating surface 201 engages the joint space and underside surface is a bone engaging surface. In preferred embodiments, the bone engaging surface is the surface that engages the femur, natural cartilage or remaining cartilage that is present on the end of the femur. The implant may be inserted into the knee as described elsewhere herein. In one embodiment, the implant has appendages 4a and 4b which may be different in shape and/or size to accommodate differences in trochlear groove size and/or shape.

Figure 32B:
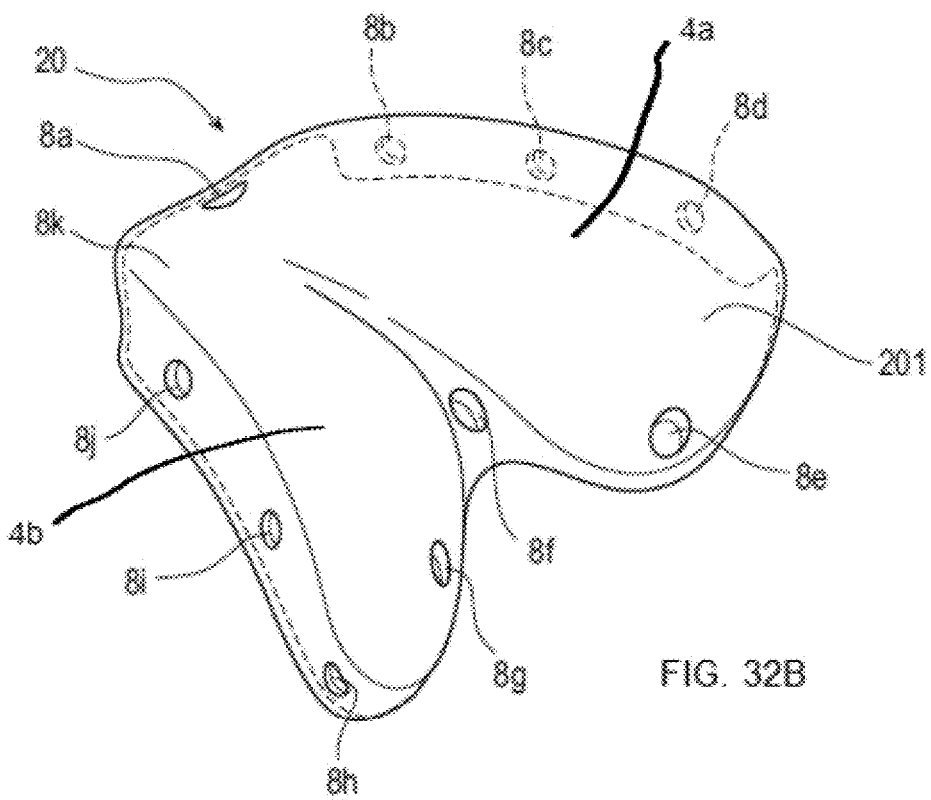

FIG. 32B depicts an implant 20 fitted for the trochlear groove of a knee joint having pre-fabricated holes 8a, 8b, 8c, 8c, 8d, 8e, 8f, 8g, 8h, 8i, 8j, 8k. As for any embodiments herein, additional pre-fabricated holes may be present or fewer pre-fabricated holes may be present depending on the requirements for best fit for a particular patient. Couplers as described elsewhere herein may be used to couple the implant 20 to the distal femur through slots or holes 8a-8k. FIG. 32B may or may not comprise a chamber which, if the implant were shown in cross section, may comprise a several materials which may be the same as or different from any wall of the implant itself, or may be the same material but with different geometric or chemical or physical properties, as noted herein. The implant may be sized to fit a particular patient and may also be modified in some respects to fit particular knee shapes and sizes. The implant of FIG. 32B may be designed to fit or hug the trochlear groove and may be designed with the appropriate elasticity to hug or hold on to the trochlear groove. The implant may be a single polymeric layer. Articulating surface 201 engages the joint space and underside surface is a bone engaging surface. In one embodiment, the implant has appendages 4a and 4b which may be different in shape and/or size to accommodate differences in trochlear groove size and/or shape. In preferred embodiments, the bone engaging surface is the surface that engages the femur, natural cartilage or remaining cartilage that is present on the end of the femur. The implant may be inserted into the knee as described elsewhere herein.

An implant similar to those in FIGS. 32A and 32B can be fitted for the retropatellar surface of a knee joint having tabs 10a, 10b, 10c, 10d. Tabs may be manufactured at any feasible location around the implant and may include additional tabs. The tabs may include preformed holes or slots (not shown) to accommodate couplers as described elsewhere herein. The implant may be sized to fit a particular patient and may also be modified in some respects to fit particular knee shapes and sizes or to accommodate ligaments and/or other knee structures. The implant of FIG. 32A may be designed to fit or hug the patella and may be designed with the appropriate elasticity to hug or hold on to the patella with the appropriate shape to mimic the natural cartilage. The implant may be a single polymeric layer. Articulating surface 201 engages the joint space and underside surface is a bone engaging surface. In preferred embodiments, the bone engaging surface is the surface that engages the patella, natural cartilage or remaining cartilage that is present. The implant may be inserted into the knee as described elsewhere herein.

An implant similar to FIG. 32B can be fitted for the retropatellar surface of a knee joint having pre-fabricated holes 8a, 8b, 8c, 8d, 8e, 8f, 8g, 8h, 8i, 8j, 8k. Couplers as described elsewhere herein may be used to couple the implant 20 to the patella through slots or holes 8a-8k. FIG. 33B may or may not comprise a chamber which, if the implant were shown in cross section, may comprise a several materials which may be the same as or different from any wall of the implant itself, or may be the same material but with different geometric or chemical or physical properties, as noted herein. The implant may be sized to fit a particular patient and may also be modified in some respects to fit particular knee shapes and sizes or to accommodate ligaments and/or other knee structures. The implant of FIG. 33B may be designed to fit or hug the patella and may be designed with the appropriate elasticity to hug or hold on to the patella. The implant may be a single polymeric layer. Articulating surface 201 engages the joint space and underside surface is a bone engaging surface. In preferred embodiments, the bone engaging surface is the surface that engages the patella, natural cartilage or remaining cartilage that is present. The implant may be inserted into the knee as described elsewhere herein.

In some embodiments, the implant is configured such that the tabs and/or couplers of the implant couple to the bone where there is no natural cartilage. In some embodiments, the implant may be adapted by the surgeon at the time of surgery such that the tabs are positioned where there is no natural cartilage.

In some embodiments, the implant comprises a tab and a hook that couples to the tab by wrapping around a component of the knee and securing the tab to the hook. In some embodiments, the implant comprises a tab and a hook that couples to the tab by wrapping around a condyle of the knee and securing the tab to the hook. In some embodiments, the implant is configured to wrap around a condyle of the knee and to secure a first appendage to a second appendage of the implant. In some embodiments the appendages are secured by couplers described herein. In some embodiments, the implant is pre-formed to fit to the condyle in such a wrapping manner.

In some embodiments, the implant comprises a methymethacrylate what is placed into a balloon chamber that fits into a bone hole. Such an embodiment would generally fix the implant to the bone once the methymethacrylate cures to a solid.

In some embodiments, the implant can be anchored with generic available sutures and suture anchors fixing and positioning material to bone with proper tensioning.

Ingrowth Features

In addition to the general ingrowth that may occur based on the implant features described herein, the implant undersurface (adjacent the femur) may comprise an ingrowth matrix. In some embodiments, at least a portion of the implant adjacent to the femur comprises bone ingrowth materials. Such an implant can be attached by a series of tabs with or without holes, using screws, rivots, stabilizers, staples, tacks, or Sutures and suture anchors, for non-limiting example. The polymer of the implant substitutes for periosteum when the implant comprises living chondrocytes (e.g. Carticel) as the ingrowth matrix on a surface of the implant. The polymer of the implant substitutes for periosteum when the implant comprises living chondrocytes (e.g. Carticel) as the ingrowth matrix within an implant embodiment configured to reveal and/or release said chondrocytes over time and/or upon implantation.

The bone ingrowth undersurface may be used for long term fixation of the tabs or rim. That is, whereas it is important for the surgery to secure the implant to the joint surface in the most desirable corrective location, it is also important in some embodiments to prepare the anatomic undersurface of bone by abrading it, removing about 0.5 mm of cortical bone so as to expose the underlying oxygen, blood, and nutrients of the patient to the undersurface of the implant that can gradually become incorporated into the limb bone. As this healing occurs over the course of weeks and months to one year post operation, the localized tacking sites may become less relevant and potentially inert. Thus, in some embodiments, the implant may comprise a biodegradable (bioresorbable) polymer or other material. The couplers may additionally and/or alternatively be biodegradable. Once the implant is in place, it will serve to at least one of: pad defects, cushion the joint, and restore the original damage to the joint components. The end goal is to apply minimally morbid treatment that will refurbish arthritic limb regions, leaving only the small skin scar and remote memory of the healed physical mishap.

Undersurface implant materials may involve used of the art and science from Artelon or Gore-Tex research, as each has advantages and limitations. Several implant options per joint damage area may be available to enjoy the primary surgeons manipulation to fit the clinically recovery requirements best.

In some embodiments the implant comprises an ingrowth patch on at least one of the first portion configured to engage the femur, the second portion configured to engage the second bone (whether the tibia or the patella), the side portion, and the appendage. The ingrowth patch may be configured to encourage and/or promote tissue ingrowth, such as bone ingrowth, for non-limiting example. The patch may be as large as the portion itself (whether the first portion the second portion, the side portion, or the appendage) or may be smaller than the portion (such as in the shape of a strip or other shaped patch). The ingrowth patch may comprise a surface irregularity or roughness. The ingrowth patch may be Velcro-like. In some embodiments the implant comprises an ingrowth patch on the first portion and/or the second portion, from (and in some embodiments including)

a first appendage to a second appendage. In some embodiments, wherein the appendages loosen from attachment from the bone (by design and/or from wear and/or over time), the ingrowth patch aids in securing the implant to the bone. In some embodiments, the ingrowth patch comprises beads and/or bead-like elements attached to the implant. Such an ingrowth patch may be configured to simulate trabecular bone space of a normally cancellous latticework. In some embodiments, the beads are sintered beads of various sizes. In some embodiments, the beads are sintered beads about 400 microns in size. With respect to bead size, the term "about" can mean ranges of 1%, 5%, 10%, 25%, or 50%. In some embodiments, the first bone and/or the second bone is roughened to acquire a bleeding bone to facilitate ingrowth. In some embodiments, tissue is removed to facilitate ingrowth.

The walls of the implant embodying features of the invention may be composite structures. For example, the innermost layer may be impervious to preclude escape of inflation or other filling media, a central layer may be porous or otherwise contain treatment or cell regeneration agents, and the outer layer may be a thin, but strong layer of a thermoplastic, such as a thermoplastic polyurethane for non-limiting example, which has microporosity sufficient to allow passage or egress of treatment or cell regeneration agents from the central layer (or second layer). The degree of microporosity to enable egress of treatment or cell regeneration agents from the central layer is found in polymer layers such as Chronoflex or Bionate 55. The external wall (and/or the bone engaging surface) of the implant may be coated and/or impregnated with a latticework of polymer that is surface sprayed or layered on the outside (or bone engaging surface) of the implant to promote cartilage tissue regeneration. This most external surface coating may contain living chondrocytes (for example, as is provided in the Carticel procedure by the Genzyme company), and/or may contain stem cells with or without directed gene mutations to enhance adherence of the coating to the implant. The bone engaging surface may comprise peaks and troughs. The living cells may be imposed in between (and/or provided in the) troughs of the implant surface while the surface areas of prominence (the peaks of the surface) may be used for at least one of: space validation, traction, and cell protection.

The implant embodying features of the invention may be used in a series of treatments wherein the first treatment involves use of autologous or minimally manipulated allograph interpositional tissues or xenograph, the second treatment involves the use of the same type of tissue added to stem cells or chondrocytes and the third treatment involving deployment of the implant if the first two fail or are ineffective.

Pharmacologics and Therapeutic Agents

In some embodiments the implant may comprise vacuoles of pharmacologic substances. The vacuoles may be on a bone-engaging portion of the implant. In some embodiments, the implant comprises bubbles comprising an active substance such as a pharmacologic substance or other active substance. In some embodiments, the implant comprises spaces filled with an active substance such as a pharmacologic substance (pharmacologic agent) or other active substance (active agent). The implant may deliver by dissolution of the implant material (i.e. a biodegradable polymer which releases the active substance), and/or by release through pores of the implant (wherein the polymer is permeable to the active substance), and/or by fracture of the vacuole (or bubble, or space) by a catalyst such as ultrasound or pressure or other fracturing catalyst. The implant may deliver the active substance at a time after the actual implanting of the implant into the joint, for example an hour later, less than a day later, a day later, less than a week later, a week later, less than a month later, and/or a month later. In some embodiments, stem cells that are percolating in the bubble (or vacuole, or space) may be delivered to the joint space (or a constituent of the joint) after the implant is inserted into the joint. Active agents may, for non-limiting example, include stem cells, growth factors, antibiotics, and/or viscolubricants. In some embodiments, the implant may comprise enzyme absorptive 'microscopic sponges' that could be sucked out or evacuated at or around the time of implant delivery to the joint. In some embodiments, the active substance comprises iatrigenically gene mutated cells.

Patient Symptoms

Symptoms for the patient requiring an implant described herein may include, for non-limiting example, osteoarthritis or rheumatoid or gouty arthritis.

Total Knee Arthroplasty (Dual Compartment):

Provided herein is an implant for placement on both condyles (medial and lateral) of the distal femur. In some embodiments, this is called a dual compartment implant since it covers both condyles of the femur. Such an implant comprises at least one interior (or inflatable chamber), and in some embodiments comprises a plurality of inflatable chambers (or interiors).

In some embodiments, the implant will cover the "H" distal femoral cartilage segment (made up of both femoral condyles and the trochlear groove in between). The implant may absorb diffuse force, endure the millions of annual cyclic loads of both knee joints (including the patella-femur joint and the femur-tibia joints), along with rotational and shear forces up to six times body weight, at least.

In some embodiments, the implant comprises attachment tabs or attachment elements over the sides of both condyles medially and laterally. In some embodiments, the implant comprises attachment tabs or attachment elements in the intercondylar notch (or slot). In some embodiments, the implant comprises attachment tabs or attachment elements superiorly at the distal end of the femur anteriorly. In some embodiments, posterior reigns or suture-like lanyards cinch up the implant from inside the posterior intercondylar notch toward another connection site around the femur.

The posterior of the knee can be difficult to access without disturbing joint components (or in order to minimize such disturbance) such as tendons, ligaments, etc. Thus, in some embodiments, the implant comprises strings, reigns, lassos, and/or lanyards that may pass from the posterior of the implant via the intercondylar notch anteriorly to join with themselves and/or other coupling devices. These couplers may be pre-coupled to the implant, and the implant and its couplers may be configured to be pulled (or cinched) from the anterior of the implant once the implant is in its general location relative to the condyle in order to finally position the implant about the condyle—in particular in order to cinch the implant about the posterior of the condyle. Likewise, in some embodiments where the implant is pre-molded, the coupler as described are adapted to move the implant to its final position with conformity to the condyle's posterior with minimal disturbance to the joint structures at the joint's posterior (minimal cutting, minimal moving, and or minimal detachment, for non-limiting example). In some embodiments at least a portion of the ligamentary structure of the knee is spared.

Although this application focuses on the distal femur as it articulates with the retropatellar and proximal tibial cartilages implants as described generally herein may be also and/or alteratively be used in conjunction with the tibia and/or the patella. Furthermore, separate and/or connected implant components may be inserted to restore natural function to the knee.

Coupling devices to be used as part of the dual compartment implant may include any of those mentioned or described herein, for example. Such coupling devices may comprise at least one of strings (i.e. drawstrings), reigns, lassos, sutures, and lanyards. The strings, reigns. lassos, sutures, and/or lanyards may join with themselves and/or other coupling devices. The strings, reigns. lassos, sutures and/or lanyards may be directed not only into bone with or without anchors, but also through ligaments, tendons or loose segments of cartilage that the surgeon intends to preserve.

FIG. 1 depicts an embodiment of the implant 20 in a 2D view configured for dual condyle (distal femur) coverage. FIG. 1 depicts an embodiment of the knee implant 20 having appendages 4a, 4b, 4c, 4d, including holes 8a, 8b, 8c, 8d and tabs 10a, 10b extending from a balloon 6 and including slots 26a, 26b to accommodate ligaments (not shown) of the knee joint. Couplers as described elsewhere herein may be used to couple the implant 20 to the distal femur. In some embodiments, there may only tabs, only holes, or only appendages, or combinations thereof. In some embodiments, there may be other ways to couple the implant to the distal femur, as described elsewhere herein (sutures, drawstrings, skirts, glue, etc). In some embodiments, the couplers create the holes 8a, 8b, 8c, 8d, or other holes (not shown) when the implant is placed against the distal femur 24. In some embodiments, the holes are pre-formed in the appendage prior to implantation. In some embodiments, the holes are reinforced as described elsewhere herein. As shown here, the appendages in some embodiments be different in shape and/or size to accommodate the differences in condyle size and/or shape. For example the medial condyle tends to be larger than the lateral condyle, and thus appendage 4d that is intended to wrap over the medial condyle may be longer and/or wider than the appendage 4c intended to wrap over the lateral condyle. Likewise, the slots may be different in shape and/or size and/or position to accommodate the ligaments and/or tendons of the joint or other structures and functions of the joints of the knee, and to allow for placement of the implant with minimal disturbance (cutting, manipulation, for example) of the joint components such as tendons, ligaments, and other soft or hard tissues. For example, slot 26a is shaped and positioned to accommodate the cruciate ligaments of the knee, at least.

Figure 2:
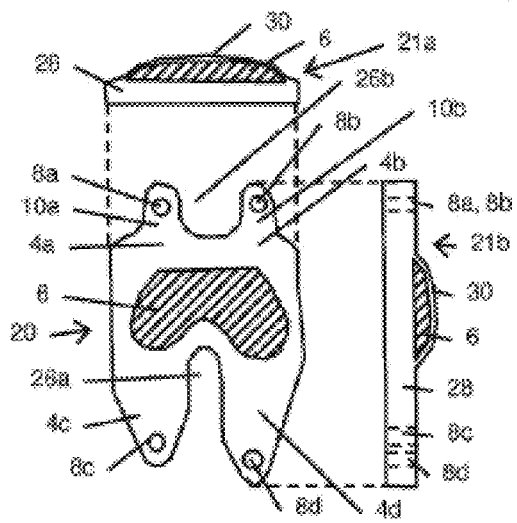
FIG. 2 depicts an embodiment of the knee implant having appendages including holes and tabs extending from a balloon and including slots to accommodate ligaments of the knee joint as well as side views of the same knee implant.

FIG. 2 depicts an embodiment of the knee implant 20 having appendages, 4b, 4c, 4d, including holes 8a, 8b, 8c, 8d and tabs 10a, 10b extending from a balloon 6 and including slots 26a, 26b to accommodate ligaments of the knee joint as well as side views of the same knee implant. Couplers as described elsewhere herein may be used to couple the implant 20 to the distal femur. In some embodiments, there may only tabs, only holes, or only appendages, or combinations thereof. In some embodiments, there may be other ways to couple the implant to the distal femur, as described elsewhere herein (sutures, drawstrings, skirts, glue, etc). In some embodiments, the couplers create the holes 8a, 8b, 8c, 8d, or other holes (not shown) when the implant is placed against the distal femur. In some embodiments, the holes are pre-formed in the appendage prior to implantation. In some embodiments, the holes are reinforced as described elsewhere herein. As shown here, the appendages in some embodiments are different in shape and/or size to accommodate the differences in condyle size and/or shape. For example the medial condyle tends to be larger than the lateral condyle, and thus appendage 4d that is intended to wrap over the medial condyle may be longer and/or wider than the appendage 4c intended to wrap over the lateral condyle. Shown in the embodiment depicted in FIG. 2 are the different hole placements from the side view, showing the differences in positioning of the holes to accommodate the differences in anatomic structure and size of the condyles. Likewise, the slots may be different in shape and/or size and/or position to accommodate the ligaments and/or tendons of the joint or other structures and functions of the joints of the knee, and to allow for placement of the implant with minimal disturbance (cutting, manipulation, for example) of the joint components such as tendons, ligaments, and other soft or hard tissues. For example, slot 26a is shaped and positioned to accommodate the cruciate ligaments of the knee, at least. Additionally, as shown in the side views of the embodiment shown in FIG. 2, the balloon has a first wall 28 adapted to be adjacent the femur that is of a greater thickness than the second wall 30. In some embodiments, the first wall 28 is configured to have therapeutic benefits (pharmacologic, healing, and/or ingrowth properties) as described elsewhere herein. The second wall 30 may additionally and/or alternatively be configured to have a therapeutic effect (pharmacologic, healing, and/or ingrowth properties).

Figure 3:
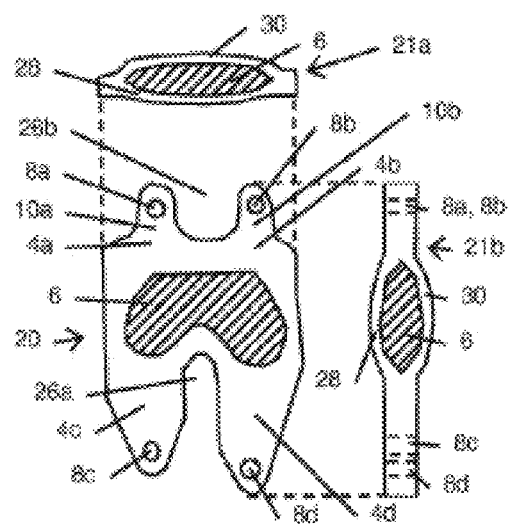
FIG. 3 depicts an embodiment of the knee implant having appendages including holes and tabs extending from a balloon and including slots to accommodate ligaments of the knee joint as well as side views of the same knee implant.

Nevertheless, differing thicknesses of the first wall 28 and the second wall 30 are not necessarily required in order to impart the therapeutic benefits (pharmacologic, healing, and/or ingrowth) described elsewhere herein. For example, FIG. 3 depicts an embodiment of the knee implant 20 having appendages 4a, 4b, 4c, 4d, including holes 8a, 8b, 8c, 8d and tabs 10a, 10b extending from a balloon 6 and including slots 26a, 26b to accommodate ligaments of the knee joint as well as side views of the same knee implant. Couplers as described elsewhere herein may be used to couple the implant 20 to the distal femur. In some embodiments, there may only tabs, only holes, or only appendages, or combinations thereof. In some embodiments, there may be other ways to couple the implant to the distal femur, as described elsewhere herein (sutures, drawstrings, skirts, glue, etc). In some embodiments, the couplers create the holes 8a, 8b, 8c, 8d, or other holes (not shown) when the implant is placed against the distal femur. In some embodiments, the holes are pre-formed in the appendage prior to implantation. In some embodiments, the holes are reinforced as described elsewhere herein. As shown here, the appendages in some embodiments are different in shape and/or size to accommodate the differences in condyle size and/or shape. For example the medial condyle tends to be larger than the lateral condyle, and thus appendage 4d that is intended to wrap over the medial condyle may be longer and/or wider than the appendage 4c intended to wrap over the lateral condyle. Shown in the embodiment depicted in FIG. 3 are the different hole placements from the side view, showing the differences in positioning of the holes to accommodate the differences in anatomic structure and size of the condyles. Likewise, the slots may be different in shape and/or size and/or position to accommodate the ligaments and/or tendons of the joint or other structures and functions of the joints of the knee, and to allow for placement of the implant with minimal disturbance (cutting, manipulation, for example) of the joint components such as tendons, ligaments, and other soft or hard tissues. For example, slot 26a is shaped and positioned to accommodate the cruciate ligaments of the knee, at least. Additionally, as shown in the side views of the embodiment shown in FIG. 3, the balloon has a first wall 28 adapted to be adjacent the femur that is of approximately the same thickness than the second wall 30. In some embodiments, the first wall 28 is configured to have therapeutic benefits (pharmacologic, healing, and/or ingrowth properties) as described elsewhere herein. The second wall 30 may additionally and/or alternatively be configured to have a therapeutic effect (pharmacologic, healing, and/or ingrowth properties).

Figure 4A:
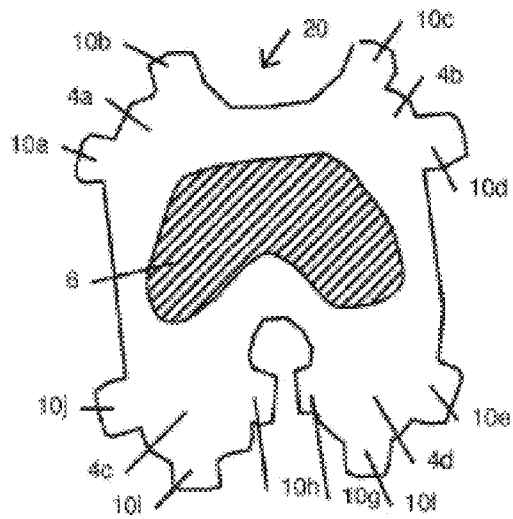
FIG. 4A depicts an embodiment of the knee implant having appendages including ten tabs extending from a balloon and including a slot to accommodate components of the knee joint.
Figure 4B:
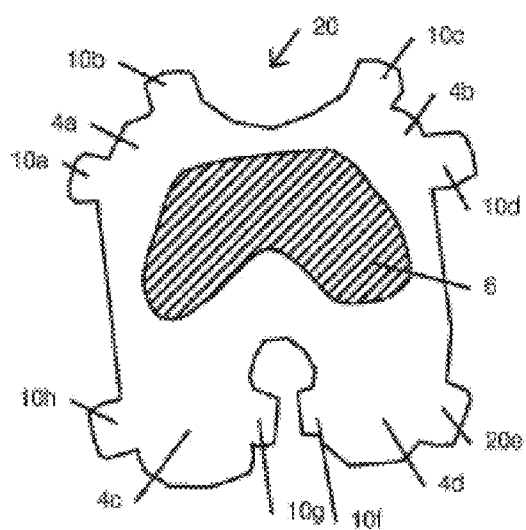
FIG. 4B depicts an embodiment of the knee implant having appendages including eight tabs extending from a balloon and including a slot to accommodate components of the knee joint.

FIG. 4A depicts an embodiment of the knee implant 20 having appendages 4a-4d including ten tabs 10a-10j extending from a balloon 6 and including a slot 26a to accommodate components (such as ligaments or other tissues whether soft tissues, hard tissues, tendons, and/or others) of the knee joint (not shown). The tabs 10a-10j are not shown with holes in this embodiment, however if screws are used as couplers, such holes may be pre-drilled or formed in situ by the screws. Additionally and/or alternatively, staples or sutures may be used (as described elsewhere herein) in order to couple the implant to the bone (femur, for example). Other couplers as described elsewhere herein may also and/or alternatively be used in this coupling process. Furthermore, the number of tabs may be fewer or greater than the ten depicted in order to achieve optimal placement and coupling to the bone. For example, FIG. 4B depicts an embodiment of the knee implant 20 having appendages 4a-4d including eight tabs 10a-10h extending from a balloon 6 and including a slot 26a to accommodate components (such as ligaments or other tissues whether soft tissues, hard tissues, tendons, and/or others) of the knee joint (not shown).

Figure 5:
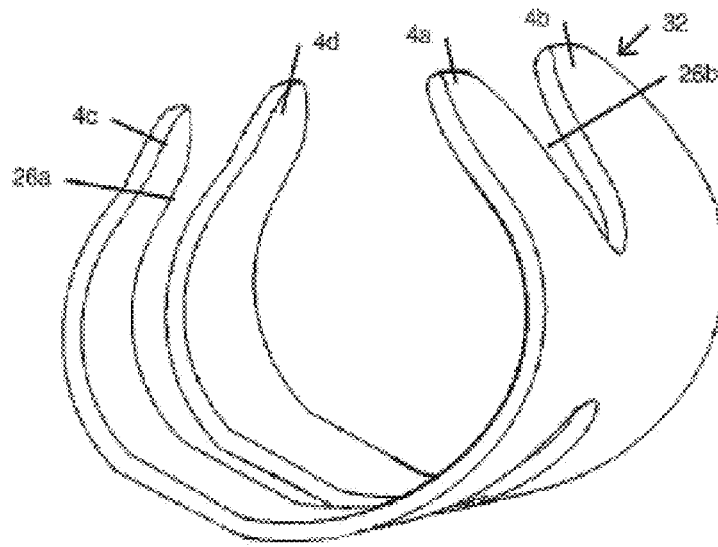
FIG. 5 depicts an embodiment of the knee implant curved to simulate curvature about the condyles of a femur, the implant having appendages extending from an uninflated balloon (not shown) and including slots to accommodate ligaments of the knee joint.

FIG. 5 depicts an embodiment of the knee implant 32 curved to simulate curvature about the condyles of a femur, the implant having appendages 4a-4d extending from an uninflated balloon (not shown) and including slots 26a, 26b to accommodate components (such as ligaments or other tissues whether soft tissues, hard tissues, tendons, and/or others) of the knee joint (not shown). The implant may comprise additional curvatures and/or slots to accommodate other ligaments and/or tissues. In some embodiments, the implant is configured to conform about various hard and/or soft tissues of the joint, such as bone, ligaments, tendons, etc. In some embodiments, the balloon is inflated once the implant is positioned within the joint. In other embodiments, the balloon is partially inflated prior to being positioned within the joint. In other embodiments, the balloon is at least partially inflated prior to being positioned within the joint. In some embodiments, the balloon is fully inflated prior to being positioned within the joint. In some embodiments, the implant is configured to allow an operator to adjust the amount of balloon inflation in situ (whether by adding inflation medium or removing inflation medium, or both, or neither). Couplers as described elsewhere herein may be used to couple the implant 32 to the distal femur.

Figure 6A:
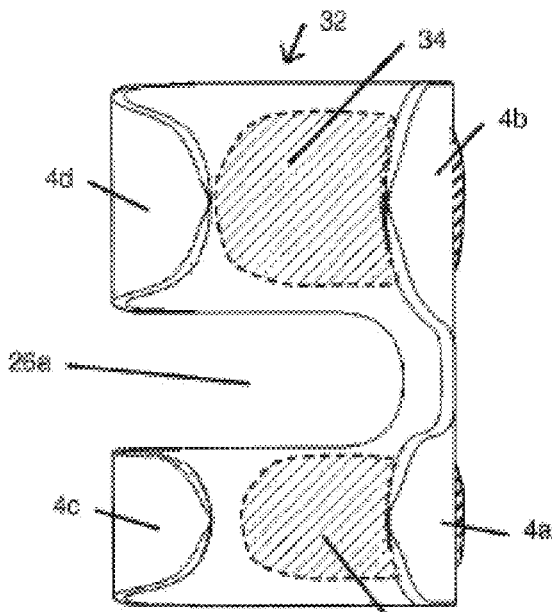
FIG. 6A depicts a top-down view of an embodiment of the knee implant curved to simulate curvature about the condyles of a femur, the implant having appendages extending from two inflated balloons and including slots to accommodate components of the knee joint.
Figure 6B:
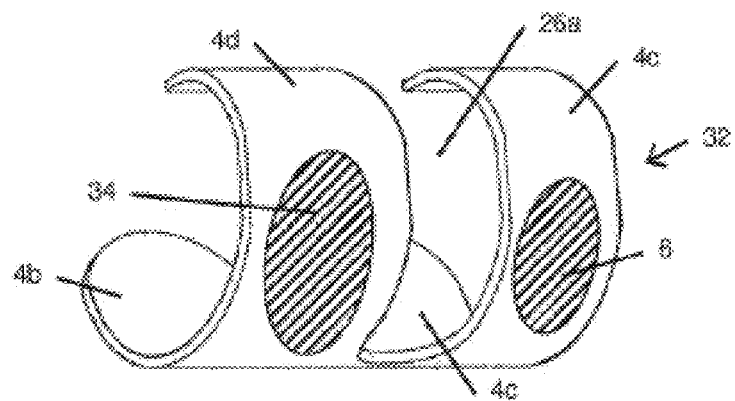
FIG. 6B depicts a bottom-up view of an embodiment of the knee implant curved to simulate curvature about the condyles of a femur, the implant having appendages extending from two inflated balloons and including slots to accommodate components of the knee joint.

FIG. 6A depicts a top-down view of an embodiment of the knee implant 32 curved to simulate curvature about the condyles of a femur, the implant having appendages 4a-4d extending from two inflated balloons 6, 34 and including a slot 26a to accommodate components of the knee joint. FIG. 6B depicts a bottom-up or anterior oblique view of the same embodiment of the knee implant 32 curved to simulate curvature about the condyles of a femur, the implant having appendages 4a-4d extending from two inflated balloons 6, 32 and including a slot 26a to accommodate components of the knee joint. Couplers as described elsewhere herein may be used to couple the implant 32 to the distal femur. As shown in FIGS. 6A and 6B, the appendages 4a-4d in some embodiments are different in shape and/or size to accommodate the differences in condyle size and/or shape. For example the medial condyle tends to be larger than the lateral condyle, and thus appendage 4d that is intended to wrap over the medial condyle may be longer and/or wider than the appendage 4c intended to wrap over the lateral condyle. Likewise, the dimensions of the balloon 34 that is adapted for placement over the medial condyle may be a different shape and/or size than the balloon 6 over the lateral condyle (the medial condyle being larger, thus the balloon 34 may be larger for that location) Alternatively and/or additionally, as described elsewhere herein, for various reasons such as injury, realignment needs, injury, etc, there may be a need for more reconstruction of one condyle than needed for the other, thus the inflation medium might be different in one balloon (or a portion thereof) than in the other balloon (or another chamber within the same balloon), or there may be need for a different shaped balloon in one location than in another location. Embodiments provided herein can accommodate these requirements based on materials of fillers, appendages, balloons, walls, and dimensions and chamber options of the implant and its components.

Figure 7:
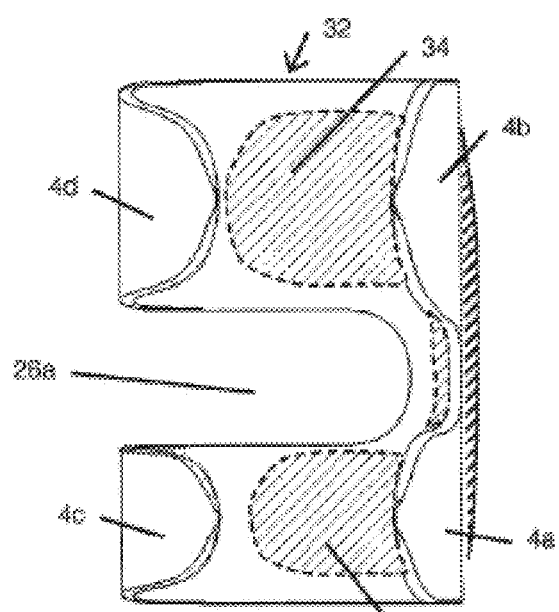
FIG. 7 depicts a top-down view of an embodiment of the knee implant curved to simulate curvature about the condyles of a femur, the implant having appendages extending from an inflated balloon and including slots to accommodate components of the knee joint.

FIG. 7 depicts a top-down view of an embodiment of the knee implant 32 curved to simulate curvature about the condyles of a femur, the implant having appendages 4a-4d extending from an inflated balloon 6 and including slots to accommodate components of the knee joint. Couplers as described elsewhere herein may be used to couple the implant 32 to the distal femur. As shown here, the appendages 4a-4d in some embodiments are different in shape and/or size to accommodate the differences in condyle size and/or shape. For example the medial condyle tends to be larger than the lateral condyle, and thus appendage 4d that is intended to wrap over the medial condyle may be longer and/or wider than the appendage 4c intended to wrap over the lateral condyle. Likewise, the dimensions of the portion of the balloon that is adapted for placement over the medial condyle may be a different shape and/or size than the portion of the balloon over the lateral condyle (the medial condyle being larger, thus the balloon may be larger for that location) Alternatively and/or additionally, as described elsewhere herein, for various reasons such as injury, realignment needs, injury, etc, there may be a need for more reconstruction of one condyle than needed for the other, thus the inflation medium might be different in a portion or chamber of an implant embodiment having a plurality of inflation chambers in a single balloon, or there may be need for a non-symmetric balloon. Embodiments provided herein can accommodate these requirements based on materials of fillers, appendages, balloons, walls, and dimensions and chamber options of the implant and its components.

Figure 8:
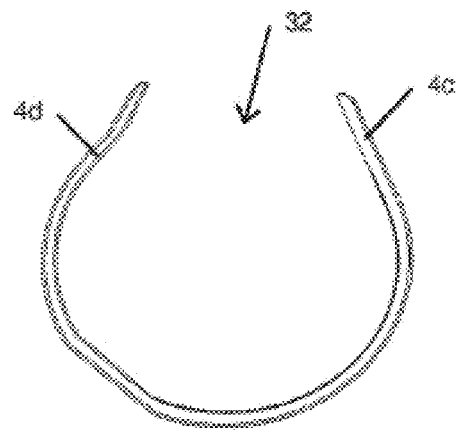
FIG. 8 depicts a side view of an embodiment of the knee implant curved to simulate curvature about at least one condyle of a femur, the implant having appendages extending from an uninflated balloon (not shown).

FIG. 8 depicts a side view of an embodiment of the knee implant 32 curved to simulate curvature about at least one condyle of a femur, the implant having appendages 4b, 4d extending from an uninflated balloon (not shown). This depiction covers the maximum anticipated distal femoral contour; other iterations may be smaller, or shorter covering limited areas of the circumference of the femoral curvatures.

FIG. 9A depicts a side view of an embodiment of the knee implant 20 curved about at least one condyle 22 of a femur 24, the implant 20 having appendages 4b, 4d extending from an uninflated or minimally inflated balloon 6. In this view, the knee is positioned essentially in extension (straight), showing the tibia 36, fibula 38, and patella 40 of the knee. Note that although there would be other joint structures and knee structures in a true depiction of an implant positioned in the knee, this view of the implant and bones is greatly simplified for ease of understanding of the implant and the joint relative (and approximate) positions and placement. Couplers as described elsewhere herein may be used to couple the implant 20 to the distal femur 24 and/or the condyle 22 thereof (in this image the medial condyle, at least since it is primarily a one-side view of the joint and implant). For the sake of simplicity FIG. 9A and the implant embodiment depicted show of the femur with opposition to the other surfaces of both knee joints (between femur and tibia, and femur and patella), the areas of contact varying according to activity, forces, and range of motion. Other implant iterations may apply to opposing surfaces.

FIG. 9B depicts a side view of an embodiment of the knee implant 20 curved about at least one condyle 22 of a femur 24, the implant 20 having appendages 4b, 4d extending from an inflated balloon 6. In this view, the knee is positioned essentially in extension (straight), showing the tibia 36, fibula 38, and patella 40 of the knee. Note that although there would be other joint structures and knee structures in a true depiction of an implant positioned in the knee, this view of the implant and bones is greatly simplified for ease of understanding of the implant and the joint relative (and approximate) positions and placement. Couplers as described elsewhere herein may be used to couple the implant 20 to the distal femur 24 and/or the condyle 22 thereof (in this image the medial condyle, at least since it is primarily a one-side view of the joint and implant). In FIG. 9B wherein the balloon is inflated, as compared to FIG. 9A wherein the balloon is not inflated or is minimally inflated, the balloon second wall 30 is closer to and/or contacting the tibial plateau 42 (articular surface) when the balloon 6 is inflated. Likewise, FIG. 9C depicts a side view of an embodiment of the knee implant 20 curved about at least one condyle 22 of a femur 24, the implant 20 having appendages 4b, 4d extending from an inflated balloon 6 and having couplers 44a, 44b (which may be, for non-limiting example, staples or screws) coupling the appendages 4b, 4d to the femur. In this view, the knee is positioned essentially in extension (straight), showing the tibia 36, fibula 38, and patella 40 of the knee. Where the inflated balloon as seen in FIG. 9B may fill in existing pathologic defects of the joint surface, the medium of inflated and specific balloon location and durometry with the material of the implant may also be constructed so as to force the bones opposed, e.g. the femur and tibia, into a more natural limb alignment such as six (6) degrees valgus. However, if the patient being treated has variations from normal in the affected knee as illustrated by examining and measuring the opposite normal side, then the implant inflation and pressures or balloon location may be adjusted from the population norms thus customizing this implant to the clinical case under consideration. Fixation devices may be appropriately applied at various knee range of motion intervals from full extension (zero degrees) to full flexion (usually 135 degrees) as the knee is adjusted and the implant secured under anesthesia.

FIG. 10A depicts a side view of an embodiment of the knee implant 20 curved about at least one condyle 22 of a femur 24, the implant 20 having appendages 4b, 4d extending from an inflated balloon 6 and showing the inflation medium 46 moved anteriorly toward the patella 40 when the knee joint is slightly flexed. Likewise, FIG. 10B depicts a side view of an embodiment of the knee implant 20 curved about at least one condyle 22 of a femur 24, the implant 20 having appendages 4b, 4d extending from an inflated balloon 6 and having couplers 44a, 44b (which may be, for non-limiting example, staples or screws) coupling the appendages 4b, 4d to the femur 24 and showing the inflation medium 46 moved anteriorly toward the patella 40 when the knee joint is slightly flexed.

In all descriptions provided herein of the dual compartment implant, the implant may instead be configured to couple to or emerge from the tibia and/or patella. In all descriptions provided herein of the dual compartment implant, the implant may instead be configured to couple to the tibia. It is the intention and understanding that the implant is suited for this purpose in certain embodiments with adjustments to account for dimensional differences of the tibia. Most descriptions provided herein are directed to embodiments coupling the implant to the femur, however, this is primarily for ease of description and continuity, and does not preclude embodiments wherein the implant is coupled to the tibia. Likewise, as noted elsewhere herein, there are embodiments where the implant may be coupled to two bones (at least), for example to both a tibia and a femur.

Patch

Some embodiments of the implant are configured to repair isolated lesions wherein osteochondral defects as in osteonecrosis create craters in the cartilage that need 'filling in' with a patch. Various size lesions of cartilage defects can be accommodated by the implants provided herein which may have balloons of at least one of: at most about 0.5 cm in diameter, at most about 0.75 cm in diameter, at most about 1 cm in diameter, at most about 1.25 cm in diameter, at most about 1.5 cm in diameter, at most about 1.75 cm in diameter, at most about 2 cm in diameter, at most about 2.25 cm in diameter, at most about 2.5 cm in diameter, at most about 2.75 cm in diameter, at most about 3 cm in diameter, at most about 3.25 cm in diameter, at most about 3.5 cm in diameter, at most about 3.75 cm in diameter, at most about 0.5 cm in length along the longest length of the balloon, at most about 0.75 cm in length along the longest length of the balloon, at most about 1 cm in length along the longest length of the balloon, at most about 1.25 cm in length along the longest length of the balloon, at most about 1.5 cm in length along the longest length of the balloon, at most about 1.75 cm in length along the longest length of the balloon, at most about 2 cm in length along the longest length of the balloon, at most about 2.25 cm in length along the longest length of the balloon, at most about 2.5 cm in length along the longest length of the balloon, at most about 2.75 cm in length along the longest length of the balloon, at most about 3 cm in length along the longest length of the balloon, at most about 3.25 cm in length along the longest length of the balloon, at most about 3.5 cm in length along the longest length of the balloon, at most about 3.75 cm in length along the longest length of the balloon, at most about 4 cm in length along the longest length of the balloon, at most about 4.25 cm in diameter, at most about 4.5 cm in diameter, at most about 4.75 cm in diameter, at most about 5 cm in diameter, at most about 5.25 cm in diameter, at most about 5.5 cm in diameter, at most about 5.75 cm in diameter, at most about 6 cm in diameter, at most about 6.25 cm in diameter, at most about 6.5 cm in diameter, at most about 6.75 cm in diameter, at most about 7 cm in diameter, at most about 7.25 cm in diameter, at most about 7.5 cm in diameter, at most about 7.75 cm in diameter, at most about 8 cm in diameter, at most about 3 cm in length along the longest length of the balloon, at most about 3.25 cm in length along the longest length of the balloon, at most about 3.5 cm in length along the longest length of the balloon, at most about 3.75 cm in length along the longest length of the balloon, at most about 4 cm in length along the longest length of the balloon, at most about 4.25 cm in length along the longest length of the balloon, at most about 4.5 cm in length along the longest length of the balloon, at most about 4.75 cm in length along the longest length of the balloon, at most about 5 cm in length along the longest length of the balloon, at most about 5.25 cm in length along the longest length of the balloon, at most about 5.5 cm in length along the longest length of the balloon, at most about 5.75 cm in length along the longest length of the balloon, at most about 6 cm in length along the longest length of the balloon, 6.25 cm in length along the longest length of the balloon, at most about 6.5 cm in length along the longest length of the balloon, at most about 6.75 cm in length along the longest length of the balloon, at most about 7 cm in length along the longest length of the balloon, at most about 7.25 cm in length along the longest length of the balloon, at most about 7.5 cm in length along the longest length of the balloon, at most about 7.75 cm in length along the longest length of the balloon, and at most about 8 cm in length along the longest length of the balloon. As used herein with respect to balloon dimensions whether length or diameter, the term "about" means variations of at least one of 0.1 cm, 0.2 cm, 0.25 cm, 0.5 cm, and 1 cm.

Thus, provided herein is an implant configured to patch osteochondral defects. The defects may occur due to injury, stress, naturally occurring, and/or may created or enhanced by a medical professional during a medical procedure. In some embodiments, the implant may be called a patch having the balloon and an attachment element (or elements—which may be called appendages) described herein and may be sized to fit within a defect in a manhole-cover type manner. In some embodiments, the implant may comprise balloon and attachment elements described elsewhere herein and may be configured to lay over a defect (full defect or partial defect). In some embodiments the implant as described herein as used to patch or repair osteochondral defects may be called a patch or a patch implant.

In some embodiments, the size of the balloon dimensions are prechosen based on the individual patient need, and the balloon size (dimensions, geometry, length, depth, for non-limiting examples) is pre-set. In some embodiments, the balloon comprises multiple chambers which may be inflated (or deflated) selectively to fill the defect in situ or just prior to implantation in order to adjust the implant's balloon size (dimensions, length, width, depth, geometry, for non-limiting example) as needed at the time of implantation. The balloon (or any chamber thereof) of some embodiments can be secondarily inflated or deflated (or both) in situ.

FIGS. 11A, 11B, and/or 11O may be used to describe a patch implant described herein, having appendages 4a, 4c, extending from a balloon 6 (not shown in FIG. 11A) and including holes 8a-8h, and/or tabs 10a-10f which may be used with couplers (not shown) to couple the implant to a bone of the knee joint (which may be the femur, the tibia, or the patella). Features shown in FIGS. 11A, 11B, and/or 11O are common to both the unicompartment knee implant (discussed elsewhere herein) and the patch implant, although dimensions may differ as described herein. Thus, FIGS. 11A, 11B, and/or 11O may be used to describe the unicompartment knee implant and/or the patch implant. FIG. 11A depicts an embodiment of the patch implant 2 curved to simulate curvature about one condyle of a femur, the implant 2 having appendages 4a, 4c, extending from an uninflated balloon (not shown) and including tabs 10a-10f and/or holes 8a-8h, which may be used with couplers (not shown, described elsewhere herein) to couple the implant 2 to the femur of the knee joint. FIG. 11B depicts an embodiment of the patch implant 2 curved to simulate curvature about one condyle of a femur, the implant 2 having appendages 4a, 4c, extending from an inflated balloon 6 and including tabs 10a-10f and/or holes 8a-8h, which may be used with couplers (not shown, described elsewhere herein) to couple the implant 2 to the femur of the knee joint. FIGS. 11A and 11B can also be fitted to resurface a lateral and/or medial tibial plateau. FIG. 11C depicts a bottom-up of gliding surface view of an embodiment of the patch implant 2 curved to simulate curvature about one condyle of a femur, the implant 2 having appendages 4a, 4c, extending from an inflated balloon 6 and including tabs 10a-10f and/or holes 8a-8h, which may be used with couplers (not shown, described elsewhere herein) to couple the implant 2 to the femur of the knee joint. In some embodiments, the implant is configured to couple to a tibia. In some embodiments, the implant is configured to couple to a trochlear groove of a femur. In some embodiments, the implant is configured to couple to only a portion of a condyle of a femur.

FIGS. 12A, 12B, and/or 12C may be used to describe a patch implant described herein, having appendages 4a, 4c, extending from a balloon 6 and including holes 8a, 8b, 8c, and/or tabs 10a, 10b. 10c, 10d, 10e, 10f which may be used with couplers (not shown) to couple the implant to a bone of the knee joint (which may be the femur, the tibia, or the patella). Features shown in FIGS. 12A, 12B, and/or 12C are common to both the unicompartment knee implant (discussed elsewhere herein) and the patch implant, although dimensions may differ as described herein. Thus, FIGS. 12A, 12B, and/or 12C may be used to describe the unicompartment knee implant and/or the patch implant. FIG. 12A depicts a bottom-up view of an embodiment of the implant 2 (unicompartment or patch), the implant having appendages 4a, 4c, extending from a balloon 6 and including holes 8a, 8b, 8c, which may be used with couplers (not shown) to couple the implant 2 to the femur of the knee joint. FIG. 12B depicts a bottom-up view of an embodiment of the implant 2 (unicompartment or patch), the implant having appendages 4a, 4c, extending from a balloon 6 and including tabs 10a, 10b and hole 8a which may be used with couplers (not shown) to couple the implant to the femur of the knee joint. FIG. 12C depicts a bottom-up view of an embodiment of the implant 2 (unicompartment or patch), the implant having appendages 4a, 4c, extending from a balloon 6 and including tabs 10c, 10d, 10e, and 10f and hole 8a which may be used with couplers (not shown) to couple the implant to the femur of the knee joint. In some embodiments, the implant is configured to couple to a tibia. In some embodiments, the implant is configured to couple to a trochlear groove of a femur. In some embodiments, the implant is configured to couple to only a portion of a condyle of a femur. In some embodiments the implant is coupled to the patella. In any embodiment the balloon 6 may extend from one surface of the implant as a focal protuberance to fill a defect, space, or to aide in alignment correct, or the balloon may be full thickness as differences in FIGS. 2 and 3 show respectively. In any embodiment there may be a singular or multiple major balloons, if off a primary surface resembling bubble wrap, and there may be microscopic balloons or vacuoles containing gas, gel, or solid in the material matrix.

In all descriptions provided herein of the patch implant, the implant may instead be configured to couple to the tibia or to the fibula or the patella. It is the intention and understanding that the implant is suited for this purpose in certain embodiments with adjustments to account for dimensional differences of these bones. Most descriptions provided herein are directed to embodiments coupling the implant to the femur, however, this is primarily for ease of description and continuity, and does not preclude embodiments wherein the implant is coupled to the tibia (or other bones). Likewise, as noted elsewhere herein, there are embodiments where the implant may be coupled to two bones (at least), for example to both a tibia and a femur.

Partial Knee Arthroplasty (Unicompartment)

In addition to the total knee-type (dual condyle) and patch implants are implants that serve to cover and adjust alignment for either the medial or lateral condyle of the femur with varus or valgus knees requiring added cushioning to recreate the natural six degrees of knee valgus.

Thus, provided herein is an implant for placement on at least one condyle of the distal femur (a unicompartment implant—named so due to their coverage of a single condyle of the femur). The implant may be configured to be placed over the lateral condyle. The implant may be configured to be placed over the medial condyle. The implant may be configured to be placed over either the medial condyle or the lateral condyle. Two unicompartment implants may be placed in the same knee, one over the medial condyle, one over the lateral condyle.

FIGS. 11A-12C depict example embodiments of unicompartment implants. In some embodiments, the unicompartment implant comprises a balloon that is at least one of: at most about 1.5 cm in diameter, at most about 1.75 cm in diameter, at most about 2 cm in diameter, at most about 2.25 cm in diameter, at most about 2.5 cm in diameter, at most about 2.75 cm in diameter, at most about 3 cm in diameter, at most about 3.25 cm in diameter, at most about 3.5 cm in diameter, at most about 3.75 cm in diameter, at most about 4 cm in diameter, at most about 4.25 cm in diameter, at most about 4.5 cm in diameter, at most about 4.75 cm in diameter, at most about 5 cm in diameter, at most about 5.25 cm in diameter, at most about 5.5 cm in diameter, at most about 5.75 cm in diameter, at most about 6 cm in diameter, at most about 6.25 cm in diameter, at most about 6.5 cm in diameter, at most about 6.75 cm in diameter, at most about 7 cm in diameter, at most about 7.25 cm in diameter, at most about 7.5 cm in diameter, at most about 7.75 cm in diameter, at most about 8 cm in diameter, at most about 3 cm in length along the longest length of the balloon, at most about 3.25 cm in length along the longest length of the balloon, at most about 3.5 cm in length along the longest length of the balloon, at most about 3.75 cm in length along the longest length of the balloon, at most about 4 cm in length along the longest length of the balloon, at most about 4.25 cm in length along the longest length of the balloon, at most about 4.5 cm in length along the longest length of the balloon, at most about 4.75 cm in length along the longest length of the balloon, at most about 5 cm in length along the longest length of the balloon, at most about 5.25 cm in length along the longest length of the balloon, at most about 5.5 cm in length along the longest length of the balloon, at most about 5.75 cm in length along the longest length of the balloon, at most about 6 cm in length along the longest length of the balloon, 6.25 cm in length along the longest length of the balloon, at most about 6.5 cm in length along the longest length of the balloon, at most about 6.75 cm in length along the longest length of the balloon, at most about 7 cm in length along the longest length of the balloon, at most about 7.25 cm in length along the longest length of the balloon, at most about 7.5 cm in length along the longest length of the balloon, at most about 7.75 cm in length along the longest length of the balloon, and at most about 8 cm in length along the longest length of the balloon. As used herein with respect to balloon dimensions whether length or diameter, the term "about" means variations of at least one of 0.1 cm, 0.2 cm, 0.25 cm, 0.5 cm, and 1 cm.

In some embodiments, the implant comprises attachment tabs or attachment elements over the anterior and/or posterior and/or medial side, and/or lateral side (and/or some combination thereof) of a condyle. In some embodiments, the implant comprises attachment tabs or attachment elements in the intercondylar notch. In some embodiments, the implant comprises attachment tabs or attachment elements superiorly at the distal end of the femur anteriorly.

The posterior of the knee can be difficult to access without disturbing joint components (or in order to minimize such disturbance) such as tendons, ligaments, etc. Thus, in some embodiments, the implant comprises strings, reigns, lassos, and/or lanyards that may pass from the posterior of the implant via the intercondylar notch anteriorly to join with themselves and/or other coupling devices. In some embodiments, posterior reigns or suture-like lanyards cinch up the implant from inside the posterior intercondylar notch toward another connection site around the femur. These couplers may be pre-coupled to the implant, and the implant and its couplers may be configured to be pulled (or cinched) from the anterior of the implant once the implant is in its general location relative to the condyle in order to finally position the implant about the condyle—in particular in order to cinch the implant about the posterior of the condyle. Likewise, in some embodiments where the implant is pre-molded, the coupler as described are adapted to move the implant to its final position with conformity to the condyle's posterior with minimal disturbance to the joint structures at the joint's posterior (minimal cutting, minimal moving, and or minimal detachment, for non-limiting example). In some embodiments at least a portion of the ligamentary structure of the knee is spared.

FIG. 10A depicts a side view of an embodiment of the knee implant 20 curved about at least one condyle 22 of a femur 24, the implant 20 having appendages 4b, 4d extending from an inflated balloon 6 and showing the inflation medium 46 moved anteriorly toward the patella 40 when the knee joint is slightly flexed. Likewise, FIG. 10B depicts a side view of an embodiment of the knee implant 20 curved about at least one condyle 22 of a femur 24, the implant 20 having appendages 4b, 4d extending from an inflated balloon 6 and having couplers 44a, 44b (which may be, for non-limiting example, staples or screws) coupling the appendages 4b, 4d to the femur 24 and showing the inflation medium 46 moved anteriorly toward the patella 40 when the knee joint is slightly flexed.

FIGS. 11A, 11B, and/or 110 may be used to describe a unicompartment implant 2 (or unicompartment knee implant, terms which may be used interchangeably) described herein, having appendages 4a, 4c, extending from a balloon 6 (not shown in FIG. 11A) and including holes 8a-8h, and/or tabs 10a-10f which may be used with couplers (not shown) to couple the implant to a bone of the knee joint (which may be the femur, the tibia, or the patella). Features shown in FIGS. 11A, 11B, and/or 110 are common to both the unicompartment knee implant and the patch implant (discussed elsewhere herein), although dimensions may differ as described herein. Thus, FIGS. 11A, 11B, and/or 11C may be used to describe the unicompartment knee implant and/or the patch implant. FIG. 11A depicts an embodiment of the unicompartment knee implant 2 curved to simulate curvature about one condyle of a femur, the implant 2 having appendages 4a, 4c, extending from an uninflated balloon (not shown) and including tabs 10a-10f and/or holes 8a-8h, which may be used with couplers (not shown, described elsewhere herein) to couple the implant 2 to the femur of the knee joint. FIG. 11B depicts an embodiment of the unicompartment knee implant 2 curved to simulate curvature about one condyle of a femur, the implant having appendages 4a, 4c, extending from an inflated balloon 6 and including tabs 10a-10f and/or holes 8a-8h, which may be used with couplers (not shown, described elsewhere herein) to couple the implant 2 to the femur of the knee joint. FIG. 11C depicts a bottom-up view of an embodiment of the unicompartment knee implant 2 curved to simulate curvature about one condyle of a femur, the implant 2 having appendages 4a, 4c, extending from an inflated balloon 6 and including tabs 10a-10f and/or holes 8a-8h, which may be used with couplers (not shown, described elsewhere herein) to couple the implant 2 to the femur of the knee joint.

In some embodiments, the unicompartment implant including attachment tabs is at least one of: at most about 15 cm in length along the longest length of the implant, at most about 15.25 cm in length along the longest length of the implant, at most about 15.5 cm in length along the longest length of the implant, at most about 15.75 cm in length along the longest length of the implant, at most about 16 cm in length along the longest length of the implant, at most about 16.25 cm in length along the longest length of the implant, at most about 16.5 cm in length along the longest length of the implant, at most about 16.75 cm in length along the longest length of the implant, at most about 17 cm in length along the longest length of the implant, at most about 17.25 cm in length along the longest length of the implant, at most about 17.5 cm in length along the longest length of the implant, at most about 17.75 cm in length along the longest length of the implant, at most about 18 cm in length along the longest length of the implant, 18.25 cm in length along the longest length of the implant, at most about 18.5 cm in length along the longest length of the implant, at most about 18.75 cm in length along the longest length of the implant, at most about 19 cm in length along the longest length of the implant, at most about 19.25 cm in length along the longest length of the implant, at most about 19.5 cm in length along the longest length of the implant, at most about 19.75 cm in length along the longest length of the implant, at most about 20 cm in length along the longest length of the implant, at most about 20.25 cm in length along the longest length of the implant, at most about 20.5 cm in length along the longest length of the implant, at most about 20.75 cm in length along the longest length of the implant, at most about 21 cm in length along the longest length of the implant, at most about 21.25 cm in length along the longest length of the implant, at most about 21.5 cm in length along the longest length of the implant, at most about 21.75 cm in length along the longest length of the implant, at most about 22 cm in length along the longest length of the implant, at most about 22.25 cm in length along the longest length of the implant, at most about 22.5 cm in length along the longest length of the implant, at most about 22.75 cm in length along the longest length of the implant, at most about 23 cm in length along the longest length of the implant, 23.25 cm in length along the longest length of the implant, at most about 23.5 cm in length along the longest length of the implant, at most about 23.75 cm in length along the longest length of the implant, at most about 24 cm in length along the longest length of the implant, at most about 24.25 cm in length along the longest length of the implant, at most about 24.5 cm in length along the longest length of the implant, at most about 24.75 cm in length along the longest length of the implant, at most about 25 cm in length along the longest length of the implant, at most about 25.25 cm in length along the longest length of the implant, at most about 25.5 cm in length along the longest length of the implant, at most about 25.75 cm in length along the longest length of the implant, and at most about 26 cm in length along the longest length of the implant. As used herein with respect to implant length dimensions, the term "about" means variations of at least one of 0.1 cm, 0.2 cm, 0.25 cm, 0.5 cm, and 1 cm.

In some embodiments, the unicompartment implant is longer than it is wide, and the longer portion of the implant wraps from the anterior of the condyle to the posterior of the condyle. In some embodiments, the length of the implant is longer on the outer edge of the implant than on the inner edge nearest the trochlear groove (whether used on the lateral or medial condyle).

FIGS. 12A, 12B, and/or 12C may be used to describe a unicompartment knee implant (unicompartment implant) described herein, having appendages 4a, 4c, extending from a balloon 6 and including holes 8a, 8b, 8c, and/or tabs 10a, 10b, 10c, 10d, 10e, 10f which may be used with couplers (not shown) to couple the implant to a bone of the knee joint (which may be the femur, the tibia, or the patella). Features shown in FIGS. 12A, 12B, and/or 12C are common to both the unicompartment knee implant and the patch implant (discussed elsewhere herein), although dimensions may differ as described herein. Thus, FIGS. 12A, 12B, and/or 12C may be used to describe the unicompartment knee implant and/or the patch implant. FIG. 12A depicts a bottom-up view of an embodiment of the implant 2 (unicompartment or patch), the implant having appendages 4a, 4c, extending from a balloon 6 and including holes 8a, 8b, 8c, which may be used with couplers (not shown) to couple the implant 2 to the femur of the knee joint. FIG. 12B depicts a bottom-up view of an embodiment of the implant 2 (unicompartment or patch), the implant having appendages 4a, 4c, extending from a balloon 6 and including tabs 10a, 10b and hole 8a which may be used with couplers (not shown) to couple the implant to the femur of the knee joint. FIG. 12C depicts a bottom-up view of an embodiment of the implant 2 (unicompartment or patch), the implant having appendages 4a, 4c, extending from a balloon 6 and including tabs 10c, 10d, 10e, and 10f and hole 8a which may be used with couplers (not shown) to couple the implant to the femur of the knee joint.

In all descriptions provided herein of the unicompartment implant, the implant may instead be configured to couple to the tibia or to the fibula or the patella. It is the intention and understanding that the implant is suited for this purpose in certain embodiments with adjustments to account for dimensional differences of the particular bones. Most descriptions provided herein are directed to embodiments coupling the implant to the femur, however, this is primarily for ease of description and continuity, and does not preclude embodiments wherein the implant is coupled to the tibia (or other bones). Likewise, as noted elsewhere herein, there are embodiments where the implant may be coupled to two bones (at least), for example to both a tibia and a femur.

Meniscal Replacement or Repair, and Solid, Rigid, or Semi-Rigid Components:

Provided herein is an implant having a balloon having a first and second chamber. The implant may be any of the Dual Compartment, Unicompartment, and Patch implants described herein. The second chamber may be configured to replace and/or partially replace fibrocartilage meniscal loss. The implant may have two lobes of chambers which may be alternatively described as two superimposed balloon radii in apposition to each other. The implant may be configured to provide stability between the femur and tibia by providing a meniscus wedge. In some embodiments the implant comprises a portion configured to replace and/or partially replace fibrocartilage meniscal loss. Such an embodiment may not require a second chamber.

In some embodiments a chamber of the implant is configured to receive a solid piece configured to restore joint and/or bone alignment. In some embodiments, the chamber is configured to receive a plurality of solid pieces, each of which can be used to increase the space between a first bone and a second bone in order to restore and/or improve joint and/or bone alignment. The solid pieces may be wedge-shaped, or be provided in various sizes and/or shapes. The solid pieces may individually or together be used in a chamber or multiple chambers of the implant. The solid piece (or pieces) may be used to ratchet adjacent bones to a desired distraction and/or alignment to restore and/or improve joint and/or bone alignment. The solid piece may be put in a chamber of the implant, which may enclose or partially enclose the piece to hold the piece in place. In some embodiments, a block of biocompatible material (such as PMMA or another bone-like substitute) may be provided and may be formed (by carving or other forming method) by the surgeon to a desired shape. The formed piece may then be put in a chamber of the implant, which may enclose or partially enclose the piece to hold the piece in place.

In some embodiments, the inflation medium is a methyl methacrylate or other biocompatible hardening substance which can flow when initially put into the chamber, and hardens to become a rigid piece (or solid piece). The methyl methacrylate or other biocompatible hardening substance may conform to the shape of the chamber, or may conform to the shape of a space between bones and/or other joint structures. The methyl methacrylate or other biocompatible hardening substance may conform to a form chosen by the surgeon using tools and/or pressure to influence the final shape of the rigid piece formed by the methyl methacrylate or other biocompatible hardening substance upon hardening.

In a separate embodiment, methylmethacrylate can be used on the bone engaging surface of the implant to secure the implant to the bone and/or cartilage. In another embodiment, the methylmethacrylate may be used to fill in space in the joint either between the bone or cartilage and the implant or between the implant and the joint.

The solid piece (whether formed in situ or by a surgeon or pre-formed) may be cushioned by the implant. The implant may comprise an inflatable chamber between the solid piece and the femur. The implant may comprise an inflatable chamber between the solid piece and the tibia. The implant may comprise an inflatable chamber between the solid piece and the patella. The implant may comprise an inflatable chamber between the solid piece and the second bone. The implant may comprise a pad between the solid piece and the femur as a cushion. The implant may comprise a pad between the solid piece and the tibia as a cushion. The implant may comprise a pad between the solid piece and the patella as a cushion.

The solid piece may provide at least one of about 1 degree of joint correction, about 2 degrees of joint correction, about 3 degrees of joint correction, about 4 degrees of joint correction, about 5 degrees of joint correction, about 6 degrees of joint correction, about 7 degrees of joint correction, about 8 degrees of joint correction, about 9 degrees of joint correction, and about 10 degrees of joint correction. With respect to degrees of joint correction, the term "about" can mean ranges of 1%, 5%, 10%, 25%, or 50%.

The implant can be used in a variety of joints where the implant replaces a bone on bone surface and cushions the interaction between the articular ends of any two bones, such as at the femoral tibial and patella femoral knee interfaces. Where the implant is substituting or enhancing articular cartilage, the rigidity can be reduced or enhanced to maximize conformation changes that arise during motion as enabled by the two opposing walls and intended inner space, coupled with considerations in any joint surgical reconstruction with accommodation to or amplification of the existing joint ligaments, tendons or dearth thereof. The implant 10 may be deflated and removed by minimally invasive surgery, for example, after the implant has served its purpose of regenerating tissue or if another clinical condition warrants its removal. However, it may not be clinically necessary to remove the implant even if inflation is lost, since the two remaining functions of patching the injured cartilage, and delivering restorative cells may justify implant retention.

In many embodiments the implant (or a portion thereof, such as the balloon or balloon) is a weight bearing spacer that will allow joint motions to approach normal, whether filling the space left by an entirely collapsed peripheral joint bone or the space of ablated cartilage proximate surfaces diffusely as in osteoarthritis or succinctly as in osteonecrotic defects or localized trauma. The walls may be used as a membrane for holding living cells in proximity of the osteochondral defect long enough for the cells to attach (e.g. 24 hours) or to deeply adhere (up to 28 days) or return to normal (up to one year). Weight bearing will be expected to increase as distal lower extremity joints are treated.

Kits

Provided herein are kits comprising multiple implants described herein. A kit may comprise multiple sizes of a single type of implant. A kit may comprise various implant types, such as the patch, the unicompartment, and/or the dual compartment types of implants described herein. A kit may comprise various couplers, which may be selected by the surgeon depending on his comfort and expertise, and/or based on the particular patient anatomy and/or needs. The kit may further comprise any insertion tools and/or surgery tools that may uniquely assist in implanting the implant in the patient.

Implantation Methods

Implantation of implants provided herein will depend on the size of joint surface intended for reconstruction by use of the implant. In some embodiments, an arthroscope can be inserted in one side of the knee joint through a 0.5 cm wound, while the implant is inserted into the opposite joint line wound from 1-10 cm in size. The joint may be first inspected and debrided, performing an arthroscopic synovectomy, chondroplasty, and meniscectomy as needed. Additional distraction under general anesthesia with the knee at variable degrees of flex may allow for implant introduction, systematic peripheral attachment, balancing, and inflation.

In some embodiments, the implant may be selectively inflatable depending on the particular needs of the patient. In some embodiments, the filler of the interior of the implant may be rigid, semi-rigid, fluid, air, or combinations thereof, as described herein. In some embodiments, the implant may be used in conjunction with fibrocartilage repair or replacement. In some embodiments, the implant may be used without fibrocartilage repair or replacement. In some embodiments, the implant may be used in conjunction with boney osteotomy. In some embodiments, the implant may be used without boney osteotomy.

The posterior of the knee can be difficult to access without disturbing joint components (or in order to minimize such disturbance) such as tendons, ligaments, etc. Thus, in some embodiments, the method comprises providing an implant comprising strings, reigns, lassos, and/or lanyards that may pass from the posterior of the implant via the intercondylar notch anteriorly to join with themselves and/or other coupling devices. In some embodiments, posterior reigns or suture-like lanyards cinch up the implant from inside the posterior intercondylar notch toward another connection site around the femur. In some embodiments, the methods comprise conforming the implant posterior to the condyle by pulling the strings (or reigns, or lassos, or lanyards or the like) of the implant. Such couplers (strings, reigns, lassos, lanyards, etc) may comprise suture materials and/or wire materials.

These couplers (i.e. strings, reigns, lassos, lanyards, etc) may be pre-coupled to the implant, and the implant and its couplers may be configured to be pulled (or cinched) from the anterior of the implant once the implant is in its general location relative to the condyle in order to finally position the implant about the condyle—in particular in order to cinch the implant about the posterior of the condyle. Likewise, in some embodiments where the implant is pre-molded, the coupler as described are adapted to move the implant to its final position with conformity to the condyle's posterior with minimal disturbance to the joint structures at the joint's posterior (minimal cutting, minimal moving, and or minimal detachment, for non-limiting example). In some embodiments at least a portion of the ligamentary structure of the knee is spared.

The implant is inserted arthroscopically through a cannula about 10 mm in diameter with the implant in the deflated construct, and once inside the prepared joint space and secured therein by the skirt or tabs, the implant will be distended or inflated with gas, gel, fluid or fluid that becomes a resilient solid to fill the original natural space of about 0.5 cm between the bones of the joint (between at least two bones of the joint). If the implant is not inserted through a cannula, it may be inserted through an open incision from one to forty centimeters in length at the surgeons discretion. Tensioning will be by the surgeon's sense of proper pressure application aided by a gauged syringe for insertion of viscolubricants such as Synvisc, Hyalgan, Supartz and/or analgesics such as lidocaine gel. The insertion of liquids to the joint per se may be directly, through a cannula to the joint space previously in place for debridement, and or via a cannula or tube that is not part of the original implant assembly. Once the joint is cleaned, the implant is inserted and appropriately fixed to avoid extrusion or dislocation thereof. This may be via attachment of the implant tabs and/or by a combination of tab use plus intended friction created by implant surface coverings (analogous to Velcro) or a draw string at the smaller base of the implant.

In some embodiments the attachment tabs are positioned on the implant to both secure the implant to the joint components, and to enable a physician to ensure the implant has a minimum amount of slack that could create wrinkles or loose areas to avoid unnecessary friction and/or wear of the implant of the patient's anatomy. Figures depicted herein show examples of properly situated attachment tabs configured for these dual purposes. In some embodiments, fewer tabs are needed to achieve these goals.

In some embodiments, where slack or voids exist, the balloon under compression may fill such areas. The implant in some embodiments is configured to allow hyaline and/or cartilage cells to fill any irregularities or craters in the joint components and grow to refurbish natural joint contour. When the implant implantation is combined with, for example, movement of the treated joint in a constant passive motion machine for 12 hrs a day for 6 weeks after surgery implanting the implant, cell growth will create renewed hyaline cartilage, and/or blood/fibrin and scar to create fibrocartilage filler material.

Each attachment tab insert site may be clinically determined centripitally around the implant during surgery, driving slots or holes sequentially with an osteotome or drill immediately followed by insertion of the triangled tab extension into the bone slots or screw respectively. For example, if the implant were viewed like a clockface the first tab could be tacked/tapped in a 2 o'clock, then 7, 10, 4 11, 5, 12, 6 (wherein #2, 7, 10, 4 are over the bilateral femurs superior/inferior to collateral ligaments, 11, 12 are superior at the distal anterior femur beneath the upper patella, and 5, 6 are inside the intercondylar notch anterior to cruciates.) This can be like putting a saddle on a horse, going around the knee end with a grasper, to tug the polymer toward fit, tapping a slot over the side of the femur with a thin one-half inch osteotome, angling cuts distally, one by one, as if to pull the implant (or saddle) into its angle of repose, seating ideally over the condyles and ridings nicely in the trochlear groove.

In some embodiments, the metal clips could be set angled at about 120 degrees, as greater than 90 will favorably distract/hold the implant to tighter fit analogous to a mylar compliant balloon or stretch sock fitting over a protuberance as opposed to a piece of (non-compliant) paper that results is wrinkles and areas of incongruence between the implant and bone end. Reducing dislodgement tendency and snugging the polymer once stretched to best fit may avoid the failure history as illustrated in the Danish Polymer hip cap solid crescent shaped hip resurfacing implants which lacked inflation, surface stability, accommodation, and fixation.

Inflation may also be specified by clinical need, and modifications in the implant multi-cell (multi-compartment) construction allows for selective inflation with substances ranging from gas to solid, including gels or semi-solids that can as part of material layered integrity either provide calculated hardness (durometer) to overcome and resist limb adjacent bone mal-alignment, and/or to deliver new regenerative tissues for restoration of natural anatomy of time. That is, certain sections of the implant may be electively inflated of left without expansion, to adjust to fit as matching a normal or uninjured contralateral limb for the involved patient.

Indeed, patient interaction and feedback may be sought so as to bring to orthopedic conceived art and science the individual's own needs and concerns. It is said that for patients who have anterior cruciate injuries, one third require reconstruction for knee joint stabilizer, one third do not—living with a reduced activity level, and one third deliberate extensively until a choice between the two continuum options is made.

A goal of embodiments of implants described herein is to maintain remnant living tissue by using minimally invasive technologies, smaller incisions when they serve the patient equally to larger, sacrificing the least normal tissue as possible. Implants described herein assist and improve on current treatment options available by avoiding as much as possible the ablative bone and cartilage resecting, ligament removing total knee arthroplasty and instead to restore the padding lost in injury or disease or surgery.

Examples from within the techniques include electing to repair rather than reconstruct anterior cruciate ligaments in certain situations, proved warranted and effective at a $p<0.3$ statistical level. Whereas Carticel chondrocyte implantation is useful to enable articular surface regrowth with hyaline, rather than scar/fibrocartilage from picking/drilling, the massive morbidity from periosteal harvesting is unnecessary. This is because it takes only 24 hours for the cartilage cloned chondrocytes to attach to the prepared joint surface, and the polymer membrane (patch implant described herein, for example, or use of chondrocytes on surfaces of the dual compartment implant or the unicompartment implant) over the prepared defect (like a manhole cover) will adeptly substitute for periosteum.

With these concepts in mind in is the overall intent to do what is necessary to restore function and nothing more in order to spare the patient removal of injured tissues that may recover or regrow, by implementing a common sense approach to limb repair and reconstruction with the implant and methods of use thereof. In animals as horses and dogs, where recovery instructions are even less likely to be followed than with humans, implanting secure restorative implants for joint surface refurbishment may offer renewed function and save lives that would have otherwise been sacrificed.

Rehabilitation of knee implant treated patients will engage prudent early motion. The amount of weight bearing allowed with be analogous to the procedures written by this primary surgery for Carticel implanted cases, following the principles that excessive amounts and repetitions of stress upon reconstructed areas should be avoided for 6-12 weeks after surgery. However, the knee implant surgeries per se are expected to take less than one hour, involve less than 1 cc blood loss, require wounds less than or equal to 10 cm overall (depending on the embodiment of the implant), and the end result intends to permit early full weight bearing. Zealous sports activities may be restricted until the bone ingrowth and cartilage renewal is reasonably expected, between 2 and 12 months after surgery depending upon the amount of joint tissue replaced.

In some situations, the removal of the implant may be needed, and embodiments of the implants described herein are configured for removal arthroscopically, and with the allowance to perform all regular older routine accepted techniques ranging from joint debridement to drilling, partial or total replacement. In some embodiments the implant is configured for removal and replacement with a replacement implant—either immediately (within a week), or after a period of longer time (for example, after about 6 weeks to 1 year in the case of infection once all foreign bodies are removed and depending upon the surgeon's and/or infectious disease consultant's opinion.

Specific surgical decisions related to size matching, fixation and or concomitant osteotomy warranted reconstruction are left to the primary surgeon and patient in each case.

The implant is inserted by minimally invasive surgery, in some embodiments, however, in other embodiments, the implant may not be inserted by minimally invasive surgery. In some embodiments, the implant is delivered through an incision that is about 0.5 inches long. In some embodiments, the implant is delivered through an incision that is about 1 centimeter long. In some embodiments, the implant is delivered through an incision that is at most about 1 inch long. In some embodiments, the implant is delivered non-arthroscopically through an incision that is at least 1 centimeter long. In some embodiments, the implant is delivered through an incision that is at most about 0.75 inches long. In some embodiments, the implant is delivered through an incision that is at most about 0.5 inches long. In some embodiments, the implant is delivered through an incision that is about 8 centimeters long. In some embodiments, the implant is delivered through an incision that is about 9 centimeters long. In some embodiments, the implant is delivered through an incision that is about 10 centimeters long. In some embodiments, the implant is delivered through an incision that is about 11 centimeters long. In some embodiments, the implant is delivered through an incision that is about 12 centimeters long. In some embodiments, the implant is delivered through an incision that is over about 10 centimeters long. In some embodiments, the implant is delivered through an incision that is at up to about 40 centimeters long. In some embodiments, the implant is delivered through multiple incisions. With respect to incision length, the term "about" can mean ranges of 1%, 5%, 10%, 25%, or 50%.

In some embodiments the implant is configured to be delivered to the joint arthroscopically. In some embodiments, the implant is configured to fit within a cannula having a distal end inner diameter of at most 10 millimeters. In some embodiments, the implant is configured to fit within a cannula having a distal end inner diameter of at most 9 millimeters. In some embodiments, the implant is configured to fit within a cannula having a distal end inner diameter of at most 5 millimeters.

In some embodiments, the implant is configured to fold in order to fit within a cannula having a distal end inner diameter of at most 10 millimeters. In some embodiments, the implant is configured to fold in order to fit within a cannula having a distal end inner diameter of at most 9 millimeters. In some embodiments, the implant is configured to fold in order to fit within a cannula having a distal end inner diameter of at most 5 millimeters.

In some embodiments, the implant is configured to be delivered to a joint through a cannula having a distal end inner diameter of at most 10 millimeters. In some embodiments, the implant is configured to be delivered to a joint through a cannula having a distal end inner diameter of at most 9 millimeters. In some embodiments, the implant is configured to be delivered to a joint through a cannula having a distal end inner diameter of at most 5 millimeters.

In some embodiments the implant is configured to be delivered to the joint arthroscopically. In some embodiments, the implant is configured to fit within a cannula having a distal end inner diameter of at most about 10 millimeters. In some embodiments, the implant is configured to fit within a cannula having a distal end inner diameter of at most about 9 millimeters. In some embodiments, the implant is configured to fit within a cannula having a distal end inner diameter of at most about 5 millimeters. With respect to cannula distal end inner diameter, the term "about" can mean ranges of 1%, 5%, 10%, 25%, or 50%.

In some embodiments, the implant is configured to fold in order to fit within a cannula having a distal end inner diameter of at most about 10 millimeters. In some embodiments, the implant is configured to fold in order to fit within a cannula having a distal end inner diameter of at most about 9 millimeters. In some embodiments, the implant is configured to fold in order to fit within a cannula having a distal end inner diameter of at most about 5 millimeters. With respect to cannula distal end inner diameter, the term "about" can mean ranges of 1%, 5%, 10%, 25%, or 50%.

In some embodiments, the implant is configured to be delivered to a joint through a cannula having a distal end inner diameter of at most about 10 millimeters. In some embodiments, the implant is configured to be delivered to a joint through a cannula having a distal end inner diameter of at most about 9 millimeters. In some embodiments, the implant is configured to be delivered to a joint through a cannula having a distal end inner diameter of at most about 5 millimeters. With respect to cannula distal end inner diameter, the term "about" can mean ranges of 1%, 5%, 10%, 25%, or 50%.

In some embodiments the implant may be provided as a deflated balloon for insertion into the joint space. In some embodiments the implant may be provided as folded balloon that may be collapsed like an umbrella for insertion into the joint space. In some embodiments the implant may be provided as collapsed balloon that is of an irregular folded pattern to minimize its folded (or collapsed) size for insertion into the joint space. In some embodiments, the implant is configured to blow up (or expand) to take the form of the expanded, distracted, debrided joint.

In some embodiments, the implant replaces periosteum.

In some embodiments, the implant is implanted to preserve bone as compared to a typical arthroplasty procedure of the joint. In some embodiments, the implant is implanted to preserve cartilage as compared to a typical arthroplasty procedure of the joint. In some embodiments, the implant is implanted with minimal soft tissue dissection as compared to a typical arthroplasty procedure of the joint. In some embodiments, the implant is implanted without joint dislocation. In some embodiments, once implanted, the joint is adaptable to revision surgery. In some embodiments once implanted, the joint retains at least one of: about 90% of normal joint function, about 95% of normal joint function, about 85% of normal joint function, about 80% of normal joint function, about 75% of normal joint function, about 70% of normal joint function, about 65% of normal joint function, about 60% of normal joint function, about 55% of normal joint function, about 50% of normal joint function, at least 95% of normal joint function, at least 90% of normal joint function, at least 85% of normal joint function, at least 80% of normal joint function, at least 75% of normal joint function, at least 70% of normal joint function, at least 65% of normal joint function, at least 60% of normal joint function, at least 55% of normal joint functions at least 50% of normal joint function, about 50%-about 75% of normal joint function, about 50%-about 70% of normal joint function, about 60-about 70% of normal joint function, about 70%-about 80% of normal joint function, about 70%-about 90% of normal joint function, about 80%-about 95% of normal joint function, about 80%-about 90% of normal joint function, and about 90%-about 95% of normal joint function. As used herein with respect to percentage of normal joint function, the term "about" can be ranges of 1%, 5%, 10%, or 25%. For example, a range of 1% with respect to about 90% of normal joint function covers 89% to 90% of normal joint function.

In some embodiments, prior to deploying the implant embodying features of the invention, the cartilage lining the joint is prepared by removing hyaline or fibro cartilage flaps or tears, and areas of chondral advanced fissuring are excised or debrided to create precisely defined defects surrounded by stable normal remnant hyaline cartilage with vertical edges in relation to the damaged surface. It is these defects of the cartilage previously normal surface into which new living cells may be injected or otherwise inserted, and allowed to aggregate by the implant interpositional arthroplasty proximate expanded compressive external wall material. Synovitis invading the joint periphery may be vaporized and extracted conventionally or by the use of steam. Areas of greater cartilage damage are removed for subsequent regeneration and the less afflicted areas having stable cracks are treated to seal or weld the cracks. Areas where the tugor or consistency or minimally damaged cartilage can be preserved are intentionally saved rather than destroyed so as to support the normal spacing and gliding opportunity of the more normal joint interface. Thus, normal cartilage is left behind and abnormal cartilage is removed with the implant making up for the deficiencies. With the present invention, it is preferred in some embodiments to avoid joint dislocation so as to preserve natural innervations and vascularity and thus preserving the blood supply.

Joint preparation is usually performed under a brief general anesthetic of outpatient surgery. Increasing the joint space may be necessary and allows the surgeon to wash out noxious enzymes, to remove invasive synovitis, to remove loose bodies, to prepare osteochondral defects ideally and otherwise prepare the joint for the implant. Partial or complete inflation of the implant may precede release of traction in some embodiments. In some embodiments, regeneration agents or cells are inserted with the implant or as a fluid or 3-D template prior to release of traction and wound closure. It is preferred, in some embodiments, to perform joint debridement, implant deployment and application of cell regeneration agent, e.g. stem cell application, under the same anesthetic. As described by several companies in the Stem Cell Summit held in New York, N.Y. on Feb. 17, 2009, it is desirable to obtain an aspiration of the patient's bone marrow from the iliac crest after anesthesial sterilely at the beginning of the operation. The intraoperative technologist will "dial in the cells" to regenerate areas of maximum pathophysiology while the surgeon debrides or otherwise prepares the joint and inserts the implant, placing the cells at the best time. Cell implantation may also occur as a secondary or tertiary reconstructive treatment adjunct.

Provided herein is a method for restoring a joint comprising: providing an implant configured for deployment between a femur and at least one second bone of a joint, the implant comprising a balloon comprising a first portion that is configured to engage the femur of the joint, a second portion that is configured to engage at least one second bone of the joint, a side portion connecting the first portion and the second portion, in which the side portion facilitates relative motion between the first portion and the second portion, and an interior that is optionally inflatable with a first inflation medium; and coupling a first appendage of the balloon to the femur of the joint. Provided herein is a method for restoring a joint comprising: providing an implant configured for deployment between a tibia and at least one second bone of a joint, the implant comprising a balloon comprising a first portion that is configured to engage the tibia of the joint, a second portion that is configured to engage at least one second bone of the joint, a side portion connecting the first portion and the second portion, in which the side portion facilitates relative motion between the first portion and the second portion, and an interior that is optionally inflatable with a first inflation medium; and coupling a first appendage of the balloon to the tibia of the joint.

In some embodiments, at least two of first portion, the second portion, and the side portion are contiguous. In some embodiments, the first portion comprises a first wall, the second portion comprises a second wall, and the side portion comprises a side wall.

In some embodiments the method comprises providing an ingrowth patch on at least one of the first portion configured to engage the femur, the second portion configured to engage the second bone, the side portion, and the appendage. In some embodiments the method comprises providing an ingrowth patch on at least one of the first portion configured to engage the tibia, the second portion configured to engage the second bone, the side portion, and the appendage. The ingrowth patch may be configured to encourage and/or promote tissue ingrowth, such as bone ingrowth, for non-limiting example. The patch may be as large as the portion itself (whether the first portion the second portion, the side portion, or the appendage) or may be smaller than the portion (such as in the shape of a strip or other shaped patch). The ingrowth patch may comprise a surface irregularity or roughness. The ingrowth patch may be Velcro-like. In some embodiments the implant comprises an ingrowth patch on the first portion and/or the second portion, from (and in some embodiments including) a first appendage to a second appendage. In some embodiments, wherein the appendages loosen from attachment from the bone (by design and/or from wear and/or over time), the ingrowth patch aids in securing the implant to the bone. In some embodiments, the ingrowth patch comprises beads and/or bead-like elements attached to the implant. Such an ingrowth patch may be configured to simulate trabecular bone space of a normally cancellous latticework. In some embodiments, the beads are sintered beads of various sizes. In some embodiments, the beads are sintered beads about 400 microns in size. With respect to bead size, the term "about" can mean ranges of 1%, 5%, 10%, 25%, or 50%. In some embodiments, the first bone and/or the second bone is roughened to acquire a bleeding bone to facilitate ingrowth. In some embodiments, about 0.5 mm of cortical tissue is removed to facilitate ingrowth.

In some embodiments, the method comprises coupling a second appendage of the balloon to the femur of the joint. In some embodiments, the method comprises coupling a second appendage of the balloon to the tibia of the joint. In some embodiments, the method comprises coupling a second appendage of the balloon to at least one second bone of the joint. In some embodiments, the method comprises coupling a second appendage of at least one of the first portion, the second portion, and the side portion to at least one of the femur and at least one second bone of the joint. In some embodiments, the method comprises coupling a second appendage of at least one of the first portion, the second portion, and the side portion to at least one of the tibia and at least one second bone of the joint. In some embodiments, coupling at least one of the first appendage and the second appendage provides ligamentary-like support to the femur and the at least one second bone of the joint. In some embodiments, coupling at least one of the first appendage and the second appendage provides ligamentary-like support to the tibia and the at least one second bone of the joint. In some embodiments, coupling at least one of the first appendage and the second appendage provides ligamentary-like support to the joint. In some embodiments, the first appendage and the second appendage are configured to provide tendon-like support to the femur and the at least one second bone of the joint. In some embodiments, the first appendage and the second appendage are configured to provide tendon-like support to the tibia and the at least one second bone of the joint. In some embodiments, the first appendage and the second appendage are configured to provide tendon-like support to the joint.

In some embodiments, the method comprises providing an inflation port in communication with the interior of the balloon for inflation of the interior of the balloon with the first inflation medium. In some embodiments, the method comprises using an inflation port of the implant that is in communication with the interior of the balloon to inflate the interior of the balloon with the first inflation medium. In some embodiments, the method comprises puncturing the balloon to inflate the interior of the balloon with the first inflation medium. In some embodiments, the method comprises providing a balloon having self-sealing capability. In some embodiments, the method comprises providing a balloon having self-sealing capability upon inflation of the interior of the balloon with the first inflation medium. In some embodiments, the method comprises providing a balloon comprising a seal capable of closing the interior of the balloon.

In some embodiments, the method comprises providing a balloon having an interior comprising a plurality of inflatable chambers. In some embodiments, the interior comprises a plurality of individually inflatable chambers. In some embodiments, the method comprises inflating a first chamber of the plurality of inflatable chambers with a first inflation medium. In some embodiments, the first chamber and the inflation medium is selected based on the particular needs of the patient. For non-limiting example, if the patient has bone loss due to an injury, the chamber may be selected at the location of the missing bone, and may be filled with a rigid inflation medium (or one that becomes rigid once in the chamber) in order to replace the missing and/or damaged bone. Alternatively, or in addition, a chamber may be chosen to restore alignment of the joint, and inflated with an appropriate inflation medium to impart both alignment and cushion to the joint. In some embodiments, the method comprises inflating a second chamber of the plurality of individually inflatable chambers with a second inflation medium.

In some embodiments, the balloon is a composite structure. In some embodiments, the balloon comprises layers of porous and/or non-porous materials, or otherwise contain treatment or cell regeneration agents. In some embodiments, a first layer of the balloon is a thin, but strong layer of a thermoplastic, such as a thermoplastic polyurethane, for non-limiting example, which has microporosity sufficient to allow passage or egress of treatment or cell regeneration agents from a second layer. The second layer may be a central layer (which lies between the first layer and a third layer or a fourth layer or more layers). The first layer may comprise a bone engaging surface in some embodiments. The degree of microporosity to enable egress of treatment or cell regeneration agents from the second layer is found in polymer layers such as Chronoflex or Bionate 55. The bone engaging surface of the implant may be coated and/or impregnated with a latticework of polymer that is surface sprayed or layered on the bone engaging surface of the implant to promote cartilage tissue regeneration. This bone engaging surface coating may contain living chondrocytes (for example, as is provided in the Carticel procedure by the Genzyme company), and/or may contain stem cells with directed gene mutations to enhance adherence of the coating to the implant. The bone engaging surface may comprise peaks and troughs. The living cells may be provided in troughs while the surface peaks may be used for at least one of: space validation, traction, and cell protection. Either surface may be coated with other coatings such as as anti-infectives, lysophosphatidic acid, hyaluronic acid, hydrogels, or biophosphates.

In some embodiments, the first inflation medium imparts rigidity in the implant. In some embodiments, the first inflation medium imparts cushion in the implant. In some embodiments, the inflation medium chosen for the first inflation medium, and/or the particular choice of chamber (in embodiments having multiple chambers) filled with such first inflation medium aligns the joint. In some embodiments, the inflation medium chosen for the first inflation medium, and/or the particular choice of chamber (in embodiments having multiple chambers) filled with such first inflation medium aligns the bones of the joint. In some embodiments, the inflation medium chosen for the first inflation medium, and/or the particular choice of chamber (in embodiments having multiple chambers) filled with such first inflation medium changes the bone alignment. In some embodiments, the inflation medium chosen for the first inflation medium, and/or the particular choice of chamber (in embodiments having multiple chambers) filled with such first inflation medium improves joint alignment. In some embodiments, the inflation medium chosen for the first inflation medium, and/or the particular choice of chamber (in embodiments having multiple chambers) filled with such first inflation medium restores, at least in part, joint alignment. In some embodiments, individual chambers of the interior are selectively inflated with a first inflation medium and/or a second inflation medium. In some embodiments, individual chambers of the interior are selectively inflated with a first inflation medium and/or a second inflation medium in order to reconstruct the joint and/or in order to reconstruct bones of the joint.

Over time, ingrowth of repair tissue aids in fixation and stability externally to the implant, while the soft cushioning implant interior will absorb forces across the joint surfaces and permit proper motion. The turgor or wall tension of the implant as well as the inside distension of the implant per se can be adjusted by adding or removing the inflation substance to the implant's interior space.

Accordingly, the present invention provides a new approach to arthroplasty that involves a resilient implant deployed between bones of the knee joint. Whereas a joint is comprised of the interface between bone cartilage space cartilage bone, in certain joint spaces such as the knee, the invention cushion may expand to fit the spaces between both "knee joints"—the femoral tibial involved on standing or walking on a level plane, and the patella femoral bones of the knee more involved on stair ascent and decent. For example, pressures behind the knee cap or patella when lying are zero, when standing are 0.7 times body weight, and when going up and down the patella femoral pressures are 3-4 times body weight. Thus, the implants will need to accommodate all the normal body functional pressures and complex space movements. The implant embodying features of the present invention provides more physiologic motion and shock absorption within the joint and has combined characteristics of anatomic design symmetry, balanced rigidity with sufficient attachment connections to adjacent normal structures, and durability that meet the needs of joint reconstruction.

The opposing internal surfaces of the first and second walls of the invention may either move together in synchrony or in opposite directions from one another (e.g. the superior wall moving medially in the hip and the inferior wall moving laterally). Optionally, the implant may be fixed to a concave surface of the joint or to a convex surface of the joint, to both, or to neither (e.g., having an interference fit within the joint with an expanding balloon or cushion that fills the existing space). The implant may be inserted arthroscopically like a deflated balloon and then inflated through a cannula into the joint structure) to act as a cushion or renewed interface for painless and stable limb motion. When feasible joint capsular and adjacent ligament tissue as well as bone will be left in place to preserve the natural body, unless interfering with reconstructed limb function.

The application of steam in addition to removing damaged debris, can smooth out and reform the joint surface. The high temperature of the steam tends to weld cracks or fissures which can be present in the cartilage surface of a damaged joint. Smoothing of joint surface cartilage with steam welds or seals existing cracks or flaps in the cartilage, especially superficially as the lamina splendors, which melt together to provide a white shiny gliding joint surface. In cases where bone is exposed, the steam can be used to stabilize the periphery of the defect in the joint surface via capsulorrhaphy or joint tightening. Open mechanical and chemical debridement may also be employed to prepare the surfaces for the implant.

Once the implant is secured to the femur by means of the skirt or tabs or using other couplers, an impregnated transfer medium or cell template may be used, as described by Histogenics and Tygenix chondrocytes delivery systems wherein the position of concentrated cells is mechanically placed about the implant at areas of greatest cartilage damage to promote regrowth, or as in Carticel wherein watery cells are implanted beneath a periosteal membrane (a wall of the implant serving as the membrane), prior to completion of the inflation or expansion of the implant. At syringe or gauged device with measured screw-home pressure is used to inflate the implant.

Once the joint is ready to receive the implant, the deflated implant is advanced through the diaphragm of a delivery cannula (such as the Acufex from Smith & Nephew) or through the open incision site into the joint. It can be inflated by the attached cannula using a common syringe, inserting several cc's of filler material. Inserted contents and locations of cell placements depend on areas of need and joint size. In some embodiments of the methods several cc's of filler material and a viscolubricant in the interior of the implant will allow distension, cushioning, and gliding movements. Cell regeneration agents are placed in the areas of greatest need.

Methods of living stem cell or chondrocyte placement depend on the lesions and specific implant construct. Direct infusion into the joint with completion of implant inflation will press the cells into the hyaline surface, whereupon they attach within the first 24 hours. As a result, the patient may be forced to remain sedentary and the joint where the implant is deployed, non-weight bearing for the first day after surgery. Deeper osteochondral defects can be treated by 'hyper-perfusion of cells' via either 3-D cell transfer templates, or microneedle injection as used in treatment of diabetic patients for blood sugar testing and insulin/transdermal drug delivery. In cases of osteochondritis dissecans or localized both cartilage and bone lose, bone graft may be packed into the base of the defect followed by addition cell/tissue application. The cannula attached to the implant may be sealed and detached, or left in place for periodic aspiration of noxious enzymes as for the Cox-1, Cox-2, and 5-Lox systems, followed by reinsertion of activated substances including viscolubricants, or even more cells.

Implants embodying features of the invention may be designed for permanent or temporary deployment within a joint structure. Moreover, the implant may be formed of suitable bioabsorbable materials so that the implant may be absorbed within a particular predetermined time frame. Suitable bioabsorbable materials include polylactic acid, polyglycolic acid, polycaprolactone, copolymers, blends and variants thereof. One present method of forming the implant is to apply numerous layers of polymer such as ChronoFlex AR in a solvent and evaporating the solvent after applying each layer.

The coupling aspects (couplers) including but not limited to skirting or fixation tabs of the present implant prevent joint migration during use.

In some embodiments, the implant is adapted to restore natural joint function. In some embodiments, the implant is adapted to preserve viable joint tissue. In some embodiments, the implant is adapted to be placed with minimal surgery as compared to joint replacement therapy currently marketed. In some embodiments, the implant is adapted to permit weight bearing post surgery within at least one of: about 1 week, within about 1 day, within about 2 days, within about 3 days, within about 4 days, within about 5 days, within about 6 days, within about 10 days, within about 2 weeks, within about 3 weeks, within about 4 weeks, within about 5 weeks, within about 6 weeks. In some embodiments, the implant is adapted to permit weight bearing post surgery after about 1 day wherein full weight bearing is allowed in about 6 weeks. As used herein with respect to weight bearing timing, the term "about" can be a range of 1 day, 2 days, or 3 days, in some embodiments. In some embodiments, the implant is adapted to be allow for faster recovery and resumption of normal activities as compared to joint replacement therapy currently marketed.

In some embodiments, the balloon (or a portion thereof) is adapted to conform to the patient's anatomy. In some embodiments, the implant (or a portion thereof) is adapted to conform to the patient's anatomy. In some embodiments, the inflation medium is adapted to absorb a force (or forces) exerted on the joint. In some embodiments, the inflation medium is adapted to absorb a force (or forces) exerted on the bones of the joint. In some embodiments, the inflation medium is adapted to absorb a force (or forces) exerted on at least one bone of the joint. In some embodiments, the balloon is adapted to absorb shocks exerted on at least one of a bone, multiple bones, a ligament of the joint, ligaments of the joint, a tendon of the joint, tendons of the joint, and the joint in general. In some embodiments, the implant is adapted to restore natural cartilage cushion with stem cells.

In some embodiments, the balloon (or a portion thereof) is adapted to renew joint space. In some embodiments, the balloon (or a portion thereof) is adapted to reducing pain as compared to the pain felt prior to the implantation of the implant. In some embodiments, the balloon (or a portion thereof) is adapted to restore joint function. In some embodiments, the implant (or a portion thereof) is adapted to renew joint space. In some embodiments, the implant (or a portion thereof) is adapted to reducing pain as compared to the pain felt prior to the implantation of the implant. In some embodiments, the implant (or a portion thereof) is adapted to restore joint function.

In some embodiments, the implant is adapted to reverse arthritis in the joint.

In some embodiments, the balloon (or a portion thereof) is adapted to be placed into a debrided limb joint arthroscopically. In some embodiments, the balloon is adapted to pad cartilage defects. In some embodiments, the balloon is inflated to cushion the joint. In some embodiments the implant is adapted to deliver stem cells to at least one of the joint and a bone of the joint. In some embodiments the implant is adapted to deliver living chondrocytes to at least one of the joint and a bone of the joint. In some embodiments, the implant is adapted to provide a new articular surface for the joint. In some embodiments, the implant is adapted to act as a spacer in the joint. In some embodiments, the implant is adapted to space the bones of the joint apart for proper joint articulation. In some embodiments, the implant is adapted to space the bones of the joint apart for reduced bone-on-bone rubbing.

In some embodiments, the implant is configured to at least one of: pad cartilage, cushion the joint, deliver a pharmacologic substance, remove noxious enzymes, debride upon implantation, debride the joint following implantation, deliver a therapeutic substance, deliver a biologic substance, and deliver living stem cells. In some embodiments, the implant is configured to deliver a chemotherapeutic agent to a bone or other surrounding tissues. In some embodiments, the implant is configured to deliver an anti-infectious medication to a bone or other surrounding tissues. In some embodiments, the implant is configured to deliver at least one of an antibiotic, antifungals, and analgesics agent.

In some embodiments, the implant is configured to be selectively inflated to realign limbs.

Provided herein is a method comprising: implanting a knee implant as described herein into a subject, wherein the implant reverses arthritis in the subject.

Provided herein is a method comprising: implanting a knee implant as described herein into a knee joint of a subject and treating a component of the knee joint of the subject with at least one of an allograph tissue, an autograph tissue, and an xenograph tissue. In some embodiments, the implanting step is at least one of: prior to the treating step, simultaneous with the treating step, and following the treating step.

Provided herein is a method comprising: implanting a knee implant as described herein into a subject, wherein the implant at least one of: restores joint function and controls arthopathies. In some embodiments, the implanting spares existing anatomy.

Provided herein is a method comprising: debriding a femur condyle of a knee joint of a subject, and implanting a knee implant as described herein into the knee joint of the subject, whereby the implant is configured to anneal to the cartilage of the subject. In some embodiments, the debriding is achieved by steam application.

Provided herein is a method comprising implanting a knee implant as described herein into a joint previously treated with a joint replacement. In some embodiments, the method comprises removing the joint replacement prior to implanting the knee implant. In some embodiments, the method comprises clearing infectious matter from the joint and/or surrounding tissues. In some embodiments, the method comprises implanting a second implant of any implant described herein following removing the implant previously implanted in the joint. In some embodiments, the method comprises replacing the joint of the subject following removing the implant previously implanted in the joint. In some embodiments, the method comprises debriding the bone of the joint, and implanting an implant of any implant described herein. In some embodiments, the method comprises repeating the debriding and implanting steps.

Additional Locations for Use

Shoulder subacromical bursa may be a target joint for an implant as described herein. Rotator cuff tears may be addressed using an implant as described herein—as adjusted for the particular features, loading profile, and geometries of the joint. In shoulders, 85% of octagenians have massive rotator cuff tears and often less than half normal upper extremity abduction and flexion capabilities. There may not be sufficient remnant supraspinatus and other rotator cuff tissues to pull together. Then the humeral head rides up, in a cephalad direction, rubbing the superior bone surface on a frequently spurred and downward sloping acromion. If a subacromial implant as described herein were implanted beneath the lateral (arthroscopically decompressed and prepared) acromion, the pain of bone on bone could be reduced, and the structural anatomy between the ball and socket (humeral head and glenoid fossa) could be improved. In essence then a shoulder implant could cover the humeral head analogous to the hip redundant membrane wherein that membrane replaces a normal subacromial bursa. Optionally, a singular bladder beneath the acromion per se could pad the ball beneath it. For virtually every joint in the body (arms and legs, at least) there are similar potential implant uses.

The distal femur of the knee, and the distal humerus of the elbow are regions that interface each with two opposite joints. That is, an implant for the knee as designed with polymer capping of the femoral condyles and trochlear groove to provide cushioning of the femorotibial and patellafemoral joints. Analogously, in the humerus the distal coverage enables padding restoration of the humeral-olecranon as well as the radio-capitellar (part of the humerus) joint interfaces. Whereas generally the implant may cover the main or primary joint surface of the surgeon's choice contributing to arthritis, consequently reducing symptoms when treated, another alternative would be that the implant can cover any singular surface entirely or partially. It is generally desired that the implant may cover one surface allowing remnant cartilages in other usually opposing or opposite surfaces to glide against the implant polymer with smooth gliding joint motion. This principle allows for retained joint linings or synovium to produce lubricating substances including enzymes for facile joint movement. It also avoids the wear debris that would accrue from polymer rubbing on polymer, as recently recognized in metal on metal prostheses. In certain embodiments, the implant can cover more than one surface in a joint, such as the radio-capitallar joint wherein the distal humerus and the radial head receive prosthetic capping or interpositional application of polymers.

The surgical techniques may be individualized to fit patient need. The implants may be combined with or comprise autologous or allograph tissues such as fascia lata. Surgeons may implant fascia lata above unreconstructable rotator cuff with consequent symptom relief. Polymers can interface with any human tissue and/or with metals or polyethylenes or polyurethanes. Living tissues that can be combined with implants provided herein for repair or reconstruction may be from the same patient (autograph), and cadaver or other member of the same species (allograph) or from another species (xenograph.) Virtually any combination of polymer interpositioning is feasible with the implant concepts provided herein, as anatomy varies among patients in need, and clinical conditions differ with each person. Therefore, although the general or most common construct is expected to cover just one singular and the primary surface of a joint with an implant, any combination of surfaces can be involved allowing versatile custom applications of this implant and method of surgery.

Additionally, whereas implants as noted herein may be available in specified sizes, the material membrane elastic deformation and resilience may allow for calculated malleability toward goodness of fit. In other iterations the fit of implant over the affected joint surface is customized as paring preoperative findings of MRI or CT or PET imaging pathophysiology with intraoperative reconstructive need. Ultimately best fit implants may serve patient restorative requirement with least morbidity.

Locations wherein implants described herein may be additionally or alternatively applicable include all the limb joints of mammals. In the shoulder mainly the glenohumeral joint, though as discussed above the subacromial space are useful loci for renewed padding when pathophysiologies warrant. In the AC or acromioclavicular joint of the shoulder, a Mumford procedure (resection of the distal clavicle) can be avoided by inserted an implant as described herein. Even the TMJ in the jaw may be amenable to therapy using the implants noted herein. Proceeding distally in the aim, the elbow has two relevant joints mentioned earlier, radiocapitellar and ulnohumeral. Depending on 'where the arthritis forms' (as from fracture or disease) the padding should be restored toward normal. Wrist, thumb and finger joints are many and may respond to vesicular implants with better durometry and vicsolubricant delivery than tradition metal or silicon prostheses. Legs started at the hip joint have been shown via Hip implant prototypes to be amenable to polymer capping. Variations per surgeon's choice could evoke special uses as for coverage of trochanteric bursae.

Additionally, the many functions of the implants noted herein may be coupled with cosmetic aspects in order to restore bulk and soft tissue balance after scarring, injury or atrophy, or for purely cosmetic purposes. Treatment for cosmesis especially when coupled with functional or visual injury deficits can provide a reduction in physiological as well as physical pain and discomfort. Therefore the extent minimally invasive implants restore the injured or diseased patient recipient to become hole, they are being used purposefully and as intended.

The knee joint is an initial focus of the figures wherein application to the largest bone (the distal femur) accommodates padding needs for the opposing patella and tibia. The potential use of implants, however, over the contralateral surfaces is an option that should not be ruled out. In the ankle the supratalar, or tibia talar joint will be a useful location as may the subtalar area, depending on pathology present. Indications for use may depend on the patients symptoms, from the history and physical exam, based on studies such as roentgenograms, MRI or CT imaging, and may depend on test result from localized injections. For example, if a talus fracture pain were alleviated by sinus tarsi injection then implant insertion into the subtalar joint would be preferred. The talonavicular and other foot/toe joints are all amenable to renewed padding via an implant noted herein.

Pets, or other animals, such as cows, dogs, and horses, may be served better by polymer joint capping than hip replacement for congenital dysplasia. The successful treatment and rehabilitation of animals can favorably affect the implant recipient and animal's owner, as pets can provide functions necessary for activities of daily living (as a horse helping to plow a field) or an animal relieved of pain from injury or arthritis can also be a comfort to its owner.

Kits

Provided herein are kits comprising multiple implants described herein. A kit may have implants as described herein as well as other implants for other parts of the body. A kit may comprise multiple sizes of a single type of implant. A kit may comprise various implant types, such as the patch, the unicompartment, and/or the dual compartment types of implants described herein. A kit may comprise various couplers, which may be selected by the surgeon depending on his comfort and expertise, and/or based on the particular patient anatomy and/or needs. The kit may further comprise any insertion tools and/or surgery tools that may uniquely assist in implanting the implant in the patient.

In addition to kits involving reparative implants, and insertional tools, there may also be included software for translation of pre-injury data and/or postoperative data collection and analysis, as well as custom implants may be provided.

While particular forms of the invention have been illustrated and described herein, it will be apparent that various modifications and improvements can be made to the invention. One alternative implant construction involves the use of an upper portion of the implant having a net-like construction and filled with balls or ball bearing like elements that are larger than the openings in the netting. The balls or ball bearing like elements provide motion to the implant. The netting and ball bearing like elements may include regeneration agents as previously discussed, and the bearing construction may be directed toward favorable implant movement balanced with content disbursement.

The invention is intended primarily for human use but may be extended to mammalian use. To the extent not otherwise disclosed herein, materials and structure may be of conventional design.

Moreover, individual features of embodiments of the invention may be shown in some drawings and not in others, but those skilled in the art will recognize that individual features of one embodiment of the invention can be utilized in another embodiment. Moreover, individual features of one embodiment may be combined with any or all the features of another embodiment. Accordingly, it is not intended that the invention be limited to the specific embodiments illustrated. It is therefore intended that this invention be defined by the scope of the appended claims as broadly as the prior art will permit.

Terms such as "element", "member", "component", "device", "means", "portion", "section", "steps" and words of similar import when used herein shall not be construed as invoking the provisions of 35 U.S.C § 112(6) unless the following claims expressly use the terms "means for" or "step for" followed by a particular function without reference to a specific structure or a specific action. All patents and all patent applications referred to above are hereby incorporated by reference in their entirety.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. An implant system comprising:
   (a) an implant configured for deployment in a knee joint, the implant comprising
   a first portion that is configured to directly engage a bone of the knee joint wherein the bone is the patella, the tibia or the femur,
   a second portion that is configured to articulate within the knee joint,
   a first appendage configured to couple the first portion to the bone, the first appendage having a pre-set curvature configured to simulate curvature of the bone,
   a second appendage configured to couple the first portion to the bone, the second appendage having a pre-set curvature configured to simulate curvature of the bone,
   a groove between the first appendage and the second appendage,
   wherein the first portion, the second portion, the first appendage, and the second appendage together comprise a single contiguous polymeric sheet,
   and
   (b) at least one coupler wherein the at least one coupler is accommodated by at least one pre-formed hole and/or tab.

2. The implant system of claim 1, wherein the implant is pulled or cinched around the bone.

3. The implant system of claim 1, wherein the polymeric sheet comprises a thermoplastic polyurethane polycarbonate.

4. The implant system of claim 3, wherein the pharmacologic agent comprises growth factors, antibodies, biomolecules, biologics, chemical compounds, tissue regeneration agents, orthobiologics, analgesics, antibiotics, anticancer agents, viscolubricants or combinations thereof.

5. The implant system of claim 1, further comprising a pharmacologic agent.

6. The implant system of claim 5, wherein the tissue regeneration agents comprise stem cells, living chondrocytes, genes or combinations thereof.

7. An implant system comprising:
   (b) an implant configured for deployment between a femur and a patella of a knee joint, the implant comprising
   a first portion that is configured to directly engage a trochlear groove,
   a second portion that is configured to articulate within the knee joint,
   at least one appendage configured to couple the first portion to the trochlear groove,
   wherein the first portion, the second portion, and the at least one appendage, together comprise a single contiguous polymeric sheet,
   and
   (b) at least one coupler wherein the at least one coupler is accommodated by at least one pre-formed hole and/or tab.

8. The implant system of claim 7, wherein the polymeric sheet comprises thermoplastic polyurethane polycarbonate.

9. The implant system of claim 7, further comprising a pharmacologic agent.

10. The implant system of claim 9, wherein the pharmacologic agent comprises growth factors, antibodies, biomolecules, biologics, chemical compounds, tissue regeneration agents, orthobiologics, analgesics, antibiotics, anticancer agents, viscolubricants or combinations thereof.

11. The implant system of claim 10, wherein the tissue regeneration agents comprise stem cells, living chondrocytes, genes or combinations thereof.

* * * * *